US012343387B2

(12) United States Patent
Fornasini et al.

(10) Patent No.: US 12,343,387 B2
(45) Date of Patent: Jul. 1, 2025

(54) FORMULATIONS OF POLYALKYLENE OXIDE-ASPARAGINASE AND METHODS OF MAKING AND USING THE SAME

(71) Applicant: Servier IP UK Limited, Slough (GB)

(72) Inventors: GianFranco Fornasini, Bethesda, MD (US); Nadejda Soukhareva, Derwood, MD (US); Christopher Phillips, Doylestown, PA (US)

(73) Assignee: Servier IP UK Limited, Slough (GB)

( * ) Notice: Subject to any disclaimer, the term of this patent is extended or adjusted under 35 U.S.C. 154(b) by 0 days.

(21) Appl. No.: 16/306,302

(22) PCT Filed: Jun. 1, 2017

(86) PCT No.: PCT/US2017/035461
§ 371 (c)(1),
(2) Date: Nov. 30, 2018

(87) PCT Pub. No.: WO2018/017190
PCT Pub. Date: Jan. 25, 2018

(65) Prior Publication Data
US 2019/0240300 A1    Aug. 8, 2019

Related U.S. Application Data

(60) Provisional application No. 62/344,249, filed on Jun. 1, 2016, provisional application No. 62/344,256, filed on Jun. 1, 2016, provisional application No. 62/344,252, filed on Jun. 1, 2016.

(51) Int. Cl.
| A61K 38/50 | (2006.01) |
| A61K 9/19 | (2006.01) |
| A61K 47/54 | (2017.01) |
| A61K 47/60 | (2017.01) |
| A61K 47/69 | (2017.01) |
| A61P 35/04 | (2006.01) |

(52) U.S. Cl.
CPC ............... *A61K 38/50* (2013.01); *A61K 9/19* (2013.01); *A61K 47/542* (2017.08); *A61K 47/60* (2017.08); *A61K 47/6921* (2017.08); *A61P 35/04* (2018.01); *C12Y 305/01001* (2013.01); *Y02A 50/30* (2018.01)

(58) Field of Classification Search
CPC ........ A61K 38/50; A61K 47/542; A61K 9/19; A61K 47/60; A61K 47/6921; A61K 47/26; A61K 47/40; A61K 47/02; A61K 9/0095; A61P 35/04; A61P 35/02; Y02A 50/30; C12Y 305/01001
See application file for complete search history.

(56) References Cited

U.S. PATENT DOCUMENTS

| 4,179,337 A | 12/1979 | Davis et al. |
| 4,617,271 A | 10/1986 | Nambu |
| 4,729,957 A | 3/1988 | Lee et al. |
| 5,122,614 A | 6/1992 | Zalipsky |
| 5,310,670 A | 5/1994 | Goward |
| 5,324,844 A | 8/1994 | Zalipsky |
| 5,612,460 A * | 3/1997 | Zalipsky ................ A61K 47/60 424/193.1 |
| 5,854,051 A | 12/1998 | Chandrashekar et al. |
| 6,042,825 A | 3/2000 | Chandrashekar et al. |
| 6,087,151 A | 7/2000 | Ario et al. |
| 6,140,101 A | 10/2000 | Ario et al. |
| 6,165,735 A | 12/2000 | Chandrashekar et al. |
| 6,180,095 B1 | 1/2001 | Greenwald et al. |
| 6,251,388 B1 | 6/2001 | Durden |
| 6,274,367 B1 | 8/2001 | Ario et al. |
| 6,277,828 B1 | 8/2001 | Knepp et al. |
| 6,368,845 B1 | 4/2002 | Ario et al. |
| 6,436,396 B1 | 8/2002 | Ario et al. |
| 6,537,547 B1 | 3/2003 | Ario et al. |
| 6,991,788 B1 | 1/2006 | Durden |
| 7,807,436 B2 | 10/2010 | Filpula et al. |
| 8,617,868 B2 | 12/2013 | Van Der Laan et al. |
| 9,051,561 B2 | 6/2015 | Durden |
| 9,127,266 B2 | 9/2015 | Van Der Laan et al. |
| 9,322,008 B2 | 4/2016 | Kundu et al. |

(Continued)

FOREIGN PATENT DOCUMENTS

| CN | 102573917 A | 7/2012 |
| CN | 102138909 B | 3/2013 |

(Continued)

OTHER PUBLICATIONS

Soares, AL et al. Effects of polyethylene glycol attachment on physicochemical and biological stability of *E. coli* L-asparaginase. International Journal of Pharmaceutics. 2002. 237: 163-170. (Year: 2002).*
Ward, KR et al. Protection of the enzyme L-asparaginase during lyophilisation—a molecular modelling approach to predict required level of lyoprotectant. International Journal of Pharmaceutics. 1999. 187: 153-162. (Year: 1999).*
Hellman, K et al. The effect of freeze-drying on the quaternary structure of L-asparaginase from Erwinia carotovora. Biochimica et Biophysica Acta. 1983. 749: 133-142. (Year: 1983).*
Pikal-Cleland, KA et al. Protein denaturation during freezing and thawing in phosphate buffer systems: monomeric and tetrameric beta-glucosidase. Archives of Biochemistry and Biophysics. 2000. 384(2): 398-406. (Year: 2000).*

(Continued)

*Primary Examiner* — David W Berke-Schlessel
*Assistant Examiner* — Susan E. Fernandez
(74) *Attorney, Agent, or Firm* — Troutman Pepper Locke LLP

(57) ABSTRACT

Aspects of the invention include polyalkylene oxide-asparaginase compositions. In some instances, the composition is a lyophilized storage stable composition. In some instances, the lyophilized compositions include one or more of a buffer, a salt, and a sugar. Aspects of the invention further include methods of making the compositions. The compositions find use in a variety of applications, e.g., in the treatment of a neoplastic condition in a subject.

10 Claims, 13 Drawing Sheets

(56) References Cited

U.S. PATENT DOCUMENTS

| | | | |
|---|---|---|---|
| 2008/0260820 A1* | 10/2008 | Borrelly | A61K 38/27 424/463 |
| 2010/0143324 A1 | 6/2010 | Mononen et al. | |
| 2015/0224207 A1 | 8/2015 | Kozlowski et al. | |
| 2016/0060613 A1 | 3/2016 | Abribat | |

FOREIGN PATENT DOCUMENTS

| | | |
|---|---|---|
| EP | 0875252 A2 | 11/1998 |
| EP | 0893439 B1 | 7/2005 |
| RU | 2126265 C1 | 2/1999 |
| RU | 2441914 C1 | 2/2010 |
| RU | 2497500 C2 | 11/2013 |
| WO | 9704801 A1 | 2/1997 |
| WO | 99/48535 A1 | 9/1999 |
| WO | 2011/003886 A1 | 1/2011 |

OTHER PUBLICATIONS

Townsend, MW et al. Use of lyoprotectants in the freeze-drying of a model protein, ribonuclease A. J. Parenter. Sci. Technol. 1988. 42(6): 190-199 (Year: 1988).*

Van den Berg, L et al. Effect of freezing on the pH and composition of sodium and potassium phosphate solutions: The reciprocal system KH2PO4—Na2HPO4—H2O. Archives of Biochemistry and Biophysics. 1959. 81: 319-329. (Year: 1959).*

International Search Report and Written Opinion dated Jan. 11, 2018 for Application No. PCT/US17/35461.

Extended European Search Report issued Nov. 18, 2019 in connection with EPO No. 17831465.4.

Varshney et al., "Part II Lyophilized Biologics and Vaccines—Modality Considerations" In: "Lyophilized Biologics and Vaccines", Jan. 1, 2015, XP55640506, ISBN: 978-1-4939-2382-3, pp. 92-100.

Sandeeo et al., "Excipients: Their Role in Parenteral Dosage Forms", Jan. 1, 2000, Encyclopedia of Pharmaceutical Technology, pp. 137-172, XP009105976, ISBN: 978-0-8247-2818-2.

Wang, "Lyophilization and development of solid protein pharmaceuticals", International Journal of Pharmaceutics, 2000, vol. 203, pp. 1-60.

Carpenter et al., "Rational Design of Stable Protein Formulations: Theory and Practice", Pharmaceutical Biotechnology, 2002, vol. 13. Springer, Boston, MA. 109-127.

Pramanick et al., "Excipient selection in parenteral formulation development", Pharma Times, 2013, vol. 45, No. 3, pp. 65-77.

Office Action mailed Jun. 26, 2020, issued in Russian Application No. 2018 146 395.

Examination Report issued Nov. 14, 2020 in Australian Application No. 2017299374.

Chinese Office Action Issued In CN 201780046796.6 malled Dec. 1, 2020.

Angiolillo et al., "Pharmacokinetic and Pharmacodynamic Properties of Calaspargase Pegol Escherichia coli L-Asparaginase in the Treatment of Patients With Acute Lymphoblastic Leukemia: Results From Children's Oncology Group Study AALL07P4", Journal of Clinical Oncology, vol. 32, No. 34, 2014, pp. 3874-3882.

Oncaspar prescribing information, sigma-tau Pharmaceuticals, Inc. Mar. 2011.

Remmele et al., "Development of Stable Lyophilized Protein Drug Products", Current Pharmaceutical Biotechnology, 2012, vol. 13, pp. 471-496.

Ohtake et al., "Interactions of formulation excipients with proteins in solution and in the dried state", Advanced Drug Delivery Reviews, 2011, vol. 63, pp. 1053-1073.

Annexes to the European Public Asessment Report (EPAR) regarding Spectrila, Jan. 14, 2016.

Faschinger et al., "Development of a Lyophilized Formulation of Pegaspargase and Comparability Versus Liquid Pegasparagase", Adv Ther, 2019, vol. 36, pp. 2106-2121.

Oncaspar 750 E/ml, Pulver zur Herstellung einer Injektions-/Infusionslosung, Servier Deutchland GmbH, Nov. 20, 2020.

Mosharraf et al., "Formulation, lyophilization and solid-state properties of a pegylated protein", International Journal of Pharmaceutics, 2007, vol. 336, pp. 215-232.

Bhatnagar et al., "Investigation of PEG Crystallization in Frozen and Freeze-dried PEGylated Recombinant Human Growth Hormone-Sucrose Systems: Implications on Storage Stability" Journal of Pharmaceutical Sciences, 2011, vol. 100, No. 8, pp. 3062-3075.

Franks, "Freeze-drying of bioproducts: putting principles into practice" European Journal of Pharmaceutics and Biopharmaceutics, 1998, vol. 45, No. 221-229.

Notice of Opposition issued in EP 17831465.4 dated Sep. 5, 2022.

Alrazzak et al., "The Incidence of Hypersensitivity Reactions to Pegylated Asparaginase in Children with Acute Lymphoblastic Leukemia: A City-wide Experience", J. Pediatr. Hematol. Oncol, 2016, vol. 38, No. 1, pp. e16-e20.

Japanese Office Action Issued in application No. 2022-030538 dated Mar. 20, 2023.

Carpenter et al., "Rational Design of Stable Lyophilized Protein Formulations: Some Practical Advice", Pharmaceutical Research, 1997, vol. 14, No. 8, pp. 969-975.

Zhang et al., "A Perspective on the Maillard Reaction and the Analysis of Protein Glycation by Mass Spectrometry: Probing the Pathogenesis of Chronic Disease", J. Proteome, Res. 2009, vol. 8, No. 2, pp. 754-769.

Alconcel et al., "FDA-approved poly(ethylene glycol)-protein conjugate drugs", Polym. Chem, 2011, vol. 2, pp. 1442-1448.

Wang et al., "Engineering an Arginine Catabolizing Bioconjugate: Biochemical and Pharmacological Characterization of PEGylated Derivatives of Arginine Deiminase from Mycoplasma arthritidis", Bioconjugate Chem., 2006, vol. 17, No. 6, pp. 1447-1459.

Santi et al., "Predictable and tunable half-life extension of therapeutic agents by controlled chemical release from macromolecular conjugates", PNAS, 2012, vol. 109, No. 16, pp. 6211-6216.

Martinez et al., "Branched poly(ethylene glycol) linkers", Macromol. Chem. Phys., 1997, vol. 198, pp. 2489-2498.

Office Action dated Jul. 24, 2023, issued in Japanese Application No. 2022-030538.

Asparlas BLA Approval, Dec. 2018, 8 pages.

Asparlas FDA Label, Dec. 2022, 16 pages.

Boards of Appeal letter of the opponent dated Dec. 12, 2024 issued in EP Application No. 17831465.4 (EP Patent No. 3463308).

Davis et al., "Stability of lyophilized sucrose formulations of an IgG1: subvisible particle formation", Pharmaceutical Development and Technology, 2013, vol. 18, No. 4, pp. 883-896.

Wang et al., "Antibody Structure, Instability, and Formulation", Journal of Pharmaceutical Sciences, 2007, vol. 96, No. 1, pp. 1-26.

Murphy et al., "Structure, Stability, and Mobility of a Lyophilized IgG1 Monoclonal Antibody as Determined Using Second-Derivative Infrared Spectroscopy", Journal of Pharmaceutical Sciences, 2012, vol. 101, No. 1, pp. 81-91.

Rey et al., "Freeze Drying/Lyophilization of Pharmaceutical and Biological Products", Informa Healthcare, 2010, Chapters 7 and 8, 76 pages.

Sek, "Breaking Old Habits: Moving Away From Commonly Used Buffers in Pharmaceuticals", European Pharmaceutical Review, 2012, vol. 17, Issue 3, pp. 37-41.

Pikal-Cleland et al., "Lyophilization-Induced Protein Denaturation in Phosphate Buffer Systems: Monomeric and Tetrameric Beta-Galactosidase", Journal of Pharmaceutical Sciences, 2001, vol. 90, No. 9, pp. 1255-1268.

Bhatnagar et al., "Protein stability during freezing: separation of stresses and mechanisms of protein stabilization", Pharmaceutical Development and Technology, 2007, vol. 12, No. 5, pp. 505-523.

Liebner, "Formulation of PEGylated and HESylated Biopharmaceuticals", Dissertation, Aug. 22, 2015.

Zalipsky et al., Chapter 10. "Succinimidyl carbonates of polyethylene glycol. Useful reactive polymers for preparation of protein conjugates", in: Dunn et al., Polymeric Drugs and Drug Delivery Systems, American Chemical Society, 1991, pp. 91-100.

Oncaspar: EPAR—Public assessment report, 122 pages, Jan. 29, 2016, https://www.ema.europa.eu/en/documents/assessment-report/

(56) References Cited

OTHER PUBLICATIONS oncaspar-epar-public-assessment-report_en.pdf available from https://www.ema.europa.eu/en/medicines/human/EPAR/oncaspar.
Office Action issued in New Zealand Application No. 788906 mailed Jan. 29, 2025.

* cited by examiner

FORMULATIONS OF POLYALKYLENE OXIDE-ASPARAGINASE AND METHODS OF MAKING AND USING THE SAME

CROSS REFERENCE TO RELATED APPLICATIONS AND INCORPORATION BY REFERENCE

This application is a U.S. National Phase Application under 35 U.S.C. § 371 of International Patent Application No. PCT/US17/35461, filed Jun. 1, 2017 and published on Jan. 25, 2018 as International Publication No. WO 2018/017190, which claims the benefit of U.S. Provisional Patent Application No. 62/344,249, filed Jun. 1, 2016; U.S. Provisional Patent Application No. 62/344,252, filed Jun. 1, 2016, and U.S. Provisional Patent Application No. 62/344,256, filed Jun. 1, 2016, each of which are incorporated by reference in their entirety.

INTRODUCTION

L-asparaginase is an enzyme that hydrolyzes the amino acid L-asparagine via a deamination reaction to produce L-aspartate and ammonia. *E. coli* contain two asparaginase isoenzymes: L-asparaginase I and L-asparaginase II. L-asparaginase I is located in the cytosol and has a low affinity for asparagine. However, L-asparaginase II is located in the periplasm and has a high affinity for L-asparagine. *E. coli* L-asparaginase II is a tetramer of identical subunits. *E. coli* L-asparaginase II is also known as L-asparagine amidohydrolase, type EC-2, EC 3.5.1.1.

L-asparaginase is known to have therapeutic value in the treatment of leukemia. L-asparaginase is an amidohydrolase which catalyzes L-asparagine into L-aspartic acid and ammonia. It plays a major role in the metabolism of L-asparagine in plants, animals and microorganisms. It is now well established that the therapeutic activity of the enzyme is caused by the depletion/removal of circulatory L-asparagine, an essential nutrient for the proliferation and survival of tumor (leukemic) cells which are compromised in L-asparagine synthesis ability, but not for the normal cells. The administration of L-asparaginase to leukemic patients induces the selective death of the tumor cells by hydrolyzing L-asparagine, resulting in the treatment of malignant tumors.

In some cases, L-asparaginase, by itself, suffers from typical disadvantages of protein therapeutics, such as a high rate of clearance of a protein foreign to the patient, and the potential for inducing an immune response in a patient treated with this enzyme. In order to address these shortcomings, a polyethylene glycol-conjugated derivative of L-asparaginase (PEG-asparaginase) can be used. PEG-asparaginase can be produced using L-asparaginase II extracted from *E. coli* and can be substantially non-antigenic and can exhibit a reduced rate of clearance from the circulation of a patient.

A PEG-asparaginase liquid injection formulation (Oncaspar®) has been previously approved for commercial marketing by the U.S. Food and Drug Administration. Oncaspar® was approved as a first-line treatment of patients with acute lymphoblastic leukemia (ALL) as a component of a multi-agent chemotherapy regimen. In addition, Oncaspar® was approved for the treatment of patients with ALL and hypersensitivity to asparaginase (e.g., native forms of L-asparaginase).

SUMMARY

Aspects of the invention include polyalkylene oxide-asparaginase compositions. In some instances, the compositions include one or more of a buffer and a salt. In other aspects, the composition is a lyophilized storage stable composition. In some instances, the lyophilized compositions include one or more of a buffer, a salt, and a sugar. Aspects of the invention further include methods of making the compositions. The compositions find use in a variety of applications, e.g., in the treatment of a neoplastic condition in a subject.

DEFINITIONS

Figure 1:
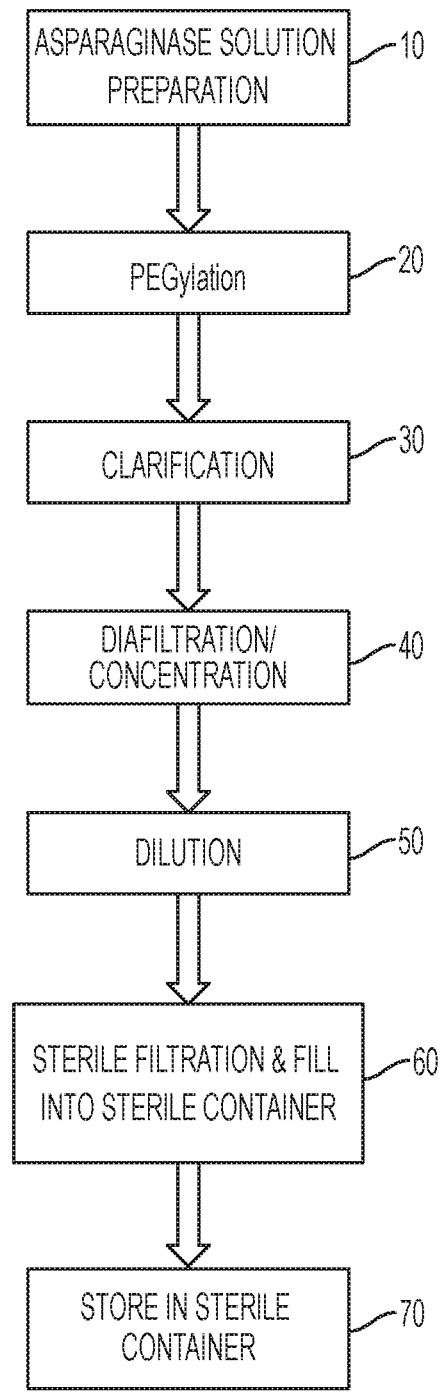
FIG. 1 shows a process flow diagram for a method of making a lyophilized storage stable composition according to embodiments of the present disclosure.

In describing the embodiments of the present disclosure, the following terms may be employed, and are intended to be defined as indicated below.

By "substantially purified" is meant the isolation of a substance such that the substance includes the majority of the sample in which it resides. For example, a sample that is substantially purified contains 50% or more of the substance of interest, such as 60% or more of the substance of interest, such as 75% or more of the substance of interest, such as 90% or more of the substance of interest, such as 95% or more of the substance of interest, including 99% or more of the substance of interest. Any convenient protocol may be employed for purifying the substance of interest and includes, but is not limited to, filtration (e.g., diafiltration, ultrafiltration, etc.), selective precipitation, crystallization, ion-exchange chromatography, affinity chromatography and sedimentation according to density.

By "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

The terms "patient" and "subject" are used interchangeably and are used in their conventional sense to refer to a living organism suffering from or prone to a condition that can be prevented or treated by administration of a composition of the present disclosure, and includes both humans and non-human animals. Examples of subjects include, but are not limited to, humans, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, adult, juvenile and newborn individuals are of interest.

"Pharmaceutically effective amount" and "therapeutically effective amount" refer to an amount of a compound or composition sufficient to treat a specified disorder or disease or one or more of its symptoms and/or to prevent the occurrence of the disease or disorder. In reference to neoplastic conditions, a pharmaceutically or therapeutically effective amount includes an amount sufficient to, among other things, cause the amount and/or occurrence of the cancer in a subject to decrease, and/or decrease the growth rate of the cancer.

The term "treating" or "treatment" as used herein means the treating or treatment of a disease or medical condition in a patient, such as a mammal (e.g., a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The term "physiological conditions" is meant to encompass those conditions compatible with living cells, e.g., predominantly aqueous conditions of a temperature, pH, salinity, etc. that are compatible with living cells.

Before the embodiments of the present disclosure are described in greater detail, it is to be understood that the embodiments are not limited to the particular embodiments described herein; as such embodiments may vary. It is also to be understood that the terminology used herein is for the purpose of describing particular embodiments only, and the terminology is not intended to be limiting. The scope of the embodiments of the present disclosure will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the embodiments of the present disclosure. The upper and lower limits of these smaller ranges may independently be included in the smaller ranges and are also encompassed within the embodiments of the present disclosure, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the embodiments of the present disclosure. Any recited method may be carried out in the order of events recited or in any other order that is logically possible. Although any methods and materials similar or equivalent to those described herein may also be used in the practice or testing of the embodiments of the present disclosure, representative illustrative methods and materials are now described.

DETAILED DESCRIPTION

Aspects of the invention include polyalkylene oxide-asparaginase compositions. In some instances, the compositions include one or more of a buffer and a salt. Aspects of the invention further include methods of making the compositions. The compositions find use in a variety of applications, e.g., in the treatment of a neoplastic condition in a subject.

Aspects of the invention include lyophilized storage stable polyalkylene oxide-asparaginase compositions. In some instances, the lyophilized compositions include one or more of a buffer, a salt, and a sugar. Aspects of the invention further include methods of making the compositions. The compositions find use in a variety of applications, e.g., in the treatment of a neoplastic condition (e.g., acute myeloid leukemia (AML)) in a subject.

Aspects of the invention include a method of treating a subject for AML. The methods include administering to the subject a dosage of a polyalkylene oxide-asparaginase effective to treat the subject for AML. Aspects of the invention further include polyalkylene oxide-asparaginase containing compositions and kits that can be used in the subject methods.

In further describing the embodiments of the present disclosure, compositions (e.g., liquid and lyophilized) are described first in greater detail. Next, methods of making, methods of using and kits that include the subject composition are also described.

Compositions

Aspects of the present disclosure include a composition of a polyalkylene oxide-asparaginase that includes a polyalkylene oxide group covalently linked by a linker to an asparaginase. The composition may also include one or more of a buffer and a salt. In certain embodiments, the composition is a lyophilized storage stable composition. The lyophilized storage stable composition may also include one or more of a buffer, a salt and a sugar.

As described herein, compositions of the present disclosure may include a polyalkylene oxide-asparaginase. A polyalkylene oxide-asparaginase includes an asparaginase covalently linked by a linker to one or more polyalkylene oxide groups. Asparaginase is an enzyme that may be composed of four identical subunits with one active site per tetramer. For example, the asparaginase enzyme can be L-asparaginase (e.g., L-asparaginase II), which hydrolyzes the amino acid L-asparagine (also known as (S)-2,4-diamino-4-oxobutanoic acid, or asparaginine, or abbreviated as Asn or N) to produce L-aspartate (also known as (S)-2-aminosuccinic acid) and ammonia according to the following reaction:

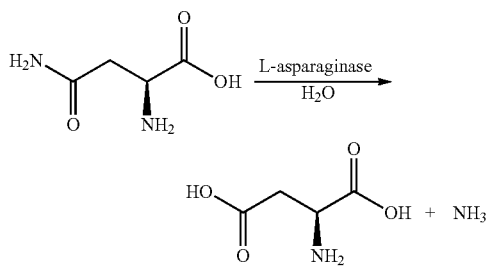

In some cases, asparaginase can hydrolyze the amino acid L-glutamine (also known as (S)-2,5-diamino-5-oxopentanoic acid, or abbreviated as Gln or Q) to produce L-glutamate (also known as (S)-2-aminopentanedioic acid) and ammonia according to the following reaction:

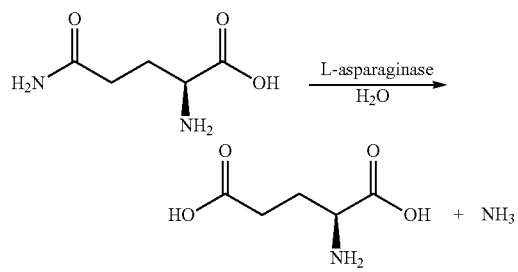

The above reactions that are mediated by L-asparaginase may also be referred to as a deamination reaction. In some instances, the L-asparaginase in the composition is derived from a prokaryotic source, such as a bacteria, including but not limited to the bacteria $Escherichia\ coli$ ($E.\ coli$). As such, the asparaginase in the subject composition may be an $E.\ coli$ asparaginase. In some cases, the asparaginase is expressed by $E.\ coli$. The asparaginase can be recovered and purified from a culture medium containing the $E.\ coli$ that expresses the asparaginase. In addition to wild type asparaginases, the asparaginase may also be one that is a non-naturally occurring asparaginase and/or synthetically produced asparaginase and/or an active fragment of a naturally occurring and/or synthetic asparaginase. Examples of asparaginases that may be employed in embodiments of the invention include, but are not limited to, those described in: U.S. Pat. Nos. 9,322,008; 9,127,266; 9,051,561; 8,617,868; 7,807,436; 6,991,788; 6,537,547; 6,436,396; 6,368,845; 6,274,367; 6,251,388; 6,165,735; 6,140,101; 6,087,151; 6,042,825; 5,854,051; 5,310,670; 4,729,957 and 4,617,271; the disclosures of which are herein incorporated by reference.

As described above, the asparaginase in the polyalkylene oxide-asparaginase composition is an asparaginase covalently linked to one or more polyalkylene oxide groups. For instance, the asparaginase may include one or more polyalkylene oxide groups covalently linked to the asparaginase via a post-translational modification process. The polyalkylene oxide-asparaginase may include one or more polyalkylene oxide groups covalently linked to the asparaginase at one or more positions on the asparaginase. For example, a polyalkylene oxide group may be covalently linked to an amino acid residue of the asparaginase. In some cases, the polyalkylene oxide group is covalently linked to an amino group of an amino acid residue of the asparaginase. In some embodiments, the polyalkylene oxide group is covalently linked to an amino acid side chain of an N-terminal amino acid in the asparaginase. In some embodiments, the polyalkylene oxide group is covalently linked to an epsilon-amino group of lysine (K) in the asparaginase. In some embodiments, the polyalkylene oxide group is covalently linked to an amino acid side chain of the N-terminal amino acid and an epsilon-amino group of lysine (K) in the asparaginase. In some cases, the polyalkylene oxide-asparaginase is substantially non-antigenic. By "non-antigenic" or "substantially non-antigenic" is meant a composition that does not elicit a significant immune response in a subject when the composition is administered to the subject. In some instances, the polyalkylene oxide-asparaginase has a reduced rate of clearance from the circulation of a subject as compared to an unmodified asparaginase. For example, the elimination half-life of a polyalkylene oxide-asparaginase may be 1 day or more, such as 2 days or more, or 3 days or more, or 4 days or more, or 5 days or more, or 6 days or more, or 7 days or more, or 8 days or more, or 9 days or more, or 10 days or more, or 11 days or more, or 12 days or more, or 13 days or more, or 14 days or more, or 15 days or more, or 16 days or more, or 17 days or more, or 18 days or more, or 19 days or more, or 20 days or more. In some embodiments, the elimination half-life of a polyalkylene oxide-asparaginase is 3 days or more. In some embodiments, the elimination half-life of a polyalkylene oxide-asparaginase is 5 days or more.

The polyalkylene oxide group that is linked to the asparaginase can be any physiologically compatible polyalkylene oxide group. Poly(alkylene oxide)s (PAO), which are also known as polyoxyalkylenes (POA), are made by the polymerization of alkylene oxides (e.g., ethylene oxide, propylene oxide, butylene oxide). A homopolymer is formed only from one type of alkylene oxide while a copolymer is formed from two or more different alkylene oxides, known as alkylene oxide copolymers (AOC). Examples of the former are poly(ethylene oxide) (PEO), which is a polymer of ethylene oxide (EO), and poly(propylene oxide) (PPO), which is a polymer of propylene oxide (PO). Poly(ethylene oxide) is also commonly known as polyethylene glycol (PEG) or polyoxyethylene (POE). The molecular weight of such polymers is generally characterized as the average of a distribution of lengths (or repeat units). In addition to the standard linear forms, branched or star forms of poly(alkylene oxide)s are produced by initiating the polymerization reaction with a polyfunctional initiator with multiple hydroxyl-, amino-, or thiol-groups each of which can serve as a starting point for polymer chain growth. For example, the use of glycerol (three hydroxyl groups) as an initiator results in a three-armed branched polymer, while pentaerythritol results in a four-armed polymer. Conventionally, polymers of this type with 3 to 10 arms are termed "branched" while those with more than 10 arms are termed "star" polymers. "Comb" copolymers are similar to branched and star forms, but the initiator for comb copolymers is a polyfunctional polymer with multiple hydroxyl-, amino-, or thiol-groups spaced along the initiator backbone, each of which can serve as a starting point for polymer chain growth. "Graft" copolymers are made by the addition of pendant polymer chains along a polymer backbone that possesses unsaturated C=C bonds or pendant functional groups (e.g., hydroxyl) from which pendant chains can be added by using a reactive monofunctional polymer chain. All poly(alkylene oxide)s contain, in addition to multiple alkylene oxide-derived repeat units, a single residue corresponding to the molecule used to initiate the polymer synthesis. For linear polymers, this may be an alkylene glycol corresponding to the alkylene oxide used for the synthesis (e.g., ethylene glycol and ethylene oxide, respectively) and thus the initiator-derived residue will be indistinguishable from the other repeat units in the polymer chain. But small molecules other than alkylene glycols are often used as initiators, examples include methanol or N-butanol (for linear polymers) and trimethylol propane, glycerol, and pentaerythritol (for branched polymers) or ethylene diamine. The mass of initiator relative to the mass of the final polymer chain is generally very small and can usually be neglected. Thus, the term poly(alkylene oxide) is used here in its customary sense, and includes both poly(alkylene oxide)s initiated with an alkylene glycol molecule and poly(alkylene oxide)s initiated with another small molecule.

In certain embodiments, a physiologically compatible polyalkylene oxide group is substantially stable in conditions compatible with living cells, e.g., predominantly aqueous conditions of a temperature, pH, salinity, etc. that are compatible with living cells. In certain embodiments, a polyalkylene oxide group is water-soluble. The term "water-soluble polymer" refers to a polyalkylene oxide group that is substantially soluble in water, such as in aqueous conditions found in the body of a subject. Polyalkylene oxide groups of interest include, but are not limited to straight chain polyalkylene glycols. Straight chain polyalkylene glycols employed in certain embodiments of the invention are of the following structural formula:

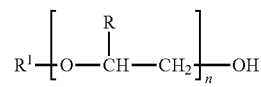

wherein R is selected from the group consisting of hydrogen, lower alkyl and mixtures thereof, $R_1$ is selected from the group consisting of hydrogen and lower alkyl, and n is a positive integer. By "lower alkyl" is meant an alkyl group having from one to four carbon atoms, i.e., methyl, ethyl, propyl, butyl, and isomers of the foregoing. R may be selected from the group consisting of hydrogen, methyl, and mixtures thereof, $R_1$ may be selected from the group consisting of hydrogen and methyl, and n may be a positive integer selected to provide for the desired polymeric size. In some instances, the poly(alkylene glycols) employed in embodiments of the invention are poly(ethylene glycol), poly(propylene glycol), mixtures thereof, and copolymers of poly(ethylene glycol) and poly(propylene glycol), wherein one of the terminal hydroxyl groups of the polymer may be substituted with a lower alkyl group.

In some embodiments, the polyalkylene oxide is a polyethylene glycol (PEG). In certain embodiments, the polyethylene glycol (PEG) has a molecular weight of 1,000 to 20,000 daltons. In certain embodiments, the PEG has a molecular weight of 1,000 to 20,000 daltons, or 1,000 to 19,000 daltons, or 1,000 to 18,000 daltons, or 1,000 to 17,000 daltons, or 1,000 to 16,000 daltons, or 1,000 to 15,000 daltons, or 1,000 to 14,000 daltons, or 1,000 to 13,000 daltons, or 1,000 to 12,000 daltons, or 1,000 to 11,000, or 1,000 to 10,000, or 1,500 to 10,000 daltons, or 2,000 to 10,000 daltons, or 2,000 to 9,000 daltons, or 2,000 to 8,000 daltons, or 2,000 to 7,000 daltons, or 2,000 to 6,000 daltons, or 3,000 to 6,000 daltons or 4,000 to 6,000 daltons, or 4,500 to 5,500 daltons. In certain embodiments, the PEG has a molecular weight of 2,000 to 10,000 daltons. In certain embodiments, the PEG has a molecular weight of 4,000 to 6,000 daltons. In certain embodiments, the PEG has a molecular weight of 5,000 daltons. In some instances, the polyethylene glycol is a methoxypolyethylene glycol (e.g., monomethoxypolyethylene glycol, or "mPEG").

As described above, the polyalkylene oxide group may be covalently attached to the asparagmase. In some cases, the polyalkylene oxide group is covalently linked by a linker to the asparagmase. As such, the polyalkylene oxide group may be covalently attached to the asparaginase through the linker. The linker may be any convenient functional group that allows for attachment of the polyalkylene oxide group to the asparaginase. For example, the linker may include a reactive functional group that provides for a covalent bond between the polyethylene oxide group and the asparaginase. In some cases, the linker includes a reactive functional group that provides for a covalent bond between the polyethylene oxide group and an amino acid residue of the asparaginase. For instance, the linker may include a reactive functional group that provides for a covalent bond between the polyalkylene oxide group and an amino group of an amino acid residue of the asparaginase. Examples of such reactive functional groups include, but are not limited to, p-nitrophenoxy, thiazolidinyl thione, N-hydroxysuccinimidyl, or other suitable reactive functional groups such as, but not limited to, N-hydroxybenzotriazolyl, halogen, N-hydroxyphthalimidyl, imidazolyl, O-acyl ureas, pentafluorophenol or 2,4,6-trichlorophenol, and the like. In some cases, the reactive functional group of the linker is N-hydroxysuccinimidyl. Accordingly, following covalent attachment of the polyalkylene oxide group to the asparaginase, the linker may include functional groups, such as, but not limited to, a urethane linker (also known as a carbamate linker), a succinate linker, and the like.

In certain embodiments, the linker includes a urethane linker (also known as a carbamate linker). For example, a reaction for the attachment of methoxypolyethylene glycol (mPEG) to an amino group of an amino acid of a polypeptide (e.g., asparaginase) through a urethane (carbamate) linker is shown below.

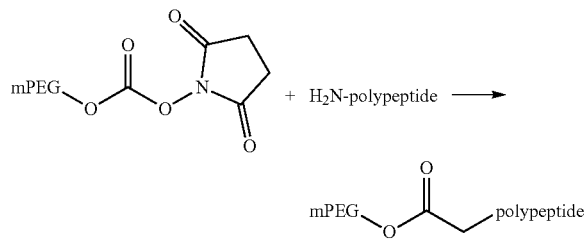

In the reaction shown above, methoxypolyethylene glycol succinimidyl carbonate (also referred to as SC-PEG) is reacted with an amino group of an amino acid of a polypeptide (e.g., asparaginase) to produce a polyethylene glycol-asparaginase with a urethane (carbamate) linker. SC-PEG-asparaginase is also described in Angiolillo, A L., et al., "Pharmacokinetic (PK) and pharmacodynamics (PD) properties of SC-PEG *E. coli* 1-asparaginase (EZN-2285) in the treatment of patients with acute lymphoblastic leukemia (ALL): Results from Children's Oncology Group (COG) study AALL07P4", 2012 American Society of Clinical Oncology (ASCO) Annual Meeting, Poster 9543; and Angiolillo, A L., et al., "Pharmacokinetic and Pharmacodynamic Properties of Calaspargase Pegol *Escherichia coli* L-Asparaginase in the Treatment of Patients With Acute Lymphoblastic Leukemia: Results From Children's Oncology Group Study AALL07P4", *J Clin. Oncology*, 32(34), 2014, 3874-3882.

In certain embodiments, the linker includes a succinate linker (also referred to as a succinyl linker). For example, a reaction for the attachment of methoxypolyethylene glycol (mPEG) to an amino group of an amino acid of a polypeptide (e.g., asparaginase) through a succinate linker is shown below.

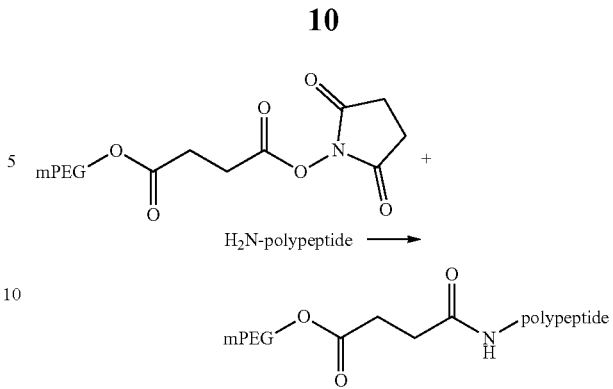

In the reaction shown above, methoxypolyethylene glycol succinimidyl succinate (also referred to as SS-PEG) is reacted with an amino group of an amino acid of a polypeptide (e.g., asparaginase) to produce a polyethylene glycol-asparaginase with a succinate linker. SS-PEG-asparaginase is also described in U.S. Pat. Nos. 5,122,614; 5,324,844; and 5,612,460, the disclosures of each of which are incorporated herein by reference.

In certain embodiments, the composition that contains the polyalkylene oxide-asparaginase is a dehydrated composition. As used herein, a dehydrated composition is a composition that includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less water as measured by Karl Fischer (KF) titration. In some cases, a dehydrated composition has 3% or less water as measured by Karl Fischer titration. In some cases, a dehydrated composition has 1% or less water as measured by Karl Fischer titration. In some cases, a dehydrated composition has 0.5% or less water as measured by Karl Fischer titration. Any convenient protocol may be used to produce a dehydrated composition, such as increasing the temperature of the composition (e.g., heating), reducing the pressure, lyophilization (also known as freeze-drying), and the like, and combinations thereof.

In certain embodiments, lyophilization is used to produce a dehydrated composition, and thus the composition (e.g., the composition that contains the polyalkylene oxide-asparaginase) is a lyophilized composition. In some instances, a lyophilized composition is a composition where water has been removed from the composition by sublimation, where the water in the composition undergoes a phase transition from a solid to a gas. For example, a lyophilized composition may be a composition where water has been removed from the composition by freezing the composition (e.g., freezing the water in the composition) and then reducing the pressure surrounding the composition such that the water in the composition undergoes sublimation. As described above, a lyophilized composition may include water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In certain embodiments, the lyophilized composition may include water in a low amount, such as between about 0.1% to about 25%, or about 0.25% to about 20%, or about 0.5% to about 15%, or about 1% to about 10%, or about 2% to about 9%, or about 3% to about 8%, or about 4% to about 7%, or about 5% to about 6% as measured by Karl Fischer (KF) titration. In certain embodiments, the lyophilized composition may include water in a low amount, such as between about 0.1% to about 5%, or about 0.25% to about 4%, or about 0.5% to about 3%, or about 1% to about 2% as measured by Karl Fischer (KF) titration. In some cases, a lyophilized composition has 3% or less water as measured by Karl Fischer titration. In some cases, a lyophilized composition has 1% or less water as measured by Karl Fischer titration. In some cases, a lyophilized composition has 0.5% or less water as measured by Karl Fischer titration.

Due to the low water content of a lyophilized composition as described above, the lyophilized composition may be in the form of a solid. In some cases, the solid lyophilized composition is a powder. In some cases, a lyophilized composition may facilitate storage of the composition for an extended period of time (e.g., as compared to a liquid formulation of the same composition). For instance, a lyophilized composition may be a storage stable composition (e.g., a lyophilized storage stable composition), where the composition is substantially stable for an extended period of time. By "stable" or "storage stable" or "substantially stable" is meant a composition that does not significantly degrade and/or lose activity over an extended period of time. For example, a storage stable composition may not have significant impurities due to degradation of the composition over an extended period of time, such as 10% or less impurities, or 9% or less, or 8% or less, or 7% or less, or 6% or less, or 5% or less, or 4% or less, or 3% or less, or 2% or less, or 1% or less degradation products over an extended period of time. In certain embodiments, a storage stable composition may have between about 1% to about 10%, or about 2% to about 9%, or about 3% to about 8%, or about 4% to about 7%, or about 6% to about 5% less degradation products over an extended period of time. In certain instances, a storage stable composition has 5% or less impurities over an extended period of time. In some cases, a storage stable composition substantially retains its activity over an extended period of time, such as retains 100% of its activity, or 99% or more, or 98% or more, or 97% or more, or 96% or more, or 95% or more, or 94% or more, or 93% or more, or 92% or more, or 91% or more, or 90% or more, or 85% or more, or 80% or more, or 75% or more of its activity over an extended period of time. In some embodiments, a storage stable composition substantially retains its activity over an extended period of time, such as between about 75% to about 100%, or about 80% to about 99%, or about 85% to about 98%, or about 90% to about 97%, or about 91% to about 96%, or about 92% to about 95%, or about 93% to about 94% more of its activity over an extended period of time. For example, a storage stable composition may retain 90% or more of its activity over an extended period of time. In some cases, a storage stable composition retains 95% or more of its activity over an extended period of time. An extended period of time is a period of time such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. For instance, an extended period of time may be 6 months or more. In some cases, an extended period of time is 9 months or more. In some cases, an extended period of time is 1 year (e.g., 12 months) or more. In some cases, an extended period of time is 1.5 years (e.g., 18 months) or more. In some cases, an extended period of time is 2 years (e.g., 24 months) or more. In some embodiments, an extended period of time can be between about 1 week to about 3 weeks, or about 1 month to about 6 months, or about 6 months to about 9 months, or about 1 year to about 1.5 years, or about 1 year to about 2 years, or about 1 year to about 3 years, or about 1 year to about 4 years, or about 1 year to about 5 years. In some embodiments, a storage stable composition is substantially stable for an extended period of time at ambient temperature, such as a temperature of 20 to 40° C., or 25 to 35° C., or 25 to 30° C. In some instances, a storage stable composition is substantially stable for an extended period of time at a temperature less than ambient temperature, such as a temperature of 0 to 20° C., or 0 to 15° C., or 0 to 10° C., or 2 to 8° C.

In some cases, the composition includes a therapeutically effective amount of the polyalkylene oxide-asparaginase. The enzymatic activity of the polyalkylene oxide-asparaginase can be measured in International Units (IU), which corresponds to the amount of enzyme required to generate 1 µmol of ammonia per minute at a pH of 7.3 and temperature of 37° C. In some cases, the polyalkylene oxide-asparaginase may be present in the composition in an amount (e.g., the polyalkylene oxide-asparaginase may have a potency (activity)) ranging from 100 to 5,000 IU/g, such as 500 to 4,500 IU/g, or 500 to 4,000 IU/g, or 500 to 3,500 IU/g, or 500 to 3,000 IU/g, or 500 to 2,500 IU/g, or 500 to 2,000 IU/g, or 500 to 1,500 IU/g, or 500 to 1,000 IU/g, or 600 to 900 IU/g, or, or 700 to 800 IU/g. In certain instances, the polyalkylene oxide-asparaginase may be present in the composition in an amount ranging from 500 to 1,000 IU/g. For example, the polyalkylene oxide-asparaginase may have a potency (activity) ranging from 500 to 1,000 IU/g. In certain instances, the polyalkylene oxide-asparaginase is present in the composition in an amount ranging from 700 to 800 IU/g. For example, the polyalkylene oxide-asparaginase may have a potency (activity) ranging from 700 to 800 IU/g. In certain instances, the polyalkylene oxide-asparaginase is present in the composition in an amount of 750 IU/g. For example, the polyalkylene oxide-asparaginase may have a potency (activity) of 750 IU/g.

In some cases, the polyalkylene oxide-asparaginase in the composition is present in a therapeutically effective amount, where the polyalkylene oxide-asparaginase has a specific activity of 50 IU/mg protein or more, such as 55 IU/mg protein or more, or 60 IU/mg protein or more, or 65 IU/mg protein or more, or 70 IU/mg protein or more, or 75 IU/mg protein or more, or 80 IU/mg protein or more, or 85 IU/mg protein or more, or 90 IU/mg protein or more, or 95 IU/mg protein or more, or 100 IU/mg protein or more, or 105 IU/mg protein or more, or 110 IU/mg protein or more, or 115 IU/mg protein or more, or 120 IU/mg protein or more, or 125 IU/mg protein or more, or 130 IU/mg protein or more, or 135 IU/mg protein or more, or 140 IU/mg protein or more, or 145 IU/mg protein or more, or 150 IU/mg protein or more. For instance, the polyalkylene oxide-asparaginase in the composition may have a specific activity of 85 IU/mg protein or more. In some embodiments, the polyalkylene oxide-asparaginase in the composition has a specific activity ranging from 50 to 150 IU/mg protein, or 55 to 145 IU/mg protein, or 60 to 140 IU/mg protein, or 65 to 135 IU/mg protein, or 70 to 130 IU/mg protein, or 75 to 125 IU/mg protein, or 80 to 120 IU/mg protein, or 85 to 115 IU/mg protein, or 90 to 110 IU/mg protein, or 95 to 105 IU/mg protein. In some cases, the polyalkylene oxide-asparaginase in the composition has a specific activity ranging from 50 to 150 IU/mg protein, such as 65 to 140 IU/mg protein, or 70 to 135 IU/mg protein, or 75 to 130 IU/mg protein, or 75 to 125 IU/mg protein. For instance, the polyalkylene oxide-asparaginase in the composition may have a specific activity ranging from 75 to 125 IU/mg protein.

In certain embodiments, the polyalkylene oxide-asparaginase in the composition is present in a therapeutically effective amount, where the polyalkylene oxide-asparaginase in the composition is present in an amount ranging from 1 mg/mL to 15 mg/mL, such as 1.5 mg/mL to 14.5 mg/mL, or 2 mg/mL to 14 mg/mL, or 2.5 mg/mL to 13.5 mg/mL, or 3 mg/mL to 13 mg/mL, or 3.5 mg/mL to 12.5 mg/mL, or 4 mg/mL to 12 mg/mL, or 4.5 mg/mL to 11.5 mg/mL, or 4.5 mg/mL to 11 mg/mL, or 4.5 mg/mL to 10.5 mg/mL, or 4.5 mg/mL to 10 mg/mL, or 4.5 mg/mL to 9.5 mg/mL, or 4.5 mg/mL to 9 mg/mL, or 4.5 mg/mL to 8.5 mg/mL, or 5 mg/mL to 8 mg/mL. In some cases, the polyalkylene oxide-asparaginase in the composition is present in an amount ranging from 4.5 mg/mL to 8.5 mg/mL.

When administered to a subject, the composition may include an amount of the polyalkylene oxide-asparaginase sufficient to deliver from 100 to 5,000 IU/m$^2$ of the polyalkylene oxide-asparaginase to the subject, such as from 500 to 5,000 IU/m$^2$, or 500 to 4,500 IU/m$^2$, or 500 to 4,000 IU/m$^2$, or 500 to 3,500 IU/m$^2$, or 500 to 3,000 IU/m$^2$, or 1,000 to 3,000 IU/m$^2$, or 1,500 to 3,000 IU/m$^2$, or 1,750 to 3,000 IU/m$^2$, or 2,000 to 3,000 IU/m$^2$, or 2,000 to 2,750 IU/m$^2$, or 2,250 to 2,750 IU/m$^2$ of the polyalkylene oxide-asparaginase to the subject. For example, the composition may include an amount of the polyalkylene oxide-asparaginase sufficient to deliver from 1,500 to 3,000 IU/m$^2$ of the polyalkylene oxide-asparaginase to the subject. In certain instances, the composition includes an amount of the polyalkylene oxide-asparaginase sufficient to deliver from 2,000 to 2,750 IU/m$^2$ of the polyalkylene oxide-asparaginase to the subject. In certain instances, the composition includes an amount of the polyalkylene oxide-asparaginase sufficient to deliver from 2,250 to 2,750 IU/m$^2$ of the polyalkylene oxide-asparaginase to the subject. For instance, the composition may include an amount of the polyalkylene oxide-asparaginase sufficient to deliver 2,500 IU/m$^2$ of the polyalkylene oxide-asparaginase to the subject.

In certain embodiments, the dosage administered to the subject is a liquid dosage, for example, an aqueous dosage. In some embodiments, in addition to the polyalkylene oxide-asparaginase, the dosage includes a buffer and a salt.

The compositions of the present disclosure, in addition to the polyalkylene oxide-asparaginase, may include additional components. For instance, the composition may include a buffer. Buffers suitable for use in the compositions of the present disclosure include buffers that are compatible with the polyalkylene oxide-asparaginase and suitable for administration to a subject, e.g., by injection or intravenous administration. Examples of suitable buffers include, but are not limited to, phosphate buffers (e.g., phosphate buffered saline (PBS)), Dulbecco's phosphate buffered saline (DPBS), Hank's balanced salt solution (HBSS), Earle's balanced salt solution (EBSS), Tris buffer, Ringer's lactate buffer, and the like, and combinations thereof. The buffer included in the composition may be a buffer that maintains the pH of the composition at a physiologically compatible pH, such as a pH ranging from 6 to 8, or a pH of about 7, for example 7.2, 7.3 or 7.4. In some instances, the buffer is a phosphate buffer. The phosphate buffer can include dibasic sodium phosphate (also known as disodium phosphate or sodium hydrogen phosphate; Na$_2$HPO$_4$) and/or monobasic sodium phosphate (also known as monosodium phosphate; NaH$_2$PO$_4$).

In some cases, the amount of dibasic sodium phosphate in the composition ranges from 0.05 to 5 wt. %, such as 0.1 to 4.5 wt. %, or 0.1 to 4 wt. %, or 0.1 to 3.5 wt. %, or 0.1 to 3 wt. %, or 0.1 to 2.5 wt. %, or 0.1 to 2 wt. %, or 0.1 to 1 wt. %, or 0.1 to 0.9 wt. %, or 0.1 to 0.8 wt. %, or 0.1 to 0.7 wt. %, or 0.1 to 0.6 wt. %, or 0.2 to 0.6 wt. %, or 0.3 to 0.6 wt. %, or 0.4 to 0.6 wt. %, or 0.5 to 0.6 wt. %. For instance, the dibasic sodium phosphate may be present in the composition in an amount ranging from 0.1 to 1.0 wt. %. In certain instances, the dibasic sodium phosphate may be present in the composition in an amount ranging from 0.2 to 0.8 wt. %. In certain instances, the dibasic sodium phosphate may be present in the composition in an amount ranging from 0.3 to 0.6 wt. %. In certain instances, the dibasic sodium phosphate may be present in the composition in an amount ranging from 0.5 to 0.6 wt. %. For instance, the dibasic sodium phosphate may be present in the composition in an amount of about 0.6 wt. %, such as 0.56 wt. % (or 0.558 wt. %). In certain embodiments, the amount of monobasic sodium phosphate in the composition ranges from 0.005 to 2 wt. %, such as 0.01 to 1.8 wt. %, or 0.01 to 1.6 wt. %, or 0.01 to 1.4 wt. %, or 0.01 to 1.2 wt. %, or 0.01 to 1.0 wt. %, or 0.01 to 0.8 wt. %, or 0.01 to 0.6 wt. %, or 0.01 to 0.4 wt. %, or 0.01 to 0.2 wt. %, or 0.02 to 0.18 wt. %, or 0.03 to 0.16 wt. %, or 0.04 to 0.16 wt. %, or 0.045 to 0.15 wt. %, or 0.04 to 0.14 wt. %, or 0.05 to 0.14 wt. %, or 0.1 to 0.2 wt. %, or 0.1 to 0.15 wt. %. For instance, the monobasic sodium phosphate may be present in the composition in an amount ranging from 0.05 to 0.2 wt. %. In certain instances, the monobasic sodium phosphate may be present in the composition in an amount ranging from 0.01 to 0.2 wt. %. In certain instances, the monobasic sodium phosphate may be present in the composition in an amount ranging from 0.09 to 0.15 wt. %. In certain instances, the monobasic sodium phosphate may be present in the composition in an amount ranging from 0.1 to 0.2 wt. %. In certain instances, the monobasic sodium phosphate may be present in the composition in an amount ranging from 0.1 to 0.15 wt. %. For instance, the monobasic sodium phosphate may be present in the composition in an amount of 0.12 wt. % (or 0.129 wt. %).

Another additional component that may be included in the compositions of the present disclosure is a salt. Salts suitable for use in the compositions of the present disclosure include salts that are compatible with the polyalkylene oxide-asparaginase and suitable for administration to a subject, e.g., by injection or intravenous administration. Examples of suitable salts include, but are not limited to, sodium chloride, potassium chloride, calcium chloride, magnesium chloride, and the like, and combinations thereof. In certain instances, the salt is sodium chloride.

In some cases, the amount of salt (e.g., sodium chloride) in the composition ranges from 0.05 to 5 wt. %, such as 0.05 to 4 wt. %, or 0.05 to 3 wt. %, or 0.05 to 2 wt. %, or 0.1 to 5 wt. %, or 0.1 to 4 wt. %, or 0.1 to 3 wt. %, or 0.1 to 2 wt. %, or 0.1 to 1.5 wt. %, or 0.1 to 1 wt. %, or 0.2 to 1 wt. %, or 0.3 to 1 wt. %, or 0.4 to 1 wt. %, or 0.5 to 1 wt. %, or 0.6 to 1 wt. %, or 0.7 to 1 wt. %, or 0.8 to 1 wt. %, or 0.8 to 0.9 wt. %. For instance, the salt (e.g., sodium chloride) may be present in the composition in an amount ranging from 0.5 to 1 wt. %. For instance, the salt (e.g., sodium chloride) may be present in the composition in an amount ranging from 0.2 to 2 wt. %. In certain instances, the salt (e.g., sodium chloride) may be present in the composition in an amount ranging from 0.7 to 1 wt. %. In certain instances, the salt (e.g., sodium chloride) may be present in the composition in an amount ranging from 0.8 to 0.9 wt. %. For instance, the salt (e.g., sodium chloride) may be present in the composition in an amount of 0.85 wt. %.

In certain embodiments, the polyalkylene oxide-asparaginase containing composition is a lyophilized composition. Lyophilized compositions of the present disclosure, in addition to the polyalkylene oxide-asparaginase, may also include a buffer, a salt, and a sugar. For example, aspects of the present disclosure include a lyophilized storage stable composition of a polyalkylene oxide-asparaginase that includes a polyalkylene oxide group covalently linked by a linker to an asparaginase, a buffer, a salt, and a sugar.

Buffers suitable for use in the lyophilized compositions of the present disclosure include buffers that are compatible with the polyalkylene oxide-asparaginase and suitable for administration to a subject, e.g., by injection or intravenous administration. Examples of suitable buffers include those described above. In some instances, the buffer is a phosphate buffer. In certain embodiments, the phosphate buffer may include dibasic sodium phosphate and monobasic sodium phosphate. In some cases, the amount of dibasic sodium phosphate in the composition ranges from 0.05 to 1 wt. %, such as 0.1 to 0.9 wt. %, or 0.1 to 0.8 wt. %, or 0.1 to 0.7 wt. %, or 0.1 to 0.6 wt. %, or 0.1 to 0.5 wt. %, or 0.1 to 0.4 wt. %, or 0.2 to 0.4 wt. %, or 0.2 to 0.3 wt. %, or 0.25 to 0.3 wt. %. For instance, the dibasic sodium phosphate may be present in the composition in an amount ranging from 0.1 to 0.5 wt. %. In certain instances, the dibasic sodium phosphate may be present in the composition in an amount ranging from 0.2 to 0.4 wt. %. In certain instances, the dibasic sodium phosphate may be present in the composition in an amount ranging from 0.25 to 0.3 wt. %. For instance, the dibasic sodium phosphate may be present in the composition in an amount of about 0.3 wt. %, such as 0.28 wt. % (or 0.279 wt. %). In certain embodiments, the amount of monobasic sodium phosphate in the composition ranges from 0.005 to 1 wt. %, such as 0.01 to 0.9 wt. %, or 0.01 to 0.8 wt. %, or 0.01 to 0.7 wt. %, or 0.01 to 0.6 wt. %, or 0.01 to 0.5 wt. %, or 0.01 to 0.4 wt. %, or 0.01 to 0.3 wt. %, or 0.01 to 0.2 wt. %, or 0.01 to 0.1 wt. %, or 0.02 to 0.09 wt. %, or 0.03 to 0.08 wt. %, or 0.04 to 0.08 wt. %, or 0.045 to 0.075 wt. %, or 0.04 to 0.07 wt. %, or 0.05 to 0.07 wt. %. For instance, the monobasic sodium phosphate may be present in the composition in an amount ranging from 0.01 to 0.1 wt. %. In certain instances, the monobasic sodium phosphate may be present in the composition in an amount ranging from 0.05 to 0.07 wt. %. In certain instances, the monobasic sodium phosphate may be present in the composition in an amount ranging from 0.045 to 0.075 wt. %. For instance, the monobasic sodium phosphate may be present in the composition in an amount of 0.06 wt. %.

In certain aspects, lyophilized compositions of the present disclosure include a salt. Salts suitable for use in the compositions of the present disclosure include salts that are compatible with the polyalkylene oxide-asparaginase and suitable for administration to a subject, e.g., by injection or intravenous administration. Examples of suitable salts include those described above. In certain instances, the salt is sodium chloride.

In some cases, the amount of salt (e.g., sodium chloride) in the composition ranges from 0.05 to 1 wt. %, such as 0.1 to 0.9 wt. %, or 0.1 to 0.8 wt. %, or 0.1 to 0.7 wt. %, or 0.1 to 0.6 wt. %, or 0.1 to 0.5 wt. %, or 0.2 to 0.5 wt. %, or 0.3 to 0.5 wt. %, or 0.4 to 0.5 wt. %, or 0.4 to 0.45 wt. %. For instance, the salt (e.g., sodium chloride) may be present in the composition in an amount ranging from 0.1 to 1 wt. %. In certain instances, the salt (e.g., sodium chloride) may be present in the composition in an amount ranging from 0.3 to 0.5 wt. %. In certain instances, the salt (e.g., sodium chloride) may be present in the composition in an amount ranging from 0.4 to 0.45 wt. %. For instance, the salt (e.g., sodium chloride) may be present in the composition in an amount of about 0.4 wt. %, such as 0.425 wt. %. Another component that may be included in the compositions of the present disclosure is a sugar. Sugars suitable for use in the compositions of the present disclosure include sugars that are compatible with the polyalkylene oxide-asparaginase and suitable for administration to a subject, e.g., by injection or intravenous administration. Examples of suitable sugars include, but are not limited to, sucrose, mannitol, maltose, trehalose, 2-hydroxypropyl-beta-cyclodextrin (-HPCD), lactose, glucose, fructose, galactose, glucosamine, and the like, and combinations thereof. In certain instances, the sugar is a disaccharide. For example, the disaccharide may be sucrose.

In some cases, the amount of sugar (e.g., sucrose) in the composition ranges from 0.1 to 25 wt. %, such as 0.5 to 20 wt. %, or 1 to 15 wt. %, or 1 to 10 wt. %, or 1 to 9 wt. %, or 1 to 8 wt. %, or 2 to 7 wt. %, or 2 to 6 wt. %, or 3 to 5 wt. %, or 4 to 5 wt. %. For instance, the sugar (e.g., sucrose) may be present in the composition in an amount ranging from 1 to 10 wt. %. In certain instances, the sugar (e.g., sucrose) may be present in the composition in an amount ranging from 3 to 5 wt. %. In certain instances, the sugar (e.g., sucrose) may be present in the composition in an amount ranging from 4 to 5 wt. %. For instance, the sugar (e.g., sucrose) may be present in the composition in an amount of 4.5 wt. %.

In some embodiments, the composition comprises, consists essentially of, or consists of a polyalkylene oxide-asparaginase having a potency (activity) ranging from 500 to 1,000 IU/g, dibasic sodium phosphate in an amount ranging from 0.1 to 1.0 wt. %, monobasic sodium phosphate in an amount ranging from 0.01 to 0.2 wt. %, a salt (e.g., sodium chloride) in an amount ranging from 0.2 to 2 wt. %, and water.

In some embodiments, the composition comprises, consists essentially of, or consists of a polyalkylene oxide-asparaginase having a potency (activity) ranging from 700 to 800 IU/g, dibasic sodium phosphate in an amount ranging from 0.2 to 0.8 wt. %, monobasic sodium phosphate in an amount ranging from 0.1 to 0.14 wt. %, a salt (e.g., sodium chloride) in an amount ranging from 0.6 to 1.0 wt. %, and water.

In some embodiments, the composition comprises, consists essentially of, or consists of a polyalkylene oxide-asparaginase having a potency (activity) ranging from 700 to 800 IU/g, dibasic sodium phosphate in an amount ranging from 0.5 to 0.6 wt. %, monobasic sodium phosphate in an amount ranging from 0.09 to 0.15 wt. %, a salt (e.g., sodium chloride) in an amount ranging from 0.8 to 0.9 wt. %, and water.

In some embodiments, the composition comprises, consists essentially of, or consists of a polyalkylene oxide-asparaginase having a potency (activity) of 750 IU/g, dibasic sodium phosphate in an amount of about 0.6 wt. %, monobasic sodium phosphate in an amount of about 0.1 wt. %, a salt (e.g., sodium chloride) in an amount of about 0.9 wt. %, and water.

In some embodiments, the composition comprises, consists essentially of, or consists of a polyalkylene oxide-asparaginase having a potency (activity) of 750 IU/g, dibasic sodium phosphate in an amount of 0.56 wt. % (or 0.558 wt. %), monobasic sodium phosphate in an amount of 0.13 wt.

% (or 0.129 wt. %), a salt (e.g., sodium chloride) in an amount of 0.85 wt. %, and water.

In some embodiments, the composition comprises, consists essentially of, or consists of a polyalkylene oxide-asparaginase, dibasic sodium phosphate, monobasic sodium phosphate, salt (e.g., sodium chloride), and water. In other embodiments, the composition comprises, consists essentially of, or consists of a polyalkylene oxide-asparaginase, dibasic sodium phosphate, monobasic sodium phosphate, salt (e.g., sodium chloride), sugar (e.g., sucrose), and water.

In some embodiments, the composition comprises, consists essentially of, or consists of a polyalkylene oxide-asparaginase having a potency (activity) ranging from 500 to 1,000 IU/g, dibasic sodium phosphate in an amount ranging from 0.1 to 0.5 wt. %, monobasic sodium phosphate in an amount ranging from 0.01 to 0.1 wt. %, a salt (e.g., sodium chloride) in an amount ranging from 0.1 to 1 wt. %, a sugar (e.g., sucrose) in an amount ranging from 1 to 10 wt. %, and water.

In some embodiments, the composition comprises, consists essentially of, or consists of a polyalkylene oxide-asparaginase having a potency (activity) ranging from 700 to 800 IU/g, dibasic sodium phosphate in an amount ranging from 0.2 to 0.4 wt. %, monobasic sodium phosphate in an amount ranging from 0.05 to 0.07 wt. %, a salt (e.g., sodium chloride) in an amount ranging from 0.3 to 0.5 wt. %, a sugar (e.g., sucrose) in an amount ranging from 3 to 5 wt. %, and water.

In some embodiments, the composition comprises, consists essentially of, or consists of a polyalkylene oxide-asparaginase having a potency (activity) ranging from 700 to 800 IU/g, dibasic sodium phosphate in an amount ranging from 0.25 to 0.3 wt. %, monobasic sodium phosphate in an amount ranging from 0.045 to 0.075 wt. %, a salt (e.g., sodium chloride) in an amount ranging from 0.4 to 0.45 wt. %, a sugar (e.g., sucrose) in an amount ranging from 4 to 5 wt. %, and water.

In some embodiments, the composition comprises, consists essentially of, or consists of a polyalkylene oxide-asparaginase having a potency (activity) of 750 IU/g, dibasic sodium phosphate in an amount of about 0.3 wt. %, monobasic sodium phosphate in an amount of about 0.06 wt. %, a salt (e.g., sodium chloride) in an amount of about 0.4 wt. %, a sugar (e.g., sucrose) in an amount of about 4.5 wt. %, and water.

In some embodiments, the composition comprises, consists essentially of, or consists of a polyalkylene oxide-asparaginase having a potency (activity) of 750 IU/g, dibasic sodium phosphate in an amount of 0.28 wt. % (or 0.279 wt. %), monobasic sodium phosphate in an amount of 0.06 wt. %, a salt (e.g., sodium chloride) in an amount of 0.43 wt. % (or 0.425 wt. %), a sugar (e.g., sucrose) in an amount of 4.5 wt. %, and water.

In certain instances, the composition (e.g., liquid or lyophilized composition) is a sterile composition. By "sterile" is meant that there are substantially no immunogenic components in the composition, such as for example substantially no microbes (e.g., fungi, bacteria, viruses, spore forms, etc.). In some cases, the composition is present in a container. Providing the composition in a container may facilitate maintaining the composition as a sterile composition. For instance, the container may be configured to maintain the composition enclosed in the container in a sterile environment. As such, the container may be a sealed container, for example the container may include a seal, such as a water-tight and/or an air-tight seal. The seal may be removable from the container to allow a user access to the contents of the container. In some instances, the seal may be a frangible seal, or in other instances, the seal may be configured to allow insertion of a needle, cannula or syringe into the interior of the container without removing the seal from the container. In some cases, a seal configured to allow access to the interior of the container without removing the seal from the container may facilitate maintaining the contents of the container (e.g., the composition in the container) in a sterile environment prior to administration of the composition to a subject. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

In some cases, the container is a unit dosage container. A unit dosage container refers to a container that contains one or more unitary dosages for administration to a subject. In some embodiments, a unit dosage container includes a predetermined quantity of a subject composition calculated in an amount sufficient to produce a desired effect in a subject. Certain embodiments of the compositions may be provided in a unit dosage container suitable for individual administration of precise dosages. The amount of active composition administered to a subject may depend on the subject being treated, the severity of the affliction, and the manner of administration. For example, the unit dosage container may contain a quantity of the composition to be administered as disclosed herein in an amount effective to achieve the desired effect in the subject being treated. In certain instances, a unit dosage container includes a composition having a polyalkylene oxide-asparagine in a therapeutically effective amount. Therapeutically effective amounts of the polyalkylene oxide-asparagine are described above. In certain embodiments, the unit dosage container is a vial. In some cases, the vial is a sealed vial (e.g., as described above regarding a sealed container).

The container may be composed of any convenient material that is compatible with the polyalkylene oxide-asparaginase and other components of the composition. For example, the container can be a solid-compatible container configured to contain a solid (e.g., a lyophilized composition). In some instances, the container is a liquid-compatible container configured to contain a liquid. Containers may also be solid and liquid compatible, where the container is configured to contain solids and liquids. In some cases, a liquid in the container may be an aqueous liquid, and in these cases, the container may be compatible with aqueous compositions. By "compatible" is meant that the container is substantially inert (e.g., does not significantly react with) the liquid and/or compositions or other components in contact with the container. Examples of suitable container materials include, but are not limited to, glass and plastic. For example, the container may be composed of glass, such as, but not limited to, silicate glass, borosilicate glass, sodium borosilicate glass (e.g., PYREX™), fused quartz glass, fused silica glass, and the like. Other examples of suitable container materials for the container include plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), polystyrene, and the like. In certain instances, as described above, the container is a vial, and as such may be a glass vial. As described above, the container may be a sealed container, and as such may be a sealed glass vial.

As described in more detail below, liquid or reconstituted compositions of the present disclosure may be administered to a subject, for example by injection or intravenously. In certain embodiments, prior to administration of the reconstituted composition to a subject, a solid composition, e.g., as described above, may be combined with a liquid to provide a liquid composition suitable for administration, for example by injection or intravenously. In some cases, prior to administration of the composition to a subject, a solid composition may be combined with water (e.g., water for injection, WFI) to provide an aqueous composition suitable for administration, for example by injection or intravenously. For instance, a lyophilized composition may be reconstituted with water (e.g., water for injection, WFI) to produce a reconstituted dosage unit suitable for administration to a subject, for example by injection or intravenously.

As set forth herein, aspects of the present disclosure include a composition that includes: a polyalkylene oxide-asparaginase that includes a polyalkylene oxide group covalently linked by a linker to an asparaginase; a buffer and a salt. In certain embodiments, as described above, the polyalkylene oxide is a polyethylene glycol. In certain embodiments, as described above, the linker is a urethane (carbamate) linker. In certain embodiments, as described above, the asparaginase is an *E. coli* asparaginase. In certain embodiments, as described above, the buffer is a phosphate buffer. In certain embodiments, as described above, the salt is sodium chloride. Accordingly, certain embodiments of the composition include a polyethylene glycol-asparaginase that includes a polyethylene glycol group covalently linked by a urethane linker to an *E. coli* asparaginase; a phosphate buffer and a salt. Each of the components of these compositions (e.g., molecular weight of polyethylene glycol, amount of polyethylene glycol-asparaginase, amount and type of phosphate buffer, amount and type of salt) is as described in detail above.

As set forth herein, aspects of the present disclosure include a lyophilized storage stable composition that includes: a polyalkylene oxide-asparaginase that includes a polyalkylene oxide group covalently linked by a linker to an asparaginase; a buffer, a salt and a sugar. In certain embodiments, as described above, the polyalkylene oxide is a polyethylene glycol. In certain embodiments, as described above, the linker is a urethane (carbamate) linker. In certain embodiments, as described above, the asparaginase is an *E. coli* asparaginase. In certain embodiments, as described above, the buffer is a phosphate buffer. In certain embodiments, as described above, the salt is sodium chloride. In certain embodiments, as described above, the sugar is a disaccharide (e.g., sucrose). Accordingly, certain embodiments of the lyophilized storage stable composition include a polyethylene glycol-asparaginase that includes a polyethylene glycol group covalently linked by a urethane linker to an *E. coli* asparaginase; a phosphate buffer, a salt and a disaccharide. Each of the components of these compositions (e.g., molecular weight of polyethylene glycol, amount of polyethylene glycol-asparaginase, amount and type of phosphate buffer, amount and type of salt, amount and type of disaccharide, etc.) is as described in detail above.

Compositions of the present disclosure may also include other components, such as additional pharmaceutically acceptable excipients or a dosage delivery vehicle as part of the composition. Excipients may include, but are not limited to, carbohydrates, inorganic salts, organic salts, antimicrobial agents, antioxidants, surfactants, water (e.g., water for injection (WFI)), alcohols, polyols, glycerine, vegetable oils, phospholipids, buffers, acids, bases, and any combinations thereof. A carbohydrate such as a sugar, a derivatized sugar such as an alditol, aldonic acid, an esterified sugar, and/or a sugar polymer may also be employed. Some carbohydrate excipients of interest include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. Inorganic and organic salts may include, but are not limited to citric acid, sodium chloride, potassium chloride, sodium sulfate, potassium nitrate, monobasic sodium phosphate, dibasic sodium phosphate, and any combinations thereof.

In certain embodiments, compositions of the present disclosure may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be included in the composition. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and any combinations thereof.

One or more surfactants may also be included in compositions of the present disclosure. For example, suitable surfactants may include, but are not limited to polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines, fatty acids and fatty esters; steroids, such as cholesterol; chelating agents, such as EDTA; and zinc and other cations.

Acids or bases may also be present in compositions of the present disclosure. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples of bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the composition may vary depending on the nature and function of the excipient, dosage delivery vehicle and particular needs of the composition. In some instances, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of 1% to 99% by weight, such as from 5% to 98% by weight, such as from 15% to 95% by weight of the excipient, including 30% or less by weight, or 20% or less by weight, or 10% or less by weight. Pharmaceutical excipients along with other excipients that may be employed in the compositions are described in "Remington: The Science & Practice of Pharmacy", 22nd ed., Williams & Williams, (2012), the "Physician's Desk Reference", 70th ed., PDR Network, Montvale, NJ (2015), and Rowe, R C., Handbook of Pharmaceutical Excipients, 7th ed., Pharmaceutical Press, New York, NY, (2012), the disclosures of each of which are incorporated herein by reference.

Methods of Use

Aspects of the present disclosure also include methods of using the compositions (e.g., liquid and lyophilized) described herein. In certain embodiments, the method of use is a method of deaminating asparagine in a subject. As described above, the asparaginase enzyme can mediate a deamination reaction where the amino acid asparagine is hydrolyzed to produce aspartate and ammonia, e.g., according to the following reaction:

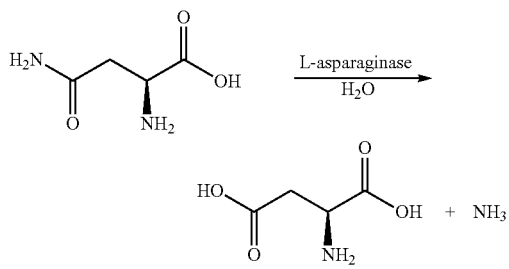

In some cases, the activity of asparaginase reduces the concentration of asparagine in a subject, such as reduces the plasma concentration of asparagine in the subject. A depletion of asparagine in a subject may adversely affect cells in the subject that depend on the presence of asparagine for protein synthesis. For example, protein synthesis in cells that lack the ability to synthesize their own asparagine (e.g., cells that lack the enzyme asparagine synthetase) may be adversely affected by a lack of exogenous asparagine, which in turn may lead to apoptosis of the cells. In some instances, cells in a subject that depend on the presence of asparagine for protein synthesis may be associated with a neoplastic condition, such as a cancer. Accordingly, methods of the present disclosure include methods for treating a subject for a neoplastic condition, such as methods of treating a subject for a cancer. Accordingly, compositions of the present disclosure that include a polyalkylene oxide-asparaginase may be therapeutically effective for the treatment of neoplastic conditions, such as a cancer. In certain embodiments, non-neoplastic cells in the subject are not significantly affected by the polyalkylene oxide-asparaginase compositions of the present disclosure. For instance, non-neoplastic cells in the subject may have the enzyme asparagine synthetase, and thus retain the ability to synthesize asparagine.

In certain embodiments, the neoplastic condition to be treated in the subject includes neoplastic conditions that are amenable to treatment by administration of a polyalkylene oxide-asparaginase to the subject, e.g., neoplastic conditions that depend on exogenous asparagine. For example, neoplastic conditions that may be treated by administering a polyalkylene oxide-asparaginase to a subject include cancers, such as solid tumors or liquid tumors.

In certain cases, the neoplastic condition is characterized by the presence of a solid tumor. Accordingly, in some embodiments, a method of the present disclosure is a method of treating a subject for a solid tumor using a polyalkylene oxide-asparaginase (e.g., liquid or a reconstituted lyophilized polyalkylene oxide-asparaginase composition of the present disclosure). Methods of treating a subject for a neoplastic condition are useful for treating a wide variety of solid tumors, including carcinomas and sarcomas. Types of solid tumors may include, but are not limited to, pancreatic cancer, melanoma, squamous cell cancer, non-squamous cell lung cancer (NSCLC), colon cancer, breast cancer, ovarian cancer, cervical cancer, prostate cancer, and the like. For example, carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In certain cases, the neoplastic condition is characterized by the presence of a liquid tumor. For instance, a liquid tumor may include metastatic cancer cells (e.g., circulating tumor cells (CTC)), blood cancers, and the like, and combinations thereof. Examples of blood cancers include, but are not limited to, leukemia, lymphoma and myeloma. In some instances, the cancer is leukemia. Accordingly, in some embodiments, the method is a method of treating a subject for leukemia using a polyalkylene oxide-asparaginase (e.g., liquid or a reconstituted lyophilized polyalkylene oxide-asparaginase composition of the present disclosure).

Various types of leukemia may be amenable to treatment using the subject methods. For example, the leukemia may be an acute leukemia. An acute leukemia may be characterized by a rapid increase in the number of immature blood cells. A rapid increase in immature blood cells may result in crowding, which in turn may cause the bone marrow to produce significantly less healthy blood cells. Thus, methods of the present disclosure include methods for treating a subject for acute leukemia, e.g., by administering to the subject a dosage of a polyalkylene oxide-asparaginase (e.g., liquid or a reconstituted lyophilized polyalkylene oxide-asparaginase composition of the present disclosure) effective to treat the subject for acute leukemia.

In other instances, the leukemia is a chronic leukemia. In some cases, chronic leukemia may be characterized by an increase in the number of relatively mature, but abnormal, white blood cells. Chronic leukemia may take an extended period of time to develop (e.g., months or years), where the abnormal white blood cells are produced at a significantly higher rate than normal. Thus, methods of the present disclosure include methods for treating a subject for chronic leukemia, e.g., by administering to the subject a dosage of a polyalkylene oxide-asparaginase (e.g., liquid or a reconstituted lyophilized polyalkylene oxide-asparaginase composition of the present disclosure) effective to treat the subject for chronic leukemia.

In certain embodiments, the leukemia is a lymphoblastic leukemia (also referred to as lymphocytic leukemia). A lymphoblastic leukemia may be characterized by the type of blood cell affected by the leukemia. In lymphoblastic leukemia the abnormal change in the blood cells takes place in bone marrow cells that normally develop into lymphocytes. For example, lymphoblastic leukemia may be B-cell leukemia. Thus, methods of the present disclosure include methods for treating a subject for lymphoblastic leukemia (lymphocytic leukemia), e.g., by administering to the subject a dosage of a polyalkylene oxide-asparaginase (e.g., liquid or a reconstituted lyophilized polyalkylene oxide-asparaginase composition of the present disclosure) effective to treat the subject for lymphoblastic leukemia (lymphocytic leukemia). For example, a specific type of lymphoblastic leukemia that may be treated using the subject methods includes acute lymphoblastic leukemia (ALL). In these embodiments, methods of the present disclosure include methods for treating a subject for acute lymphoblastic leukemia (ALL), e.g., by administering to the subject a dosage of a polyalkylene oxide-asparaginase (e.g., liquid or a reconstituted lyophilized polyalkylene oxide-asparaginase composition of the present disclosure) effective to treat the subject for ALL. Other types of lymphoblastic leukemia that may be treated using the subject methods include, but are not limited to, chronic lymphocytic leukemia (CLL). In these embodiments, methods of the present disclosure include methods for treating a subject for chronic lymphocytic leukemia (CLL), e.g., by administering to the subject a dosage of a polyalkylene oxide-asparaginase (e.g., liquid or a reconstituted lyophilized polyalkylene oxide-asparaginase composition of the present disclosure) effective to treat the subject for CLL.

In other embodiments, the leukemia is a myeloid leukemia (also referred to as myelogenous leukemia). A myeloid leukemia may be characterized by the type of blood cell affected by the leukemia. In myeloid leukemia the abnormal change in the blood cells takes place in bone marrow cells that normally develop into red blood cells and/or platelets. Thus, methods of the present disclosure include methods for treating a subject for myeloid leukemia (myelogenous leukemia), e.g., by administering to the subject a dosage of a polyalkylene oxide-asparaginase (e.g., liquid or a reconstituted lyophilized polyalkylene oxide-asparaginase composition of the present disclosure) effective to treat the subject for myeloid leukemia (myelogenous leukemia). For example, a specific type of myeloid leukemia that may be treated using the subject methods includes acute myeloid leukemia (AML). In these embodiments, methods of the present disclosure include methods for treating a subject for acute myeloid leukemia (AML), e.g., by administering to the subject a dosage of a polyalkylene oxide-asparaginase (e.g., liquid or a reconstituted lyophilized polyalkylene oxide-asparaginase composition of the present disclosure) effective to treat the subject for AML.

Examples of AML include, but are not limited to, AMLs with recurrent cytogenetic translocations, AML with multilineage dysplasia, and other AMLs. For instance, AMLs with recurrent cytogenetic translocations include, among others, AML with t(8;21)(q22;q22), AML1 (CBF-alpha)/ETO, Acute promyelocytic leukemia (AML with t(15; 17)(q22;q11-12) and variants, PML/RAR-alpha), AML with abnormal bone marrow eosinophils (inv(16)(p13q22) or t(16;16)(p13;q11), CBFb/MYH1 IX), and AML with 11q23 (MLL) abnormalities. Examples of AML with multilineage dysplasia may include those that are associated with or without prior myelodysplastic syndrome. Other types of acute myeloid leukemia include, for example, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

Other types of myeloid leukemia that may be treated using the subject methods include, but are not limited to, chronic myelogenous leukemia (CML). In these embodiments, methods of the present disclosure include methods for treating a subject for chronic myelogenous leukemia (CML), e.g., by administering to the subject a dosage of a polyalkylene oxide-asparaginase (e.g., liquid or a reconstituted lyophilized polyalkylene oxide-asparaginase composition of the present disclosure) effective to treat the subject for CIVIL.

In certain cases, asparaginase can mediate the deamination of glutamine, where the amino acid glutamine is hydrolyzed to produce glutamate and ammonia, e.g., according to the following reaction:

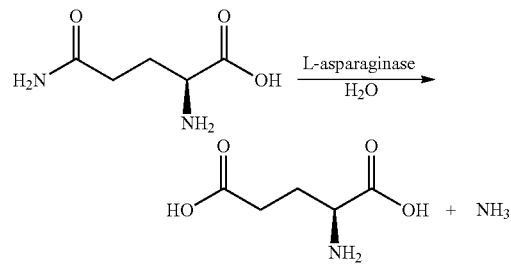

In some cases, the activity of asparaginase reduces the concentration of glutamine in a subject, such as reduces the plasma concentration of glutamine in the subject. Similar to the discussion above, a depletion of glutamine in a subject may adversely affect cells in the subject that depend on the presence of glutamine for protein synthesis. For example, protein synthesis in cells that lack the ability to synthesize their own glutamine (e.g., cells that lack the enzyme glutamine synthetase) may be adversely affected by a lack of exogenous glutamine, which in turn may lead to apoptosis of the cells. In some instances, cells in a subject that depend on the presence of glutamine for protein synthesis may be associated with a neoplastic condition, such as a cancer.

Accordingly, methods of the present disclosure include methods for treating a subject for a neoplastic condition, such as methods of treating a subject for a cancer, where the neoplastic condition may depend on exogenous glutamine. For example, embodiments of the subject methods include methods of deaminating glutamine in a subject. In certain embodiments, non-neoplastic cells in the subject are not significantly affected by the polyalkylene oxide-asparaginase administered to the subject. For instance, non-neoplastic cells in the subject may have the enzyme glutamine synthetase, and thus retain the ability to synthesize glutamine.

As described above, compositions of the present disclosure include lyophilized storage stable compositions. Prior to administration of the composition to a subject, a lyophilized composition may be combined with a liquid to provide a liquid composition suitable for administration, for example by injection or intravenously. In some cases, prior to administration of the composition to a subject, a lyophilized composition is combined with water (e.g., water for injection, WFI) to provide an aqueous composition suitable for administration, for example by injection or intravenously. For instance, methods of the present disclosure may include reconstituting a lyophilized composition (e.g., a lyophilized storage stable composition) of the present disclosure. Reconstituting a lyophilized composition may produce a reconstituted dosage unit. In some cases, the reconstituted dosage unit is suitable for administration to the subject, for example by injection or intravenously. In certain embodiments, reconstituting the lyophilized composition includes combining the lyophilized composition (e.g., the lyophilized storage stable composition) with water (e.g., water for injection, WFI).

The liquid or reconstituted dosage unit may include a predetermined quantity of the composition of the present disclosure calculated in an amount sufficient to produce a desired therapeutic effect in a subject. The amount of the composition in a dosage unit (e.g., liquid or reconstituted) that is administered to a subject may depend on the subject being treated, the severity of the affliction, and the manner of administration. For example, the dosage unit may include a quantity of the composition to be administered as disclosed herein in a therapeutically effective amount.

Certain embodiments of the dosage unit may include an amount of the polyalkylene oxide-asparaginase ranging from 100 to 5,000 IU/mL, such as 500 to 4,500 IU/mL, or 500 to 4,000 IU/mL, or 500 to 3,500 IU/mL, or 500 to 3,000 IU/mL, or 500 to 2,500 IU/mL, or 500 to 2,000 IU/mL, or 500 to 1,500 IU/mL, or 500 to 1,000 IU/mL, or 600 to 900 IU/mL, or, or 700 to 800 IU/mL. In certain instances, the dosage unit includes an amount of the polyalkylene oxide-asparaginase ranging from 500 to 1,000 IU/mL. In certain instances, the dosage unit includes an amount of the polyalkylene oxide-asparaginase ranging from 700 to 800 IU/mL. For example, the dosage unit may include 750 IU/mL of the polyalkylene oxide-asparaginase.

In certain embodiments, the dosage unit includes a therapeutically effective amount (e.g., specific activity) of the polyalkylene oxide-asparaginase, such as 50 IU/mg protein or more, such as 55 IU/mg protein or more, or 60 IU/mg protein or more, or 65 IU/mg protein or more, or 70 IU/mg protein or more, or 75 IU/mg protein or more, or 80 IU/mg protein or more, or 85 IU/mg protein or more, or 90 IU/mg protein or more, or 95 IU/mg protein or more, or 100 IU/mg protein or more, or 105 IU/mg protein or more, or 110 IU/mg protein or more, or 115 IU/mg protein or more, or 120 IU/mg protein or more, or 125 IU/mg protein or more, or 130 IU/mg protein or more, or 135 IU/mg protein or more, or 140 IU/mg protein or more, or 145 IU/mg protein or more, or 150 IU/mg protein or more. For instance, the dosage unit may have a specific activity of 85 IU/mg protein or more. In some embodiments, the dosage unit has a specific activity ranging from 50 to 150 IU/mg protein, or 55 to 145 IU/mg protein, or 60 to 140 IU/mg protein, or 65 to 135 IU/mg protein, or 70 to 130 IU/mg protein, or 75 to 125 IU/mg protein, or 80 to 120 IU/mg protein, or 85 to 115 IU/mg protein, or 90 to 110 IU/mg protein, or 95 to 105 IU/mg protein. In some cases, the dosage unit has a specific activity ranging from 50 to 150 IU/mg protein, such as 65 to 140 IU/mg protein, or 70 to 135 IU/mg protein, or 75 to 130 IU/mg protein, or 75 to 125 IU/mg protein. For instance, the dosage unit may have a specific activity ranging from 75 to 125 IU/mg protein.

In certain embodiments, the dosage unit includes a therapeutically effective amount (e.g., protein concentration) of the polyalkylene oxide-asparaginase in an amount ranging from 1 mg/mL to 15 mg/mL, such as 1.5 mg/mL to 14.5 mg/mL, or 2 mg/mL to 14 mg/mL, or 2.5 mg/mL to 13.5 mg/mL, or 3 mg/mL to 13 mg/mL, or 3.5 mg/mL to 12.5 mg/mL, or 4 mg/mL to 12 mg/mL, or 4.5 mg/mL to 11.5 mg/mL, or 4.5 mg/mL to 11 mg/mL, or 4.5 mg/mL to 10.5 mg/mL, or 4.5 mg/mL to 10 mg/mL, or 4.5 mg/mL to 9.5 mg/mL, or 4.5 mg/mL to 9 mg/mL, or 4.5 mg/mL to 8.5 mg/mL, or 5 mg/mL to 8 mg/mL. In some cases, the dosage unit includes the polyalkylene oxide-asparaginase in an amount ranging from 4.5 mg/mL to 8.5 mg/mL.

When administered to a subject, the dosage unit may include a therapeutically effective amount of the polyalkylene oxide-asparaginase such that the dosage unit delivers from 100 to 5,000 IU/m$^2$ of the polyalkylene oxide-asparaginase to the subject, such as from 500 to 5,000 IU/m$^2$, or 500 to 4,500 IU/m$^2$, or 500 to 4,000 IU/m$^2$, or 500 to 3,500 IU/m$^2$, or 500 to 3,000 IU/m$^2$, or 1,000 to 3,000 IU/m$^2$, or 1,500 to 3,000 IU/m$^2$, or 1,750 to 3,000 IU/m$^2$, or 2,000 to 3,000 IU/m$^2$, or 2,000 to 2,750 IU/m$^2$, or 2,250 to 2,750 IU/m$^2$ of the polyalkylene oxide-asparaginase to the subject. For example, the dosage unit may deliver from 1,500 to 3,000 IU/m$^2$ of the polyalkylene oxide-asparaginase to the subject. In certain instances, the dosage unit delivers from 2,000 to 2,750 IU/m$^2$ of the polyalkylene oxide-asparaginase to the subject. In certain instances, the dosage unit delivers from 2,250 to 2,750 IU/m$^2$ of the polyalkylene oxide-asparaginase to the subject. For instance, the dosage unit may deliver 2,500 IU/m$^2$ of the polyalkylene oxide-asparaginase to the subject.

In certain embodiments, the dosage unit includes a buffer, such as a buffer described in detail above. For instance, the dosage unit may include a phosphate buffer, and as such may include dibasic sodium phosphate and monobasic sodium phosphate.

In some cases, the dosage unit includes a phosphate buffer, and as such may include dibasic sodium phosphate and monobasic sodium phosphate. In certain instances, the dosage unit includes dibasic sodium phosphate in an amount ranging from 0.5 to 10 mg/g, such as 1 to 9 mg/g, or 1 to 8 mg/g, or 1 to 7 mg/g, or 2 to 7 mg/g, or 3 to 6 mg/g, or 4 to 6 mg/g, or 5 to 6 mg/g. For instance, the dosage unit may include dibasic sodium phosphate in an amount ranging from 4 to 6 mg/g. In certain instances, the dosage unit includes dibasic sodium phosphate in an amount ranging from 5 to 6 mg/g. For example, the dosage unit may include dibasic sodium phosphate in an amount of about 5.5 mg/g, such as 5.6 mg/g (or 5.58 mg/g). In certain embodiments, the dosage unit includes monobasic sodium phosphate in an amount ranging from 0.05 to 5 mg/g, such as 0.1 to 4.5 mg/g, or 0.1 to 4 mg/g, or 0.1 to 3.5 mg/g, or 0.1 to 3 mg/g, or 0.1 to 2.5 mg/g, or 0.1 to 2 mg/g, or 0.5 to 2 mg/g, or 1 to 2 mg/g, or 1 to 1.5 mg/g. For instance, the dosage unit may include monobasic sodium phosphate in an amount ranging from 1 to 2 mg/g. In certain instances, the dosage unit includes monobasic sodium phosphate in an amount ranging from 1 to 1.5 mg/g. For instance, the dosage unit may include monobasic sodium phosphate in an amount of 1.2 mg/g (or 1.29 mg/g).

In certain embodiments, the dosage unit includes a salt. Salts suitable for use in the dosage unit include salts that are compatible with the polyalkylene oxide-asparaginase and suitable for administration to a subject, e.g., by injection or intravenous administration. Examples of suitable salts include, but are not limited to, sodium chloride, potassium chloride, calcium chloride, magnesium chloride, and the like, and combinations thereof.

In certain instances, the dosage unit includes a salt, such as sodium chloride. In some cases, the dosage unit includes a salt (e.g., sodium chloride) in an amount ranging from 1 to 20 mg/g, such as 1 to 19 mg/g, or 1 to 18 mg/g, or 1 to 17 mg/g, or 1 to 16 mg/g, or 1 to 15 mg/g, or 2 to 15 mg/g, or 3 to 15 mg/g, or 4 to 15 mg/g, or 5 to 14 mg/g, or 5 to 13 mg/g, or 5 to 12 mg/g, or 5 to 11 mg/g, or 5 to 10 mg/g, or 5 to 9 mg/g, or 6 to 9 mg/g, or 7 to 9 mg/g, or 8 to 9 mg/g. For instance, the dosage unit may include a salt (e.g., sodium chloride) in an amount ranging from 1 to 10 mg/g. In certain instances, the dosage unit includes a salt (e.g., sodium chloride) in an amount ranging from 5 to 10 mg/g. In certain instances, the dosage unit includes a salt (e.g., sodium chloride) in an amount ranging from 6 to 9 mg/g. In certain instances, the dosage unit includes a salt (e.g., sodium chloride) in an amount ranging from 8 to 9 mg/g. For instance, the dosage unit may include a salt (e.g., sodium chloride) in an amount of 8.5 mg/g.

In some instances, the formulation that is administered to a subject is the PEG-asparaginase liquid injection formulation known commercially as Oncaspar® which is approved for commercial marketing by the U.S. Food and Drug Administration. Oncaspar® (pegaspargase) is L-asparaginase (L-asparagine amidohydrolase) that is covalently conjugated to monomethyxoypolyethylene glycol (mPEG), which is present in a clear, colorless, preservative-free, isotonic sterile solution in phosphate-buffered saline, pH 7.3. Each milliliter contains 750±150 International Units of pegaspargase, dibasic sodium phosphate, USP (5.58 mg), monobasic sodium phosphate, USP (1.20 mg) and sodium chloride, USP (9.5 mg) in water for injection, USP.

In certain embodiments, the dosage unit administered to the subject is a dosage unit prepared from a lyophilized composition, for example a lyophilized storage stable composition as described herein. The dosage unit prepared from the lyophilized composition may be a liquid dosage. In addition to the polyalkylene oxide-asparaginase, embodiments of the dosage unit (e.g., a dosage reconstituted from a lyophilized composition) may include a buffer, a salt and a sugar.

In certain embodiments, the reconstituted dosage unit includes a buffer, such as a buffer described in detail above. In some cases, the reconstituted dosage unit includes dibasic sodium phosphate in an amount ranging from 0.5 to 10 mg/g, such as 1 to 9 mg/g, or 1 to 8 mg/g, or 1 to 7 mg/g, or 1 to 6 mg/g, or 1 to 5 mg/g, or 1 to 4 mg/g, or 2 to 4 mg/g, or 2 to 3 mg/g, or 2.5 to 3 mg/g. For instance, the reconstituted dosage unit may include dibasic sodium phosphate in an amount ranging from 1 to 5 mg/g. In certain instances, the reconstituted dosage unit may include dibasic sodium phosphate in an amount ranging from 2 to 4 mg/g. In certain instances, the reconstituted dosage unit may include dibasic sodium phosphate in an amount ranging from 2.5 to 3 mg/g. For instance, the reconstituted dosage unit may include dibasic sodium phosphate in an amount of about 3 mg/g, such as 2.8 mg/g (or 2.79 mg/g). In certain embodiments, the reconstituted dosage unit includes monobasic sodium phosphate in an amount ranging from 0.05 to 1 mg/g, such as 0.1 to 0.9 mg/g, or 0.1 to 0.8 mg/g, or 0.2 to 0.8 mg/g, or 0.3 to 0.8 mg/g, or 0.4 to 0.8 mg/g, or 0.45 to 0.75 mg/g, or 0.5 to 0.7 mg/g. For instance, the reconstituted dosage unit may include monobasic sodium phosphate in an amount ranging from 0.45 to 0.75 mg/g. In certain instances, the reconstituted dosage unit includes monobasic sodium phosphate in an amount ranging from 0.5 to 0.7 mg/g. For instance, the reconstituted dosage unit may include monobasic sodium phosphate in an amount of 0.6 mg/g.

In certain embodiments, the reconstituted dosage unit includes a salt, such as a salt described in detail above. In certain instances, the reconstituted dosage unit includes a salt, such as sodium chloride. In some cases, the reconstituted dosage unit includes a salt (e.g., sodium chloride) in an amount ranging from 0.5 to 10 mg/g, such as 1 to 9 mg/g, or 1 to 8 mg/g, or 1 to 7 mg/g, or 1 to 6 mg/g, or 1 to 5 mg/g, or 2 to 5 mg/g, or 3 to 5 mg/g, or 4 to 5 mg/g, or 4 to 4.5 mg/g. For instance, the reconstituted dosage unit may include a salt (e.g., sodium chloride) in an amount ranging from 1 to 10 mg/g. In certain instances, the reconstituted dosage unit includes a salt (e.g., sodium chloride) in an amount ranging from 3 to 5 mg/g. In certain instances, the reconstituted dosage unit includes a salt (e.g., sodium chloride) in an amount ranging from 4 to 4.55 mg/g. For instance, the reconstituted dosage unit may include a salt (e.g., sodium chloride) in an amount of about 4 mg/g, such as 4.25 mg/g.

In certain embodiments, the reconstituted dosage unit includes a sugar, such as a sugar described in detail above. In certain instances, the reconstituted dosage unit includes a sugar, such as a disaccharide. In some cases, the reconstituted dosage unit includes a sugar, such as sucrose. In some cases, the reconstituted dosage unit includes an amount of sugar (e.g., sucrose) ranging from 1 to 250 mg/g, such as 5 to 200 mg/g, or 10 to 150 mg/g, or 10 to 100 mg/g, or 10 to 90 mg/g, or 10 to 80 mg/g, or 20 to 70 mg/g, or 20 to 60 mg/g, or 30 to 50 mg/g, or 40 to 50 mg/g. For instance, the reconstituted dosage unit may include a sugar (e.g., sucrose) in an amount ranging from 10 to 100 mg/g. In certain instances, the reconstituted dosage unit may include a sugar (e.g., sucrose) in an amount ranging from 30 to 50 mg/g. In certain instances, the reconstituted dosage unit may include a sugar (e.g., sucrose) in an amount ranging from 40 to 50 mg/g. For instance, the reconstituted dosage unit may include a sugar (e.g., sucrose) in an amount of 45 mg/g.

In certain embodiments, the dosage unit (e.g., liquid or reconstituted) has a pH compatible with physiological conditions. In some cases, the pH of the dosage unit ranges from 6 to 8. In some cases, the pH of the dosage unit ranges from 7 to 8. For example, the pH of the dosage unit may range from 7 to 7.5. In some cases, the pH of the dosage unit is 7.2. In some cases, the pH of the dosage unit is 7.3. In some cases, the pH of the dosage unit is 7.4. In certain embodiments, the method may include administering the dosage unit to the subject to deaminate asparagines in the subject. The route of administration may be selected according to a variety of factors including, but not limited to, the condition to be treated, the type of composition and/or device used, the patient to be treated, and the like. Routes of administration useful in the disclosed methods include, but are not limited to, oral and parenteral routes, such as intravenous (iv), intraperitoneal (ip), intramuscular (im), rectal, topical, ophthalmic, nasal, and transdermal. For example, compositions suitable for injection can be administered by an intravenous, intramuscular, intradermal, subcutaneous, sublingual, intraosseous, or other route of administration.

In some instances, administering the dosage unit to the subject includes intravenously administering the dosage unit to the subject. In some cases, administering the dosage unit to the subject includes intramuscularly administering the dosage unit to the subject.

In some instances, administering the reconstituted dosage unit to the subject includes intravenously administering the reconstituted dosage unit to the subject. In some cases, administering the reconstituted dosage unit to the subject includes intramuscularly administering the reconstituted dosage unit to the subject.

In certain embodiments, the method includes administering the dosage unit to the subject according to a treatment regimen. For example, in some cases, a subject to be treated may have been prescribed a treatment regimen from a health care provider. In some cases, a treatment regimen includes, but is not necessarily limited to, administration five times per day, four times per day, three times per day, twice per day, once per day, three times per week, twice per week, once per week, once every two weeks, once every three weeks, once per month, once every 5 weeks, once every 6 weeks, once every 7 weeks, once every other month, and any combination thereof.

In some embodiments, the treatment regimen includes administering one or more doses over an extended period of time. In certain cases, a single dose (e.g., a single dosage unit) is administered to the subject, and the initial dose may be followed by one or more doses administered to the subject at a subsequent time. In some instances, more than one dose (e.g., more than one dosage unit) is administered to the subject, and the initial doses may be followed by one or more doses administered to the subject at a subsequent time. For example, a single dose (e.g., a single dosage unit) may be administered to the subject, and the single dose may be followed by a single dose administered to the subject at a subsequent time. Additional single doses may be administered at subsequent points in time. In other cases, a single dose (e.g., a single dosage unit) may be administered to the subject, and the single dose may be followed by two doses administered to the subject at a subsequent time. Additional single or multiple doses may be administered at subsequent points in time.

In certain instances, the treatment regimen includes multiple phases. The treatment regimen may include multiple phases where the dosage schedule is different in each phase of the treatment regimen. In some cases, a subject is prescribed a treatment regimen with two phases; an induction phase and a consolidation phase. In certain instances, a subject is prescribed a treatment regimen with two phases where the dosage schedule of the first phase is different than the dosage schedule in the second phase. For example, a subject may be prescribed a treatment regimen with two phases including an induction phase and a consolidation phase, where the dosage schedule of the induction phase is different than the dosage schedule of the consolidation phase. In other embodiments, a subject may be prescribed a treatment regimen with three phases; an induction phase, a consolidation phase, and a maintenance phase. In some instances, a subject is prescribed a treatment regimen with three phases including an induction phase, a consolidation phase, and a maintenance phase, where the dosage schedule of each phase is different from the other phases. For instance, a subject may be prescribed a treatment regimen with three phases including an induction phase, a consolidation phase, and a maintenance phase, where the dosage schedules of the induction phase, the consolidation phase, and the maintenance phase are each different from each other.

In certain embodiments, the length of the treatment time during each phase of the treatment regimen is the same, or in other cases may be different. For example, the length of time during the induction phase may be 1 week or more, such as 2 weeks or more, or 3 weeks or more, or 4 weeks or more, or 5 weeks or more, or 6 weeks or more, or 7 weeks or more, or 8 weeks or more. In some cases, the length of time during the induction phase is 4 weeks. In some cases, the length of time during the induction phase is 5 weeks.

In certain embodiments, the length of time during the consolidation phase is 1 week or more, such as 2 weeks or more, or 3 weeks or more, or 4 weeks or more, or 5 weeks or more, or 6 weeks or more, or 7 weeks or more, or 8 weeks or more, or 9 weeks or more, or 10 weeks or more, or 11 weeks or more, or 12 weeks or more, or 13 weeks or more, or 14 weeks or more, or 15 weeks or more, or 16 weeks or more, or 17 weeks or more, or 18 weeks or more, or 19 weeks or more, or 20 weeks or more, or 21 weeks or more, or 22 weeks or more, or 23 weeks or more, or 24 weeks or more, or 25 weeks or more, or 26 weeks or more, or 27 weeks or more, or 28 weeks or more, or 29 weeks or more, or 30 weeks or more, or 31 weeks or more, or 32 weeks or more. In some cases, the length of time during the consolidation phase is 8 weeks. In some cases, the length of time during the consolidation phase is 27 weeks. In some cases, the length of time during the consolidation phase is 30 weeks.

In certain embodiments, the length of time during the maintenance phase is 1 week or more, such as 2 weeks or more, or 3 weeks or more, or 4 weeks or more, or 5 weeks or more, or 6 weeks or more, or 7 weeks or more, or 8 weeks or more, or 9 weeks or more, or 10 weeks or more, or 12 weeks or more, or 16 weeks or more, or 20 weeks or more, or 24 weeks or more, or 28 weeks or more, or 32 weeks or more, or 36 weeks or more, or 40 weeks or more, or 44 weeks or more, or 48 weeks or more, or 52 weeks or more, or 56 weeks or more, or 60 weeks or more, or 64 weeks or more, or 68 weeks or more, or 72 weeks or more, or 76 weeks or more, or 80 weeks or more, or 84 weeks or more, or 88 weeks or more, or 92 weeks or more, or 96 weeks or more, or 100 weeks or more, or 104 weeks or more, or 108 weeks or more, or 112 weeks or more, or 116 weeks or more, or 120 weeks or more, or 124 weeks or more, or 128 weeks or more, or 132 weeks or more, or 136 weeks or more, or 140 weeks or more, or 144 weeks or more, or 148 weeks or more, or 152 weeks or more, or 156 weeks or more, or 160 weeks or more, or 164 weeks or more, or 168 weeks or more, or 172 weeks or more, or 176 weeks or more, or 180 weeks or more. In some cases, the length of time during the maintenance phase is 8 weeks. In some cases, the length of time during the maintenance phase is 88 weeks. In some cases, the length of time during the maintenance phase is 104 weeks. In some cases, the length of time during the consolidation phase is 140 weeks. In some cases, the length of time during the maintenance phase is 156 weeks. In some cases, the length of time during the maintenance phase ranges from 88 to 104 weeks. In some cases, the length of time during the maintenance phase ranges from 88 to 140 weeks. In some cases, the length of time during the maintenance phase ranges from 88 to 156 weeks.

Examples of the treatment regimens that may be administered to a subject include, but are not limited to, those described here. In certain embodiments, the treatment regimen includes administering a single dosage unit to a subject in an induction phase and multiple dosage units during a maintenance phase. In certain embodiments, the treatment regimen includes administering a single dosage unit to a subject in an induction phase and multiple dosage units during a consolidation phase. For example, the multiple dosage units may be administered to the subject by administering a dosage unit to the subject every 3 weeks (e.g., during the consolidation phase). In some cases, a single dosage unit is administered to the subject once every 3 weeks. As described above, the consolidation phase may be 30 weeks, and thus a total of 10 dosage units may be administered to the subject (e.g., a single dosage unit may be administered to the subject once every 3 weeks for 30 weeks). Additional (or fewer) dosage units may be administered to the subject in between the induction phase and the consolidation phase, or after the consolidation phase, as desired or prescribed by a health care provider.

In other examples, the treatment regimen may include administering a single dosage unit to a subject in an induction phase and multiple dosage units during a consolidation phase, where the multiple dosage units may be administered to the subject by administering a dosage unit to the subject every 2 weeks. In some cases, a single dosage unit is administered to the subject once every 2 weeks. As described above, the consolidation phase may be 30 weeks, and thus a total of 15 dosage units may be administered to the subject (e.g., a single dosage unit may be administered to the subject once every 2 weeks for 30 weeks). Additional (or fewer) dosage units may be administered to the subject in between the induction phase and the consolidation phase, or after the consolidation phase, as desired or prescribed by a health care provider.

In other embodiments, the treatment regimen includes administering a single dosage unit to a subject in an induction phase, multiple dosage units during a consolidation phase, and multiple dosage units during a maintenance phase. For example, the multiple dosage units during the consolidation phase may be administered to the subject on certain days following initiation of the consolidation phase. In some instances, the multiple dosage units during the consolidation phase may be administered to the subject by administering more than one dosage unit to the subject at the same time. For example, the multiple dosage units during the consolidation phase may be administered to the subject by administering more than one dosage unit to the subject on a particular day following initiation of the consolidation phase and more than one dosage unit to the subject on a subsequent day during the consolidation phase. An example of this type of treatment regimen may include administering 2 dosage units to the subject on day 15 following initiation of the consolidation phase and 2 dosage units on day 43 following initiation of the consolidation phase. Additional (or fewer) dosage units may be administered to the subject in between the induction phase and the consolidation phase, or after the consolidation phase but before the maintenance phase, as desired or prescribed by a health care provider.

In certain embodiments, the multiple dosage units during the maintenance phase may be administered to the subject on certain days following initiation of the maintenance phase. In some instances, the multiple dosage units during the maintenance phase may be administered to the subject by administering more than one dosage unit to the subject at the same time. For example, the multiple units during the maintenance phase may be administered to the subject by administering more than one dosage unit to the subject on a particular day following initiation of the maintenance phase and more than one dosage unit to the subject on a subsequent day during the maintenance phase. An example of this type of treatment regimen may include administering 2 dosage units to the subject on day 2 following initiation of the maintenance phase and 2 dosage units on day 22 following initiation of the maintenance phase. Another example of a treatment regimen during the maintenance phase may include administering 2 dosage units to the subject on day 4 following initiation of the maintenance phase and 2 dosage units on day 43 following initiation of the maintenance phase. In some cases, a treatment regimen may include multiple maintenance phases. In certain instances, the dosage schedule during each maintenance phase may be the same, or in other instances the dosage schedule during each maintenance phase may be different. Additional (or fewer) dosage units may be administered to the subject in between the consolidation phase and the maintenance phase, or after the maintenance phase, or in between different maintenance phases, as desired or prescribed by a health care provider.

In certain embodiments, dosage units of the present disclosure can be administered prior to, concurrent with, or subsequent to other active agents for treating related or unrelated conditions, e.g., in combination therapy. Examples of such additional therapies include radiation therapies, surgical therapies and chemotherapeutic therapies. If provided at the same time as other active agents, dosage units of the present disclosure can be provided in the same or in a different formulation. For example, concurrent therapy may be achieved by administering a dosage unit and a pharmaceutical composition having at least one other active agent, such as a chemotherapeutic agent, which in combination provide a therapeutically effective dose, according to a particular treatment regimen. Administration of separate pharmaceutical compositions can be performed simultaneously or at different times (e.g., sequentially, in either order, on the same day, or on different days), as long as a therapeutically effective effect of the combination of these substances is caused in the subject undergoing therapy.

Accordingly, aspects of the present disclosure further include combination therapies. In certain embodiments, the subject method includes administering a therapeutically effective amount of one or more additional active agents. By combination therapy is meant that a polyalkylene oxide asparaginase (e.g., as described herein) can be used in a combination with another therapeutic agent to treat a single disease or condition. In certain embodiments, a compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or subsequent to administration of another therapeutic agent.

The subject compounds can be used jointly with any agent useful in the treatment of a neoplastic condition, such as anti-cancer agents and anti-tumor agents. One class of anti-cancer agents of interest includes chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation. Agents of interest which can be used in jointly with the subject compounds include, but are not limited to, Cancer chemotherapeutic agents, Agents that act to reduce cellular proliferation, Antimetabolite agents, Microtubule affecting agents, Hormone modulators and steroids, natural products and Biological response modifiers, e.g., as described in greater detail below.

Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indoledliones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine. Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17a-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*). Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfonamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Subjects that may be treated using the methods and compositions of the present disclosure include subjects of any age. In some cases, the subject may be an adult. For example a human adult subject may be 18 years or older. Subjects that may be treated using the methods and compositions of the present disclosure also include juvenile subjects. For example a human juvenile subject may be less than 18 years old. In some instances, the subjects range in agent from 1 month to 18 years, such as 1 year to 18 years, including 2 years to 18 years, e.g., 5 years to 16 years.

In some instances, the methods include diagnosing a subject as having AML. A subject may be diagnosed as having AML using any convenient protocol. In some instances, the French, American, and British (FAB) classification system is employed to diagnose and classify acute myeloid leukemia. The diagnosis of acute myeloid leukemia requires that myeloblasts constitute 30% (or 20% based on a recent World Health Organization (WHO) classification system) or more of bone marrow cells or circulating white blood cells. The hematologic properties of the disease, defines the various subtypes described below. The FAB nomenclature (M1 through M7) classifies the subtypes of acute myeloid leukemia according to the normal marrow elements that the blasts most closely resemble. In some instances, the methods include determining suitability of a subject diagnosed as having AML for treatment using a polyalkylene oxide apsaraginase composition, e.g., as described herein. In some instances, the methods include monitoring the effectiveness of treatment. Effectiveness of treatment may be monitored using any convenient protocol.

Methods of Making

Aspects of the present disclosure include methods of making the polyalkylene oxide-asparaginase compositions described herein. In certain cases, the method is a method of making a liquid polyalkylene oxide-asparaginase composition as described herein. The method may include producing an aqueous composition that includes a polyalkylene oxide-asparaginase having a polyalkylene oxide group covalently linked by a linker to an asparaginase, a buffer, and a salt.

Embodiments of the methods of making the polyalkylene oxide-asparaginase composition may include producing an aqueous concentrate composition. For example, the method for producing the aqueous concentrate composition may include one or more of the steps of: preparing a solution of asparaginase (e.g., L-asparaginase); attaching a polyalkylene oxide (e.g., polyethylene glycol) to the asparaginase; clarifying the polyalkylene oxide-asparaginase; filtering and concentrating the solution of the polyalkylene oxide-asparaginase; diluting the solution of the polyalkylene oxide-asparaginase; filtering the solution of the polyalkylene oxide-asparaginase and filling the solution of the polyalkylene oxide-asparaginase into a sterile container; and storing the solution of the polyalkylene oxide-asparaginase.

In the method for producing the aqueous concentrate composition, a solution of asparaginase (e.g., L-asparaginase) may be prepared. The asparaginase may be mixed with a solution, such as an aqueous solution (e.g., a buffered aqueous solution). Examples of suitable buffers include, but are not limited to, a phosphate buffer, phosphate buffered saline (PBS), Dulbecco's phosphate buffered saline (DPBS), Hank's balanced salt solution (HBSS), Earle's balanced salt solution (EBSS), Tris buffer, Ringer's lactate buffer, borate buffer, and the like, and combinations thereof. In some cases, the asparaginase is mixed with a phosphate buffer.

The phosphate buffer can include dibasic sodium phosphate and monobasic sodium phosphate. In some cases, the amount of dibasic sodium phosphate in the aqueous concentrate composition ranges from 0.05 to 5 wt. %, such as 0.1 to 4.5 wt. %, or 0.1 to 4 wt. %, or 0.1 to 3.5 wt. %, or 0.1 to 3 wt. %, or 0.1 to 2.5 wt. %, or 0.1 to 2 wt. %, or 0.1 to 1 wt. %, or 0.1 to 0.9 wt. %, or 0.1 to 0.8 wt. %, or 0.1 to 0.7 wt. %, or 0.1 to 0.6 wt. %, or 0.2 to 0.6 wt. %, or 0.3 to 0.6 wt. %, or 0.4 to 0.6 wt. %, or 0.5 to 0.6 wt. %. For instance, the dibasic sodium phosphate may be present in the aqueous concentrate composition in an amount ranging from 0.1 to 1 wt. %. In certain instances, the dibasic sodium phosphate may be present in the composition in an amount ranging from 0.2 to 0.8 wt. %. In certain instances, the dibasic sodium phosphate may be present in the composition in an amount ranging from 0.3 to 0.6 wt. %. In certain instances, the dibasic sodium phosphate may be present in the composition in an amount ranging from 0.5 to 0.6 wt. %. For instance, the dibasic sodium phosphate may be present in the composition in an amount of about 0.6 wt. %, such as 0.56 wt. % (or 0.558 wt. %). In certain embodiments, the amount of monobasic sodium phosphate in the aqueous concentrate composition ranges 0.005 to 2 wt. %, such as 0.01 to 1.8 wt. %, or 0.01 to 1.6 wt. %, or 0.01 to 1.4 wt. %, or 0.01 to 1.2 wt. %, or 0.01 to 1.0 wt. %, or 0.01 to 0.8 wt. %, or 0.01 to 0.6 wt. %, or 0.01 to 0.4 wt. %, or 0.01 to 0.2 wt. %, or 0.02 to 0.18 wt. %, or 0.03 to 0.16 wt. %, or 0.04 to 0.16 wt. %, or 0.045 to 0.15 wt. %, or 0.04 to 0.14 wt. %, or 0.05 to 0.14 wt. %, or 0.1 to 0.2 wt. %, or 0.1 to 0.15 wt. %. For instance, the monobasic sodium phosphate may be present in the aqueous concentrate composition in an amount ranging from 0.05 to 0.2 wt. In certain instances, the monobasic sodium phosphate may be present in the composition in an amount ranging from 0.01 to 0.2 wt. %. In certain instances, the monobasic sodium phosphate may be present in the composition in an amount ranging from 0.09 to 0.15 wt. %. In certain instances, the monobasic sodium phosphate may be present in the composition in an amount ranging from 0.1 to 0.2 wt. %. In certain instances, the monobasic sodium phosphate may be present in the composition in an amount ranging from 0.1 to 0.15 wt. %. For instance, the monobasic sodium phosphate may be present in the composition in an amount of 0.12 wt. % (or 0.129 wt. %).

Additional components that may be included in the aqueous concentrate composition include a salt. Examples of suitable salts include, but are not limited to, sodium chloride, potassium chloride, calcium chloride, magnesium chloride, and the like, and combinations thereof. In certain instances, the salt is sodium chloride.

In some cases, the amount of salt (e.g., sodium chloride) in the aqueous concentrate composition ranges from 0.05 to 5 wt. %, such as 0.05 to 4 wt. %, or 0.05 to 3 wt. %, or 0.05 to 2 wt. %, or 0.1 to 5 wt. %, or 0.1 to 4 wt. %, or 0.1 to 3 wt. %, or 0.1 to 2 wt. %, or 0.1 to 1.5 wt. %, or 0.1 to 1 wt. %, or 0.2 to 1 wt. %, or 0.3 to 1 wt. %, or 0.4 to 1 wt. %, or 0.5 to 1 wt. %, or 0.6 to 1 wt. %, or 0.7 to 1 wt. %, or 0.8 to 1 wt. %, or 0.8 to 0.9 wt. %. For instance, the salt (e.g., sodium chloride) may be present in the composition in an amount ranging from 0.5 to 1 wt. %. For instance, the salt (e.g., sodium chloride) may be present in the composition in an amount ranging from 0.2 to 2 wt. %. In certain instances, the salt (e.g., sodium chloride) may be present in the composition in an amount ranging from 0.7 to 1 wt. %. In certain instances, the salt (e.g., sodium chloride) may be present in the composition in an amount ranging from 0.8 to 0.9 wt. %. For instance, the salt (e.g., sodium chloride) may be present in the composition in an amount of 0.85 wt. %.

Other aspects of the present disclosure include methods of making the lyophilized storage stable compositions described herein. In certain cases, the method is a method of making a lyophilized polyalkylene oxide-asparaginase composition as described herein. The method may include lyophilizing an aqueous composition that includes a polyalkylene oxide-asparaginase having a polyalkylene oxide group covalently linked by a linker to an asparaginase, a buffer, a salt, and a sugar in a manner sufficient to produce a lyophilized storage stable polyalkylene oxide-asparaginase composition.

In certain embodiments, lyophilizing is used to dehydrate the aqueous concentrate composition. In some instances, lyophilizing includes removing water from the aqueous concentrate composition. The water may be removed by sublimating the water in the composition. For instance, the water in the composition may undergo a phase transition from a solid to a gas. In certain cases, lyophilizing includes freezing the composition (e.g., freezing the water in the composition) and then reducing the pressure surrounding the composition such that the water in the composition undergoes sublimation. During lyophilization, the temperature of the composition may be reduced, for example to a temperature below the freezing point of water in the composition. For example, the temperature of the composition may be reduced to 0° C. or less, or –5° C. or less, or –10° C. or less, or –15° C. or less, or –20° C. or less, or –25° C. or less, or –30° C. or less, or –35° C. or less, or –40° C. or less, or –45° C. or less, or –50° C. or less, or –55° C. or less, or –60° C. or less, or –65° C. or less, or –75° C. or less. In some cases, the temperature of the composition is reduced to –45° C. In some cases, the temperature of the composition is reduced to –30° c.

In certain embodiments, the pressure surrounding the composition is reduced below standard atmospheric pressure. For example, the pressure surrounding the composition may be reduced to 500 T or less, such as 250 T or less, or 100 T or less, or 50 T or less, or 10 T or less, or 1 T or less, or 500 mT or less, or 400 mT or less, or 300 mT or less, or 200 mT or less, or 100 mT or less, or 90 mT or less, or 80 mT or less, or 70 mT or less, or 60 mT or less, or 50 mT or less, or 40 mT or less, or 30 mT or less, or 20 mT or less, or 10 mT or less. In some cases, the pressure surrounding the composition is reduced to 60 mT or less, such as 50 mT.

In some embodiments, lyophilizing may also include increasing the temperature of the composition while the pressure surrounding the composition is reduced. For example, the temperature of the composition may be increased from a minimum temperature as described above to a temperature greater than the minimum temperature. In some cases, the temperature is increased to facilitate sublimation of the water in the composition at the reduced surrounding pressure.

Embodiments of the method of making the lyophilized polyalkylene oxide-asparaginase composition may also include producing the aqueous concentrate composition, which is subsequently lyophilized. A process flow diagram of a method for producing the aqueous concentrate composition is shown in FIG. 1. As shown in FIG. 1, the method for producing the aqueous concentrate composition may include one or more of the steps of: preparing a solution of asparaginase (e.g., L-asparaginase) (10); attaching a polyalkylene oxide (e.g., polyethylene glycol) to the asparaginase (20); clarifying the polyalkylene oxide-asparaginase (30); filtering and concentrating the solution of the polyalkylene oxide-asparaginase (40); diluting the solution of the polyalkylene oxide-asparaginase (50); filtering the solution of the polyalkylene oxide-asparaginase and filling the solution of the polyalkylene oxide-asparaginase into a sterile container (60); and storing the solution of the polyalkylene oxide-asparaginase (70).

In the method for producing the aqueous concentrate composition, a solution of asparaginase (e.g., L-asparaginase) may be prepared. The asparaginase may be mixed with a solution, such as an aqueous solution (e.g., a buffered aqueous solution). Examples of suitable buffers include, but are not limited to, a phosphate buffer, phosphate buffered saline (PBS), Dulbecco's phosphate buffered saline (DPBS), Hank's balanced salt solution (HBSS), Earle's balanced salt solution (EBSS), Tris buffer, Ringer's lactate buffer, borate buffer, and the like, and combinations thereof. In some cases, the asparaginase is mixed with a phosphate buffer.

In some embodiments, the phosphate buffer can include dibasic sodium phosphate and monobasic sodium phosphate. In some cases, the amount of dibasic sodium phosphate in the aqueous concentrate composition ranges from 0.05 to 1 wt. %, such as 0.1 to 0.9 wt. %, or 0.1 to 0.8 wt. %, or 0.1 to 0.7 wt. %, or 0.1 to 0.6 wt. %, or 0.1 to 0.5 wt. %, or 0.1 to 0.4 wt. %, or 0.2 to 0.4 wt. %, or 0.2 to 0.3 wt. %, or 0.25 to 0.3 wt. %. For instance, the dibasic sodium phosphate may be present in the aqueous concentrate composition in an amount ranging from 0.1 to 0.5 wt. %. In certain embodiments, the amount of monobasic sodium phosphate in the aqueous concentrate composition ranges from 0.005 to 1 wt. %, such as 0.01 to 0.9 wt. %, or 0.01 to 0.8 wt. %, or 0.01 to 0.7 wt. %, or 0.01 to 0.6 wt. %, or 0.01 to 0.5 wt. %, or 0.01 to 0.4 wt. %, or 0.01 to 0.3 wt. %, or 0.01 to 0.2 wt. %, or 0.01 to 0.1 wt. %, or 0.02 to 0.09 wt. %, or 0.03 to 0.08 wt. %, or 0.04 to 0.08 wt. %, or 0.045 to 0.075 wt. %, or 0.04 to 0.07 wt. %, or 0.05 to 0.07 wt. %. For instance, the monobasic sodium phosphate may be present in the aqueous concentrate composition in an amount ranging from 0.01 to 0.1 wt.

Additional components that may be included in the aqueous concentrate composition include a salt. Examples of suitable salts include, but are not limited to, sodium chloride, potassium chloride, calcium chloride, magnesium chloride, and the like, and combinations thereof. In certain instances, the salt is sodium chloride.

In some cases, the amount of salt (e.g., sodium chloride) in the aqueous concentrate composition ranges from 0.05 to 1 wt. %, such as 0.1 to 0.9 wt. %, or 0.1 to 0.8 wt. %, or 0.1 to 0.7 wt. %, or 0.1 to 0.6 wt. %, or 0.1 to 0.5 wt. %, or 0.2 to 0.5 wt. %, or 0.3 to 0.5 wt. %, or 0.4 to 0.5 wt. %, or 0.4 to 0.45 wt. %. For instance, the salt (e.g., sodium chloride) may be present in the aqueous concentrate composition in an amount ranging from 0.1 to 1 wt. %.

Another component that may be included in the aqueous concentrate composition is a sugar. Examples of suitable sugars include, but are not limited to, sucrose, mannitol, maltose, trehalose, 2-hydroxypropyl-beta-cyclodextrin (-HPCD), lactose, glucose, fructose, galactose, glucosamine, and the like, and combinations thereof. In certain instances, the sugar is a disaccharide. For example, the disaccharide may be sucrose.

In some cases, the amount of sugar (e.g., sucrose) in the aqueous concentrate composition ranges from 0.1 to 25 wt. %, such as 0.5 to 20 wt. %, or 1 to 15 wt. %, or 1 to 10 wt. %, or 1 to 9 wt. %, or 1 to 8 wt. %, or 2 to 7 wt. %, or 2 to 6 wt. %, or 3 to 5 wt. %, or 4 to 5 wt. %. For instance, the sugar (e.g., sucrose) may be present in the aqueous concentrate composition in an amount ranging from 1 to 10 wt. %.

After preparation of the asparaginase solution, the asparaginase may be attached to a polyalkylene oxide (e.g., polyethylene glycol), such that the polyalkylene oxide is covalently bonded to the asparaginase to produce a polyalkylene oxide-asparaginase conjugate. After preparation of the polyalkylene oxide-asparaginase, the solution may undergo clarification. In some cases, clarification includes filtering the solution through a filter to remove particulate matter from the solution. The filtering step may produce a substantially purified polyalkylene oxide-asparaginase.

In some instances, the filtered polyalkylene oxide-asparaginase solution is then subjected to a diafiltration and concentration step. The polyalkylene oxide-asparaginase solution may be diafiltered using an ultrafiltration membrane and a resulting concentrate of the polyalkylene oxide-asparaginase may be obtained. The concentrate from the diafiltration step may then be diluted such that the solution contains a desired concentration of the polyalkylene oxide-asparaginase. Suitable buffers useful for the dilution step include those described above. In some cases, a phosphate buffer is used to dilute the polyalkylene oxide-asparaginase solution, thus producing the desired aqueous concentrate composition. For example, the concentrate from the diafiltration step may be diluted such that the resulting aqueous concentrate composition includes an amount of polyalkylene oxide-asparaginase having a potency (activity)) ranging from 100 to 5,000 IU/mL, such as 500 to 4,500 IU/mL, or 500 to 4,000 IU/mL, or 500 to 3,500 IU/mL, or 500 to 3,000 IU/mL, or 1,000 to 3,000 IU/mL, or 1,500 to 3,000 IU/mL. In certain instances, the aqueous concentrate composition includes the polyalkylene oxide-asparaginase in an amount ranging from 1,500 to 3,000 IU/mL. In some cases, the amount of polyalkylene oxide-asparaginase in the aqueous concentrate composition is greater than the amount of polyalkylene oxide-asparaginase in the reconstituted lyophilized composition described herein. In some cases, the diafiltration produces a substantially purified polyalkylene oxide-asparagmase.

The aqueous concentrate composition may then be filtered and filled into a sterile container. Examples of suitable container materials for the container include polymers, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), polystyrene, and the like. For example, the container may be a sterile polymer bag. The aqueous concentrate composition may be stored in the container for a period of time, and may be processed into the lyophilized storage stable composition of the present disclosure.

Embodiments of the method may further include shipping the aqueous concentrate composition to a remote location. A "remote location," is a location other than the location at which the aqueous concentrate composition is produced. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or one hundred miles or more apart.

In certain embodiments, as described above, the method includes lyophilizing the aqueous concentrate composition in a manner sufficient to produce a lyophilized storage stable polyalkylene oxide-asparaginase composition. In some instances, the lyophilization may be performed in a unit dosage container. Lyophilizing the aqueous concentrate composition to produce the lyophilized storage stable polyalkylene oxide-asparaginase composition in the unit dosage container may facilitate production of the lyophilized composition in the unit dosage container, for example, by eliminating the need to lyophilize the aqueous concentrate composition in a separate container and then transfer the lyophilized composition from the separate container to the unit dosage container. As such, in some embodiments, the method includes introducing the aqueous concentrate composition into a unit dosage container and lyophilizing the aqueous concentrate composition in the unit dosage container. As described above, the unit dosage container may be a vial, such as a glass vial.

After lyophilization, the method may further include sealing the lyophilized composition in the unit dosage container. For example, a seal or cap may be applied to the opening of the unit dosage container, thus sealing the unit dosage container. The sealed containers may be stored for an extended period of time, such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. For instance, an extended period of time may be 6 months or more. In some cases, the sealed containers may be stored for 9 months or more. In some cases, the sealed containers may be stored for 1 year (e.g., 12 months) or more. In some cases, the sealed containers may be stored for 1.5 years (e.g., 18 months) or more. In some cases, the sealed containers may be stored for 2 years (e.g., 24 months) or more.

Kits

Also provided are kits for use in practicing the subject methods, where the kits may include one or more of the above liquid and/or lyophilized compositions. For example, the kit may include a unit dosage container that contains a liquid composition as described herein. Or, for example, the kit may include a unit dosage container that contains a lyophilized composition as described herein. In some instances, the kit includes two or more unit dosage containers each containing a liquid composition as described herein. In some instances, the kit includes two or more unit dosage containers each containing a lyophilized composition as described herein. In some instances, the kit includes two or more unit dosage containers, where one or more of the unit dosage containers contains a liquid composition as described herein and one or more of the unit dosage containers contains a lyophilized composition as described herein. In certain embodiments, the kit includes a packaging configured to contain the unit dosage container(s). The packaging may be a sealed packaging, such as a sterile sealed packaging. A sterile packaging may be configured to be sealed from the outside environment, such that there are substantially no microbes (such as fungi, bacteria, viruses, spore forms, etc.) inside the packaging. In some instances, the packaging is sealed, such as a water vapor-resistant packaging, optionally under an air-tight and/or vacuum seal.

In certain embodiments, the kit includes a buffer. For instance, the kit may include a dilution liquid, e.g., a dilution buffer, which may be suitable for administration to a subject, and the like. The kit may further include other components, e.g., administration devices, liquid sources, etc., which may find use in practicing the subject methods. The various components in the kits may be packaged as desired, e.g., together or separately. Components of the subject kits may be present in separate containers, or multiple components may be present in a single container, where the containers and/or packaging (or a portion thereof) of the kit may be sterile, as desired.

In addition to above mentioned components, the subject kits may further include instructions for using the components of the kit to practice the subject methods. The instructions for practicing the subject methods are generally recorded on a suitable recording medium. For example, the instructions may be printed, such as on paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. portable flash drive, CD-ROM, DVD-ROM, Blu-ray, etc. In yet other embodiments, the actual instructions are not present in the kit, but directions for obtaining the instructions from a remote source, e.g. via the Internet, are provided. An example of this embodiment is a kit that includes a web address where the instructions can be viewed and/or from which the instructions can be downloaded. As with the instructions, this embodiment for obtaining the instructions is recorded on a suitable substrate.

Utility

The subject compositions (e.g., liquid or lyophilized storage stable compositions) and methods find use in applications where there is a desire to treat a subject for a disease or condition amenable to treatment by administration of a polyalkylene oxide-asparaginase. For example, the subject compositions (e.g., liquid or lyophilized storage stable compositions) and methods find use in the treatment of a neoplastic condition in a subject. In some cases, the subject compositions (e.g., liquid or lyophilized storage stable compositions) and methods find use in the treatment of a cancer in the subject. Examples of types of cancers amenable to treatment using the subject compositions (e.g., liquid or lyophilized storage stable compositions) and methods include, but are not limited to, leukemia, such as acute lymphoblastic leukemia (ALL), acute myeloid leukemia (AML), and the like. Accordingly, the subject lyophilized storage stable compositions and methods find use in providing a therapeutically effective treatment for neoplastic conditions, such as a cancer, including, but not limited to, leukemia, such as acute lymphoblastic leukemia (ALL), acute myeloid leukemia (AML), and the like.

The lyophilized storage stable compositions and methods of the present disclosure find use in treating subjects of any age. In some cases, the subject compositions (e.g., liquid or lyophilized storage stable compositions) and methods find use in treating an adult. For example a human adult subject may be 18 years or older. In other cases, the compositions (e.g., liquid or lyophilized storage stable compositions) and methods find use in treating a juvenile. For example a human juvenile subject may be less than 18 years old.

The compositions and methods of the present disclosure find use in applications where a storage stable composition is desired. For example, the compositions and methods of the present disclosure find use in providing a storage stable composition that is stable (e.g., does not significantly degrade and/or retains substantially all its activity) aver an extended period of time. For instance, the compositions and methods of the present disclosure find use in providing a storage stable composition that is stable for an extended period of time, such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. In some cases, the compositions and methods of the present disclosure find use in providing a storage stable composition that is stable for 9 months or more. In some cases, the compositions and methods of the present disclosure find use in providing a storage stable composition that is stable for 1 year (e.g., 12 months) or more. In some cases, the compositions and methods of the present disclosure find use in providing a storage stable composition that is stable for 1.5 years (e.g., 18 months) or more. In some cases, the compositions and methods of the present disclosure find use in providing a storage stable composition that is stable for 2 years (e.g., 24 months) or more. In certain embodiments, the compositions and methods of the present disclosure find use in providing a storage stable composition that increases the shelf life of the composition by up to 1 week, or 2 weeks, or 3 weeks, or 1 month, or 2 months, or 3 months, or 4 months, or 6 months, or 9 months, or 1 year, or 1.5 years (e.g., 18 months), or 2 years, or 2.5 years (e.g., 30 months), or 3 years, or 3.5 years (e.g., 42 months), or 4 years or more, or 4.5 years (e.g., 54 months), or 5 years. In certain embodiments, the compositions and methods of the present disclosure find use in providing a storage stable composition that increases the shelf life of the composition by 1 month to 5 years, or 6 months to 4 years, or 9 months to 3 years, or 1 year to 2 years.

In certain embodiments, dosages of the present disclosure can be administered prior to, concurrent with, or subsequent to other one or more other neoplastic condition therapies for treating related or unrelated conditions. If provided at the same time as other neoplastic condition therapies, dosages of the present disclosure can be provided in the same or in a different formulation. For example, concurrent therapy may be achieved by administering a dosage and a pharmaceutical composition having at least one other active agent, such as a chemotherapeutic agent, which in combination provide a therapeutically effective dose, according to a particular treatment regimen. Administration of separate pharmaceutical compositions or treatments can be performed simultaneously or at different times (e.g., sequentially, in either order, on the same day, or on different days), as long as a therapeutically effective effect of the combination of these substances is caused in the subject undergoing therapy. Accordingly, methods and compositions of the present disclosure find use in treating a subject using a combination therapy that includes administering a polyalkylene oxide-asparaginase of the present disclosure in combination with one or more additional active agent(s) and/or therapies (e.g., radiation, chemotherapy, immunotherapy, etc.).

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

The following examples are offered for illustrative purposes only, and are not intended to limit the scope of the embodiments of the present disclosure in any way. Efforts have been made to ensure accuracy with respect to numbers used (e.g., amounts, temperatures, etc.), but some experimental error and deviation should, of course, be allowed for.

EXAMPLES

Example 1

A concentrated bulk composition that included a polyethylene glycol-asparaginase having an SS-PEG linker was produced according to the following protocol. Following production of the concentrated bulk composition, a lyophilized composition was produced from the concentrated bulk composition according to the protocol described below. FIG. 1 shows a process flow diagram for a method of making a lyophilized storage stable composition according to embodiments of the present disclosure.

L-Asparaginase Solution Preparation

The amount of L-asparaginase required for processing was calculated, weighed into a 6 L stainless steel beaker, and mixed for 5 to 10 minutes. The amount of phosphate buffer needed to dilute the L-asparaginase to a target concentration of 5 mg/mL was calculated and weighed. The L-asparaginase was then added to the phosphate buffer and mixed in a 7 gallon stainless steel pressure vessel for 10 to 15 minutes. Samples were taken and submitted for protein and specific activity testing.

PEGylation

The amount of SS-PEG required for this step was calculated and weighed. The 7 gallon stainless steel pressure vessel containing the diluted L-asparaginase solution was heated to 29 to 31° C. under gentle agitation. Once the L-asparaginase solution reached the appropriate temperature range, the mixer speed was increased, and the titration pump was started. Once the pH was adjusted to 7.7-7.9 with 0.5 N NaOH, the SS-PEG was added to the 7 gallon stainless steel pressure vessel. After 30 minutes, the titration pump was stopped and the temperature jacket was disconnected.

Clarification

The process material was then filtered through a 0.45 µm filter (Millipore, Billerica, Massachusetts) into another 7 gallon stainless steel pressure vessel using a diafiltration peristaltic pump. After clarification, phosphate buffer was added to the original 7 gallon stainless steel pressure vessel and pumped through the 0.45 µm filter into the 7 gallon stainless steel pressure vessel as a rinse.

Diafiltration/Concentration

The amount of PBS required for 15× diafiltration was calculated and the diafiltration system was prepared. The 7 gallon stainless steel pressure vessel was placed on a scale. A Millipore Pellicon®-2 diafiltration system was set up with membranes of 100,000 Da nominal molecular weight limits, which were pre-conditioned using a diafiltration peristaltic pump and 5 L of PBS. The level control system, including a buffer peristaltic pump, was then set up and the 7-gallon stainless steel pressure vessel placed on top of a scale. The Pellicon®-2 system was filled with polyethylene glycol-asparaginase for conditioning and recirculated for 5 minutes. Following conditioning, the permeate waste line was opened and diafiltration was started. After 15 and 30 minutes, a sample was obtained from the permeate waste line into a vial and submitted for activity and protein testing. Material intended for lyophilization was diafiltered then concentrated to 18.0 mg/mL or more and a potency of 1,850 IU/mL or more. When diafiltration was complete, the volume of in-process material in the 7 gallon stainless steel pressure vessel was adjusted to reach the target concentration (18.0 mg/mL or more for the process for lyophilized formulation) by removing the appropriate amount of permeate. PBS was then pumped through the system into the 7 gallon stainless steel pressure vessel as a rinse.

Quality control assays of the product after diafiltration were performed, including a determination of the impurity profile of the product. Permeate Enzyme Enzymatic Activity (EEA) was measured after 15 minutes and 30 minutes to ensure that product was retained by the diafiltration membrane. Free PEG and N-Hydroxysuccinimide (NHS) were components of the process related impurity profile measured in the final product. Formal in-process controls for the diafiltration unit operation are presented in Table 1 below.

The NHS and Free-PEG data generated from three drug substance compositions (e.g., concentrated bulk drug substance compositions) intended for lyophilization are shown in Table 2 below. Data generated demonstrated that small changes to diafiltration/concentration process did not affect the quality of the product.

TABLE 1

Specifications for Bulk Drug Substance Compositions Intended for Lyophilization

| Test | Acceptance Criteria for Drug Substance Compositions for Lyophilization |
|---|---|
| N-Hydroxysuccinimide (NHS) | ≤ 6.0 ppm |
| Modification by 2,4,6-Trinitrobenzenesulfonic acid (TNBS) | 69-82 moles PEG/mole protein |

TABLE 1-continued

Specifications for Bulk Drug Substance Compositions Intended for Lyophilization

| Test | Acceptance Criteria for Drug Substance Compositions for Lyophilization |
|---|---|
| Endotoxin | ≤ 35 EU/mL |
| Bioburden | ≤ 2 CFU/20 mL |
| Sterility (performed after sterile filtration) | Complies |

TABLE 2

Concentrated Bulk Drug Substance Composition Batch Analysis

| Test | Acceptance Criteria | Lot 1 | Lot 2 | Lot 3 |
|---|---|---|---|---|
| Protein concentration | 19.0 to 21.0 mg/mL | 20.94 | 19.65* | 18.37 |
| Potency (activity) | ≥ 1850 IU/mL | 2305 | 2360* | 2091 |
| Appearance | Colorless solution | Complies | Complies | Complies |
| Clarity | Clear, no visible particles | Complies | Complies | Complies |
| pH | 7.2 to 7.4 | 7.2 | 7.2 | 7.2 |
| Specific activity | ≥ 85 IU/mg of protein | 110 | 116 | 114 |
| Purity by GF-HPLC | ≥ 95% Active components; ≤ 8% Aggregates | 98.30 5.07 | 98.26 5.23 | 97.80 0.70 |
| Total free PEG by RP-HPLC | ≤ 6.0 mg/mL | <0.07 | <0.07 | 0.74 |
| Free 10K PEG by RP-HPLC | ≤ 0.6 mg/mL | <0.07 | <0.07 | <0.07 |
| N-Hydroxysuccinimide (NHS) | ≤ 6.0 ppm | Not tested | 1.87 | 0.65 |
| Modification by 2,4,6-Trinitrobenzenesulfonic acid (TNBS) | 69-82 moles PEG/mole protein | Not tested | 76 | 73 |
| Endotoxin | ≤ 35 EU/mL | <5 | <5 | <5 |
| Bioburden | ≤ 2 CFU/20 mL | 0 | 0 | 0 |
| Sterility (performed after sterile filtration) | Passes USP | Not tested | Not tested | Complies |

*values taken from testing of samples post-diafiltration/pre-dilution

Dilution

The in-process material was mixed in the 7 gallon stainless steel pressure vessel before samples were pulled for activity and protein testing. The volume of in-process material was then diluted with PBS to bring the protein concentration to a target value of ≥ 18.0 mg/mL (target 20.0 mg/mL), (≥ 1850 IU/mL activity) for the drug substance intended for the lyophilized composition. The diluted in-process material was then mixed before samples were removed for quality assurance testing (see Table 1).

Sterile Filtration

The concentrated solution for lyophilization was filtered at 0.2 μm into a disposable 20 L sterile bag for storage until lyophilization was performed. A sample was collected and submitted for sterility testing. The bulk drug substance composition that included the polyethylene glycol-asparaginase for lyophilization may be held in the 20 L bag at 2-8° C. for up to 2 months prior to lyophilization.

Container Closure

The bulk drug substance composition that included the polyethylene glycol-asparaginase for lyophilization was processed into lyophilized composition following the 0.2 μm filtration step and delivery into a disposable pre-sterilized 20 L bioprocess bag. The material of construction of the bag included of layers of low-density polyethylene (LDPE), linear low-density polyethylene (LLDPE), nylon, and ethylene vinyl alcohol (EVOH). The direct product contact surface (inner layer) was LDPE. Each bag had two openings with attached tubing that was fixed to the bag and was crimped closed with clamps until it was ready to receive the bulk drug substance composition that included the polyethylene glycol-asparaginase for lyophilization. The bags were irradiated and released based on exposure of 25-40 kGy, and underwent Limulus Amebocyte Lysate (LAL) endotoxin testing, 100% visual seal and air leak testing, as well as a 100% visual inspection following assembly. The results of qualification testing showed that the inner layer of the bag passed biological reactivity tests, including USP <88> Class IV plastics testing, USP <87> cytotoxicity testing, and USP <661> testing of physiochemical attributes. In addition, the bags complied with USP <788> for particulate matter in injections and all extractable testing conformed to the manufacturer's requirements.

Drug Substance Stability Hold Times

The concentrated bulk drug substance material was monitored at 0, 2, 4, 6, 8, and 12 weeks at 2-8° C. Stability samples were maintained in 250 mL sample bags with product contact surface of polyethylene. Data from the testing plan is presented in Table 3 for Lot 1, Table 4 for Lot 2, and Table 5 for Lot 3.

The stability data for the concentrated bulk drug substance intended for lyophilized compositions met the acceptance criteria throughout the 12 week testing plan and indicated that a 2 month hold time between concentrated bulk drug substance production and the production of the lyophilized composition was acceptable.

TABLE 3

Stability Data for Lot 1 Stored at 2-8° C.

| Test | Acceptance Criteria | Initial | 2 | 4 | 6 | 8 | 12 |
|---|---|---|---|---|---|---|---|
| | | | | Time (Weeks) | | | |
| Protein concentration | ≥ 18.0 mg/mL | 20.94 | 21.31 | 21.31 | 21.18 | 21.15 | 21.34 |
| Potency (activity) | ≥ 1850 IU/mL | 2305 | 2413 | 2448 | 2432 | 2498 | 2538 |
| Appearance | Colorless solution | Complies | Complies | Complies | Complies | Complies | Complies |
| Clarity | Clear, no visible particles | Complies | Complies | Complies | Complies | Complies | Complies |
| pH | 7.2 to 7.4 | 7.2 | 7.2 | 7.2 | 7.2 | 7.2 | 7.3 |
| Specific activity | ≥ 85 IU/mg of protein | 110 | 113 | 115 | 115 | 118 | 119 |
| Purity by GF-HPLC | ≥ 95% Active components; ≤ 8% Aggregates | 98.30, 5.07 | 97.83, 4.48 | 98.99, 4.38 | 99.24, 4.39 | 98.14, 4.43 | 97.34, 3.36 |
| Free 10K PEG by RP-HPLC | ≤ 0.6 mg/mL | <0.07 | <0.07 | <0.07 | 0.24 | 0.24 | 0.33 |
| Total free PEG by RP-HPLC | ≤ 6.0 mg/mL | 0.07 | 3.03 | 2.41 | 3.07 | 3.11 | 4.19 |
| N-Hydroxysuccinimide (NHS) | ≤ 6.0 mg/mL | Not tested | 2.23 | 2.31 | 2.31 | 2.32 | 2.34 |
| Modification by TNBS | 69-82 moles PEG/mole protein | Not tested | 76 | 75 | 76 | 74 | 73 |

TABLE 4

Stability Data for Lot 2 Stored at 2-8° C.

| Test | Acceptance Criteria | Initial | 2 | 4 | 6 | 8 | 12 |
|---|---|---|---|---|---|---|---|
| | | | | Time (Weeks) | | | |
| Protein concentration | ≥ 18.0 mg/mL | 19.65* | 20.28 | 20.11 | 19.82 | 20.25 | 20.09 |
| Potency (activity) | ≥ 1850 IU/mL | 2279* | 2248 | 2263 | 2344 | 2360 | 2426 |
| Appearance | Colorless solution | Complies | Complies | Complies | Complies | Complies | Complies |
| Clarity | Clear, no visible particles | Complies | Complies | Complies | Complies | Complies | Complies |
| pH | 7.2 to 7.4 | 7.2 | 7.2 | 7.2 | 7.3 | 7.2 | 7.2 |
| Specific activity | ≥ 85 IU/mg of protein | 116 | 111 | 113 | 118 | 117 | 128 |
| Purity by GF-HPLC | ≥ 95% Active components; ≤ 8% Aggregates | 98.26, 5.23 | 98.17, 5.19 | 98.16, 4.71 | 98.27, 4.79 | 97.19, 4.21 | 98.24, 4.30 |
| Free 10K PEG by RP-HPLC | ≤ 0.6 mg/mL | <0.07 | 0.27 | 0.33 | 0.37 | 0.44 | 0.47 |
| Total free PEG by RP-HPLC | ≤ 6.0 mg/mL | <0.07 | 1.25 | 2.05 | 2.75 | 4.15 | 4.50 |
| N-Hydroxysuccinimide (NHS) | ≤ 6.0 mg/mL | 1.87 | 2.55 | 2.76 | 2.79 | 2.82 | 2.83 |
| Modification by TNBS | 69-82 moles PEG/mole protein | 76 | 74 | 78 | 75 | 75 | 76 | values taken from test mg of samples post-diafiltration/pre-dilution

TABLE 5

Stability Data for Lot 3 Stored at 2-8° C.

| Test | Acceptance Criteria | Initial | 2 | 4 | 6 | 8 | 12 |
|---|---|---|---|---|---|---|---|
| Protein concentration | ≥ 18.0 mg/mL | 18.39 | 17.79 | 18.22 | 18.20 | 18.56 | 18.49 |
| Potency (activity) | ≥ 1850 IU/mL | 2091 | 2212 | 2256 | 2202 | 2199 | 2290 |
| Appearance | Colorless solution | Complies | Complies | Complies | Complies | Complies | Complies |
| Clarity | Clear, no visible particles | Complies | Complies | Complies | Complies | Complies | Complies |
| pH | 7.2 to 7.4 | 7.2 | 7.3 | 7.2 | 7.3 | 7.3 | 7.3 |
| Specific activity | ≥ 85 IU/mg of protein | 114 | 124 | 124 | 121 | 118 | 124 |
| Purity by GF-HPLC | ≥ 95% Active components; ≤ 8% Aggregates | 97.80, 0.7 | 98.00, 0.65 | 97.61, 0 | 97.76, 0 | 97.24, 0.55 | 97.94, 0 |
| Free 10K PEG by RP-HPLC | ≤ 0.6 mg/mL | <0.07 | <0.07 | <0.07 | <0.07 | 0.07 | <0.07 |
| Total free PEG by RP-HPLC | ≤ 6.0 mg/mL | <0.07 | 2.23 | 2.00 | 3.00 | 3.98 | 5.00 |
| N-Hydroxysuccinimide (NHS) | ≤ 6.0 mg/mL | 0.65 | 0.70 | 0.70 | 0.70 | 0.68 | 0.64 |
| Modification by TNBS | 69-82 moles PEG/mole protein | 73 | Not tested | 70 | 70 | 74 | 76 |

Lyophilized Composition

The lyophilized composition powder for injection was produced in a single-use vial containing 3,750 IU of active PEGylated L-asparaginase (750 IU/mL after reconstitution with 5.2 mL of WFI). The components of the lyophilized composition included 4.5% sucrose, dibasic sodium phosphate, monobasic sodium phosphate, and sodium chloride after reconstitution. The composition of the lyophilized composition is provided in Table 6. In addition, the lyophilized composition was provided in a treated glass vials container (Nipro Type 1) having a 20 mm aluminum flip-off seal.

TABLE 6

Components of the Polyethylene Glycol-Asparaginase Composition

| Component | Grade | Amount per g* |
|---|---|---|
| Polyethylene glycol-asparagınase | n/a | 750 IU |
| Dibasic sodium phosphate | USP | 2.79 mg |
| Monobasic sodium phosphate | USP | 0.60 mg |
| Sodium Chloride | USP | 4.25 mg |
| Sucrose | National Formulary (NF) | 45 mg |
| Water for injection (WFI) | USP | QS to 1.0 g |

*values are post reconstituted with WFI

Formulation Development of Lyophilized Polyethylene Glycol-Asparaginase

The objective of developing a lyophilized polyethylene glycol-asparaginase formulation was to attain a stable lyophilized composition that was suitable for 2-8° C. or 25° C. storage for at least 18 months.

Initial experiments to assess the feasibility of a lyophilized composition of polyethylene glycol-asparaginase were performed. Five variations of lyophilized compositions were investigated. Each formulation contained ~5 mg/mL of polyethylene glycol-asparaginase in 50 mM phosphate buffer, pH 6.5 and 5% w/v of one of five different cryoprotectants (mannitol, maltose, sucrose, trehalose, and/or -HPCD). In addition, polyethylene glycol-asparaginase without a cryoprotectant was also subjected to lyophilization. These six lyophilized compositions were compared to a lot of polyethylene glycol-asparaginase in liquid formulation (Oncaspar®) that was used for preparation of these different formulations. SEC-Purity (GF-HPLC) method was used for assessing the quality of the polyethylene glycol-asparaginase compositions. The results of the study are presented in Table 7. As seen from Table 7, sucrose was found to be most effective at preserving purity of polyethylene glycol-asparaginase during lyophilization. Purity (83.0%) of the lyophilized composition with 5% sucrose was comparable to purity (83.8%) of the liquid polyethylene glycol-asparaginase formulation that was used for the preparation of the six formulations for the subsequent lyophilization.

TABLE 7

Results of Feasibility Study for Lyophilizing Polyethylene Glycol-Asparaginase

| | % Purity (SEC-HPLC; RT-minutes) | | | | |
|---|---|---|---|---|---|
| Composition[1] | 10.0 | 10.2 | 10.5 | 11.2[2] | 12.0 |
| Oncaspar (Control, liquid composition) | — | — | 3.0 | 83.8 | 13.2 |
| 5% Mannitol | — | 0.9 | 1.4 | 74.7 | 23.1 |
| 5% Maltose | — | 0.9 | 2.3 | 78.8 | 17.9 |
| 5% Sucrose | — | — | 3.1 | 83.0 | 14.0 |
| 5% Trehalose | — | — | 3.2 | 79.5 | 17.3 |
| 5%-HPCD | — | — | 2.9 | 78.9 | 18.3 |
| lyophilized, no preservative | 0.4 | 0.8 | 9.4 | 65.7 | 23.7 |

[1]All formulations also contained ~5 mL Oncaspar in 5 mM phosphate buffer, pH 6.5
[2]expected retention time of Oncaspar Several different excipients (e.g., sucrose, trehalose, mannitol, polysorbate 80) were evaluated as potential stabilizing agents to include in the lyophilized composition. Four experiments, each including four different compositions, were performed. Small pilot scale lyophilized polyethylene glycol-asparaginase batches were prepared with the different excipients and evaluated for stability. A list of formulations that were tested is shown in Table 8.

TABLE 8

Polyethylene Glycol-Asparaginase Compositions Tested

| Lot | Composition |
|---|---|
| 1A | 5% Sucrose, 12.5 mg/mL PEG-asparginase, Phosphate Buffer |
| 1B | 2.5% Sucrose, 2.5% Mannitol, 12.5 mg/mL PEG-asparginase, Phosphate Buffer |
| 1C | 2.5% Sucrose, 2.5% Mannitol, 0.01% Polysorbate-80, 12.5 mg/mL PEG-asparginase, Phosphate Buffer |
| 1D | 5% Sucrose, 0.01% Polysorbate-80, 12.5 mg/mL PEG-asparginase, Phosphate Buffer |
| 2A | 5% Trehalose, 12.5 mg/mL PEG-asparginase, Phosphate Buffer |
| 2B | 2.5% Trehalose, 2.5% Mannitol, 12.5 mg/mL PEG-asparginase, Phosphate Buffer |
| 2C | 2.5% Trehalose, 2.5% Mannitol, 0.01% Polysorbate-80, 12.5 mg/mL PEG-asparginase, Phosphate Buffer |
| 2D | 5% Trehalose, 0.01% Polysorbate-80, 12.5 mg/mL-asparginase, Phosphate Buffer |
| 3A | 5% Sucrose, 6.5 mg/mL PEG-asparginase, Phosphate Buffer |
| 3B | 2.5% Sucrose, 2.5% Mannitol, 6.5 mg/mL L-Asparginase, Phosphate Buffer |
| 3C | 2.5% Sucrose, 2.5% Mannitol, 0.01% Polysorbate-80, 6.5 mg/mL LAsparginase, Phosphate Buffer |
| 3D | 5% Sucrose, 0.01% Polysorbate-80, 6.5 mg/mL L-Asparginase, Phosphate Buffer |
| 4A | 5% Trehalose, 6.5 mg/mL L-asparginase, Phosphate Buffer |
| 4B | 2.5% Trehalose, 2.5% Mannitol, 6.5 mg/mL L-Asparginase, Phosphate Buffer |
| 4C | 2.5% Trehalose, 2.5% Mannitol, 0.01% Polysorbate-80, 6.5 mg/mL L-Asparginase, Phosphate Buffer |
| 4D | 5% Trehalose, 0.01% Polysorbate-80, 6.5 mg/mL L-Asparginase, Phosphate Buffer |

All of the lots described in Table 8 were evaluated in stability tests at 5° C., 25° C. and 40° C., and evaluated with a panel of tests (Activity, Specific Activity, Protein, pH, Purity (GF-HPLC), Aggregates (GF-HPLC), and Particulates), that assessed the primary quality attributes of polyethylene glycol-asparaginase at release and on stability. Based these analyses of the stability data collected from the 16 different formulations described in Table 8, sucrose was identified as a suitable cryoprotectant (e.g., stabilizing agent).

Various sucrose concentrations were tested to evaluate the concentration suitable for a more robust (i.e., less impactful lyophilization protocol) and a more stable product. Additional pilot scale batches were prepared containing different concentrations of sucrose, as summarized in Table 9. The sucrose and PEG-asparaginase concentrations shown in Table 9 show the amounts present in the concentrated bulk drug substance. During the lyophilization process, vials were filled at 2.5 mL prior to initiating lyophilization. These lyophilized vials were reconstituted with 5.0 mL, resulting in final sucrose and PEG-asparaginase concentrations that were approximately half those shown in the table. This study demonstrated that the increase in sugar content allowed for higher lyophilization temperatures, which was less stressful for the lyophilized product, and also reduced the overall lyophilization cycle time and resulted in a drier (more stable) lyophilized product.

TABLE 9

Sucrose Compositions Tested

| Lot | Phosphate Buffer (M) | NaCl (%) | Sucrose (mg/mL)1 | PEG-Asparaginase (me/mL)1 |
|---|---|---|---|---|
| SA | 0.1 | 0.85 | 10 (1%) | 12.5 |
| SB | 0.1 | 0.85 | 25 (2.5%) | 12.5 |
| SC | 0.1 | 0.85 | 50 (5%) | 12.5 |
| SD | 0.1 | 0.85 | 75 (7.5%) | 12.5 |
| SE | 0.1 | 0.85 | 100 (10%) | 12.5 |

1Concentration during lyophilization in 2.5 mL/vial. The concentration decreased in half after the reconstitution of the final product with 5 mL/vial of WFI.

Figure 2:
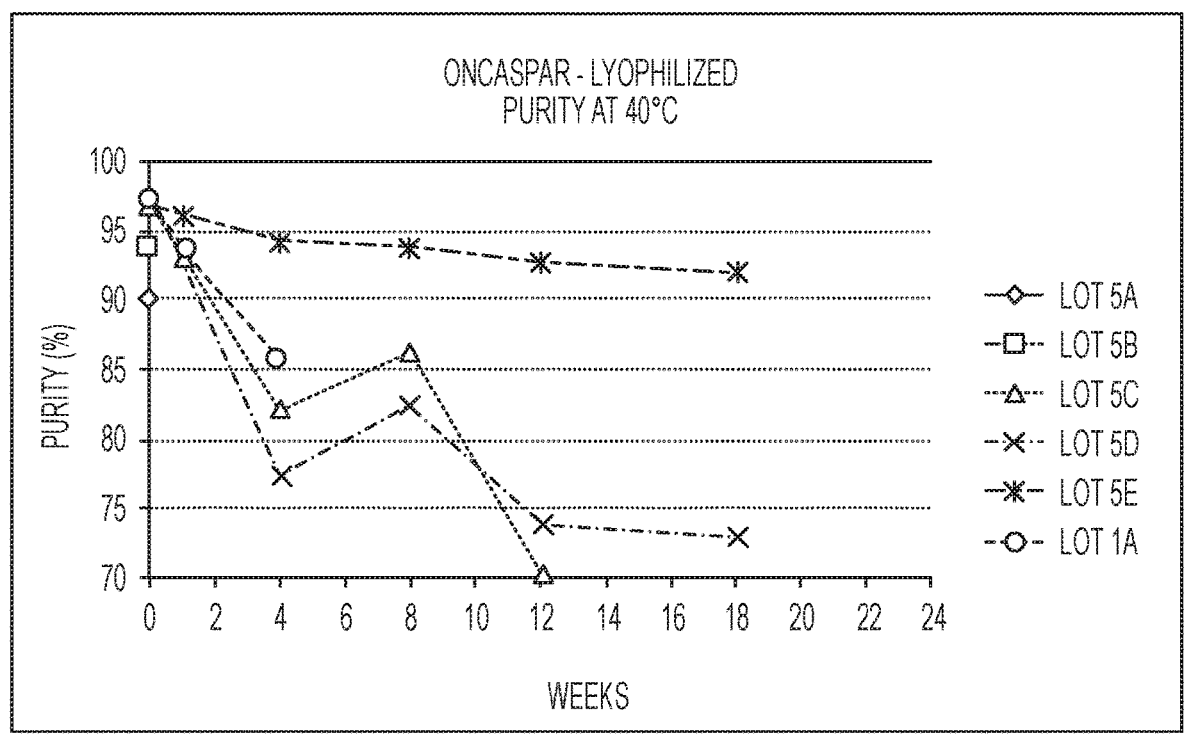
FIG. 2 shows a graph of purity (%) vs. time (weeks) at 40° C. for a lyophilized storage stable composition according to embodiments of the present disclosure.
Figure 3:
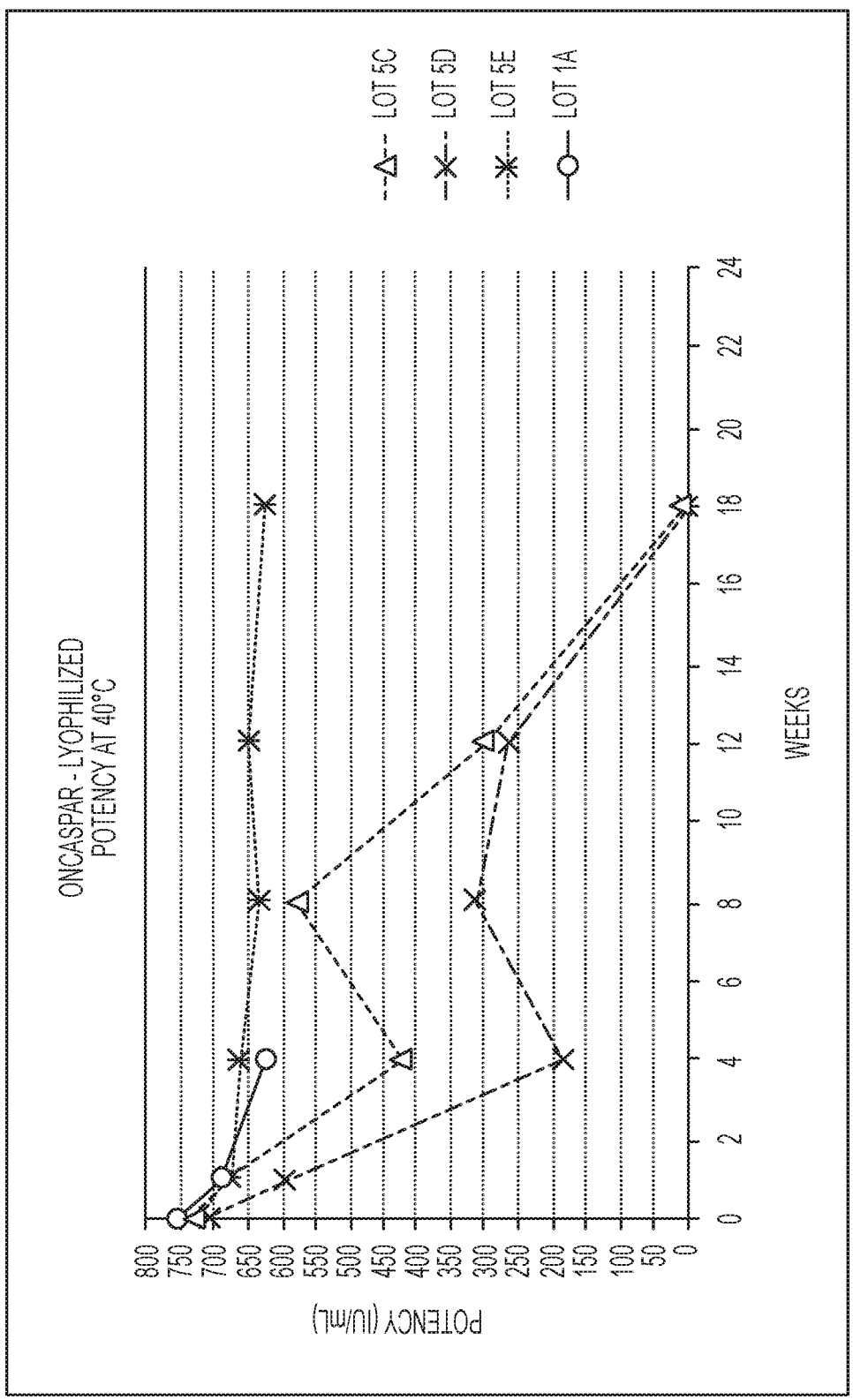
FIG. 3 shows a graph of potency (IU/mL) vs. time (weeks) at 40° C. for a lyophilized storage stable composition according to embodiments of the present disclosure.
Figure 4:
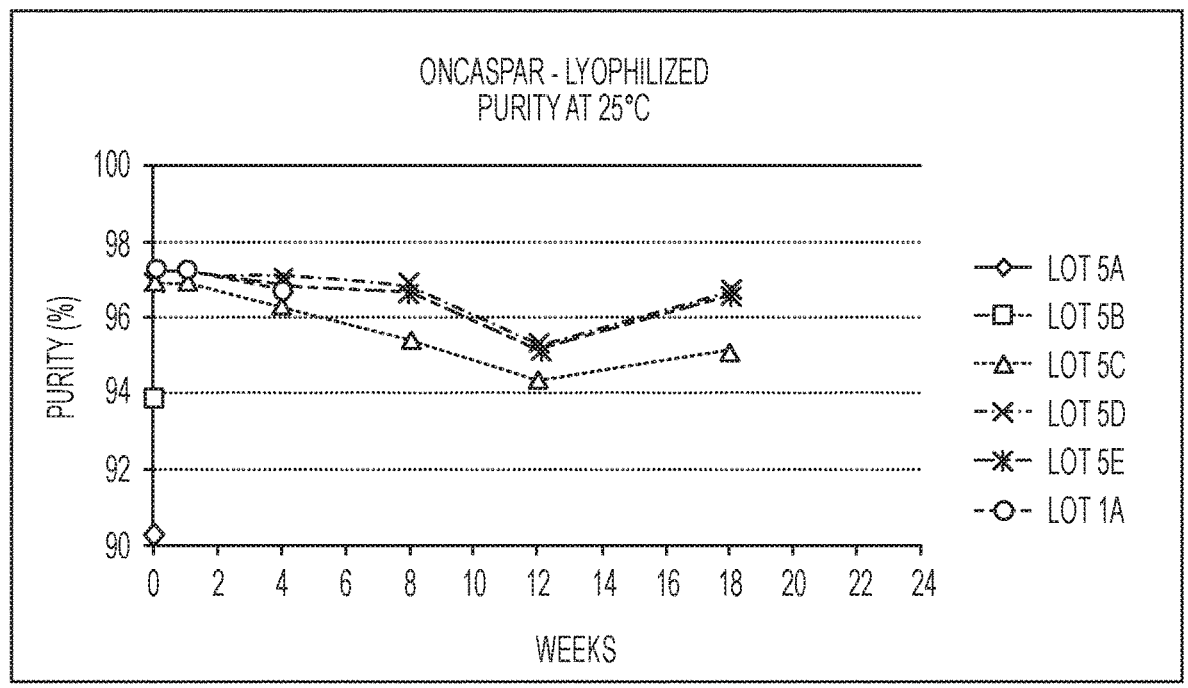
FIG. 4 shows a graph of purity (%) vs. time (weeks) at 25° C. for a lyophilized storage stable composition according to embodiments of the present disclosure.
Figure 5:
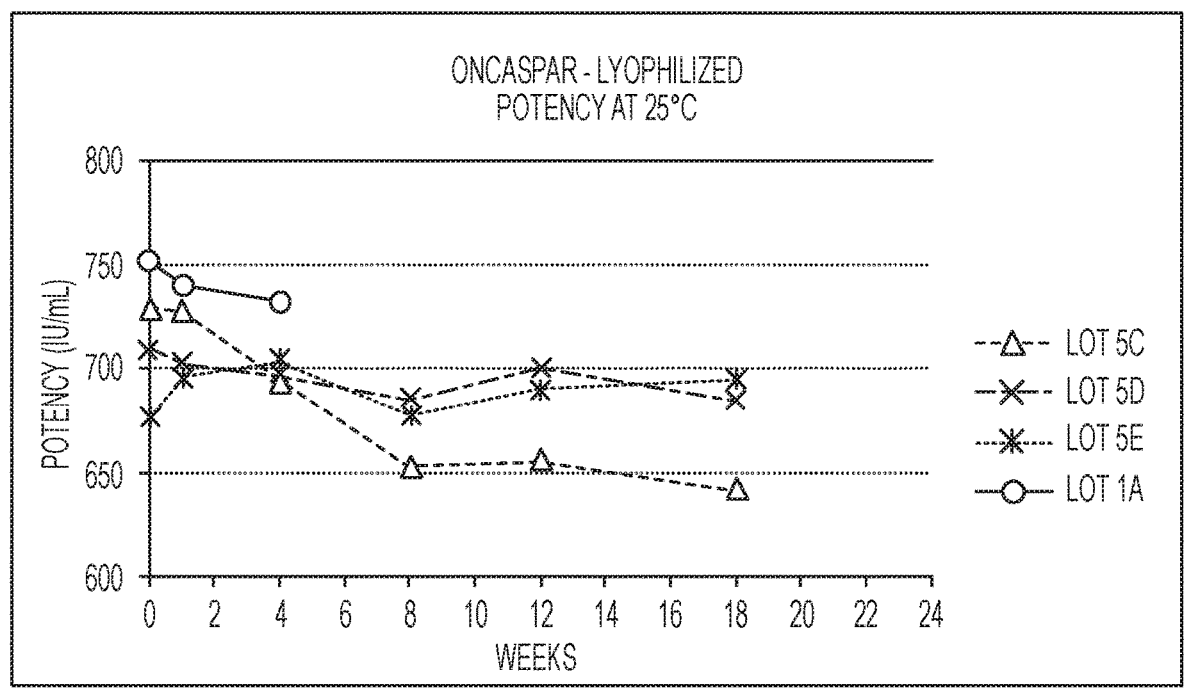
FIG. 5 shows a graph of potency (IU/mL) vs. time (weeks) at 25° C. for a lyophilized storage stable composition according to embodiments of the present disclosure.

The five lots described in Table 9 were also evaluated in stability tests at 5° C., 25° C. and 40° C. Quality attributes such as Activity, Specific Activity, Protein, pH, Purity (GF-HPLC), Aggregates (GF-HPLC), and Particulates were evaluated during this stability study. Purity and Potency results from accelerated (25° C.) and stressed (40° C.) stability studies for these lots are shown in FIGS. 2-5. These stability data indicated that the formulation containing 10% sucrose (5% sucrose after the reconstitution of the final product with 5 mL/vial of WFI) provided a product with the best stability in regards to purity and potency. Other quality attributes were less affected by different formulations, and also were stable in the lot with 10% sucrose. FIG. 2 shows a graph of purity (%) vs. time (weeks) at 40° C. for lyophilized PEG-asparaginase compositions of Lots SA, SB, SC, SD, SE and IA FIG. 3 shows a graph of potency (IU/mL) vs. time (weeks) at 40° C. for lyophilized PEG-asparaginase compositions of Lots SC, SD, SE and IA FIG. 4 shows a graph of purity (%) vs. time (weeks) at 25° C. for lyophilized PEG-asparaginase compositions of Lots SA, SB, SC, SD, SE and IA FIG. 5 shows a graph of potency (IU/mL) vs. time (weeks) at 25° C. for lyophilized PEG-asparaginase compositions of Lots SC, SD, SE and IA Lyophilization A buffer was prepared that included water for injection (WFI), dibasic sodium phosphate, monobasic sodium phosphate, sodium chloride, and sucrose. The buffer was used for dilution of the concentrated bulk drug substance.

WFI was added to a beaker at 90% of the target weight required to produce the buffer solution. Sodium phosphate monobasic, sodium phosphate dibasic, and sodium chloride were then individually weighed and added to the WFI and mixed until dissolved. The required quantity of sucrose was weighed and added to the mixing buffer solution and mixed until dissolved. The pH of the solution was then measured and adjusted to 7.3±0.1 with slow addition of NaOH. WFI was added to the buffer solution as needed, and the density of the concentrated bulk solution was used to weigh the required volume of concentrated bulk solution needed for the batch size. A sample of the buffer was collected for a sucrose assay. The concentrated bulk solution was added to the buffer solution and the final solution was mixed for not less than (NLT) 10 minutes. Upon completion of mixing, confirmatory pH measurements (7.3±0.1) were obtained from the top, middle, and bottom of the vessel, and samples were collected for protein, density, sucrose, and pre-filtration bioburden in-process testing.

Following final formulation the solution underwent sterile filtration. Previously sterilized filtration tubing assembly was placed in the formulated bulk vessel and the bulk was then filtered through two 0.22 µm filters located on the filtration tubing assembly into a pre-sterilized 10 L bioprocess bag in preparation for filling. Once the entire product was transferred to the 10 L bioprocess bag, the filtration tubing assembly was disconnected from the bioprocess bag and the filters were tested for integrity. One 20 mL pre-lyophilization sample was collected from the filter upstream (unfiltered) and tested per finished drug product specifications.

Figure 6:
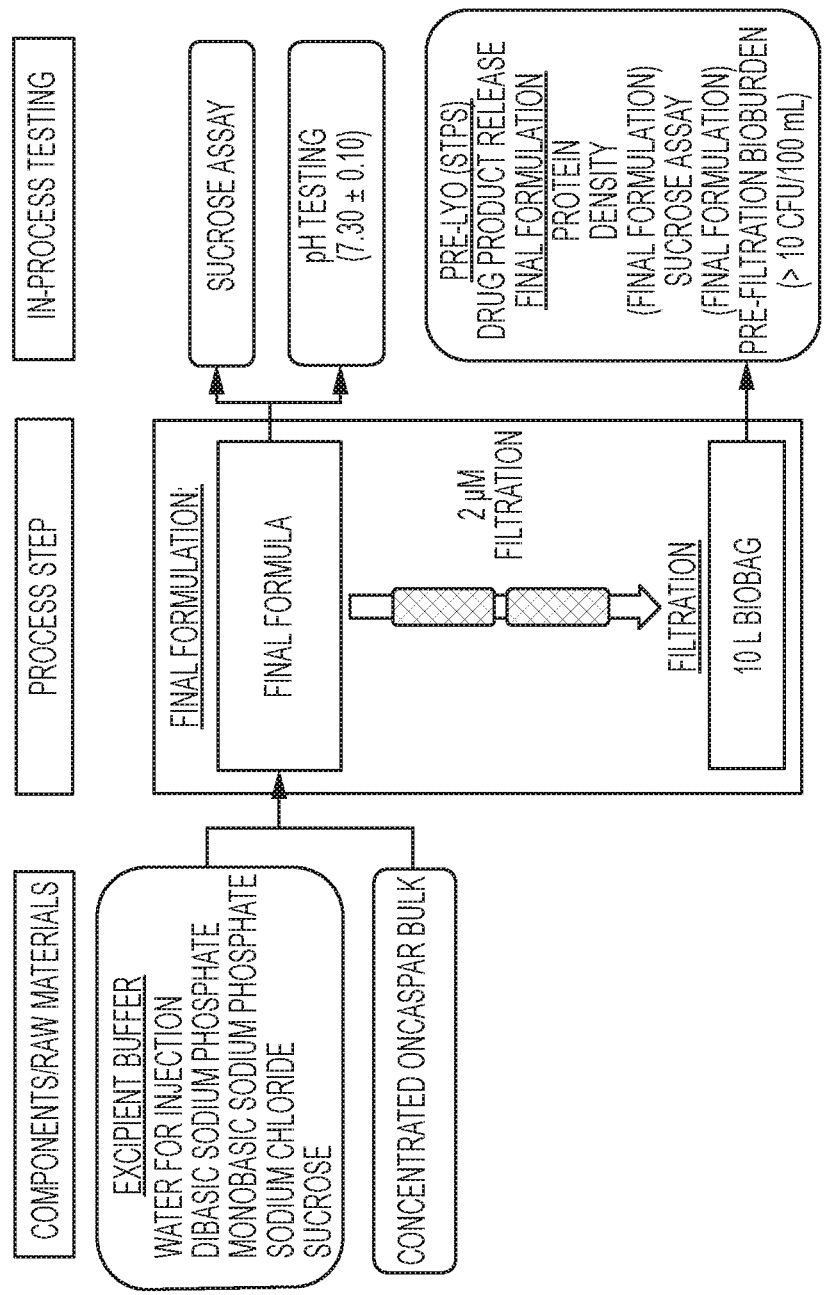
FIG. 6 shows a process flow diagram of a method of making a lyophilized storage stable composition, according to embodiments of the present disclosure. The final formulation and filtration steps are shown.

A flow diagram illustrating the final formulation and sterile filtration process step is shown in FIG. 6.

Aseptic Filling and Lyophilization

Following the completion of sterile filtration, the 10 L biobag containing the bulk API solution was connected to the fill tubing assembly and the product vials were then filled at a target fill weight of 2.5 g/vial and partially stoppered using the Flexicon FMB210 filler. Fill weights were monitored by performing a minimum of one weight check (1 vial) for every tray filled (action limit: 2.43-2.57 g, alert limit: 2.38-2.62 g) during the filling operation. When the filling operation was complete, 20 pre-lyophilized vials were tested and all remaining filled vials were transferred into stainless steel lyophilization trays and subsequently loaded into a pre-chilled (5° C.) 270 ft² Hull freeze-drying system for lyophilization. The lyophilization process included the phases shown in Table 10.

TABLE 10

Lyophilization Cycle-Process Parameters

Thermal Treatment Phase

| Step | Temp. (° C.) | Ramp Time (minutes) | Soak Time (minutes) |
|---|---|---|---|
| 1 | 5 | 0 | 30 |
| 2 | −45 | 100 | 120 |

Freeze Condenser and Evacuate Phase

| Condenser S.P. | −45° C. |
|---|---|
| Evacuate S.P. | 60 mT |

TABLE 10-continued

Lyophilization Cycle-Process Parameters

Primary Dry Phase

| Step | Temp. (° C.) | Ramp Time (minutes) | Soak Time (minutes) | Vac. Cont. S.P. (mT) |
|---|---|---|---|---|
| 1 | −45 | 0 | 30 | 50 |
| 2 | −28 | 60 | 3860 | 50 |

Secondary Dry Phase

| Step | Temp. (° C.) | Ramp Time (minutes) | Soak Time (minutes) | Vac. Cont. S.P. (mT) |
|---|---|---|---|---|
| 1 | 35 | 630 | 1920 | 50 |

Figure 7:
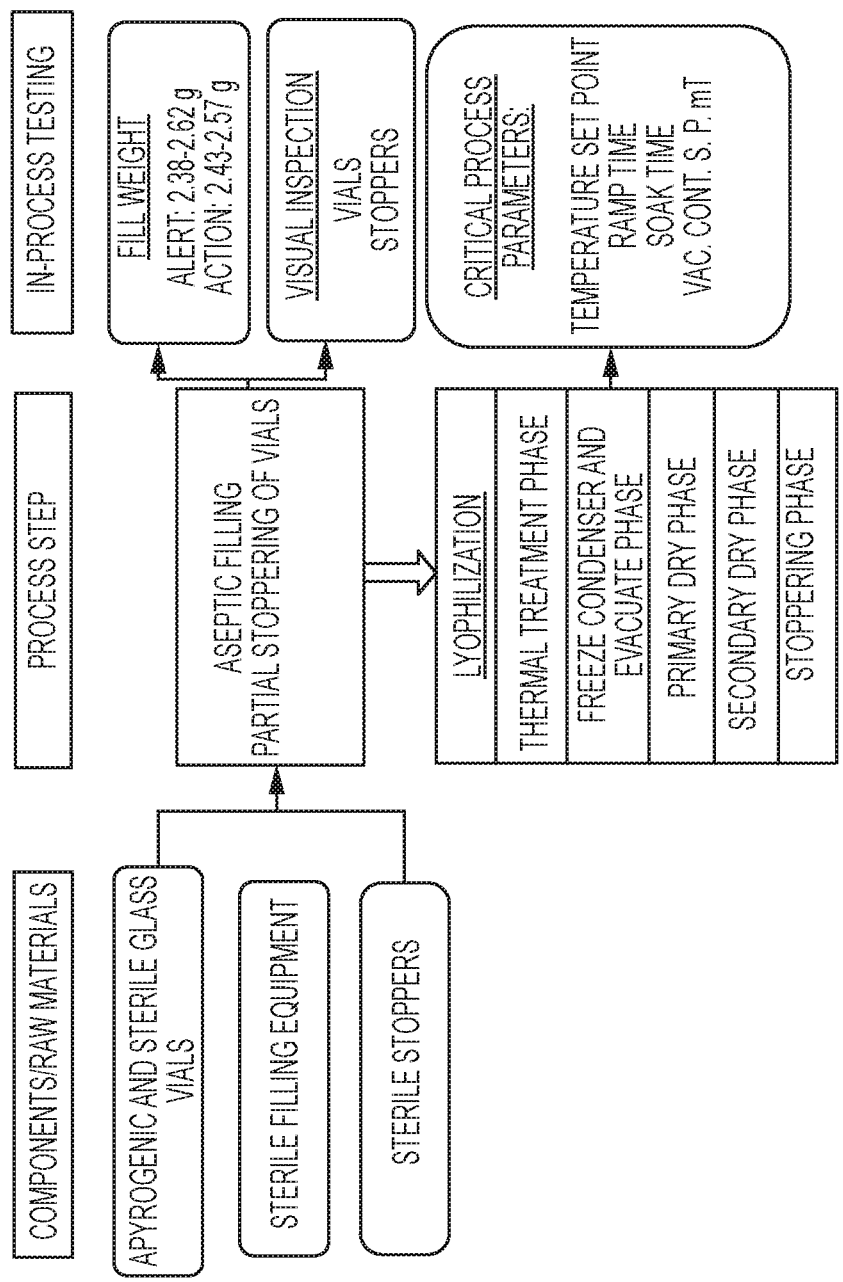
FIG. 7 shows a process flow diagram of a method of making a lyophilized storage stable composition, according to embodiments of the present disclosure. The aseptic filling and lyophilization steps are shown.

After the lyophilization cycle was complete, the evacuated chamber was backfilled with nitrogen gas and the vials were fully stoppered. A flow diagram illustrating the aseptic filling and lyophilization process step is shown in FIG. 7. The fully stoppered vials were then packaged into cartons (90 vials/carton) and then stored and/or shipped.

Lyophilized Composition Specifications

The product specifications for the lyophilized composition are shown in Table 11.

TABLE 11

Specifications for Lyophilized Composition

| Test | Method | Acceptance Criteria Lyophilized Composition[1] |
|---|---|---|
| Appearance | ACM-1504 | White to off white cake (pre-reconstitution); Colorless solution after reconstitution |
| Clarity | | Clear, no visible particles after reconstitution |
| Fill volume | | To deliver 5.0 mL (USP) |
| pH | | 7.2-7.4 |
| Potency (activity) | RDM-10004 | 600-900 IU/mL |
| Specific activity | ACM-1510 | 2: 85 IU/mg protein |
| | ACM-1517 | 2: 95% active components |
| Purity by GF-HPLC | RDM-10006 | :S 8% aggregates |
| Total free PEG by RP-HPLC | ACM-1509 RDM-10007 | :S 2.0 mg/mL |
| Free 10K PEG by RP-HPLC | | :S 0.2 mg/mL |
| N-Hydroxysuccinimide (NHS) | ACM-1505 | :S 2.0 ppm |
| Modification by TNBS | ACM-1507 RDM-10015 | 69-82 moles PEG/mole protein |
| Protein concentration | ACM-1506 RDM-10005 | 4.5-8.5 mg/mL |
| Sterility | USP <71> | Pass USP sterility test |
| General safety | USP <88> 21 CFR 610.11 | Pass USP test in Guinea Pig Pass USP test in mice |
| Endotoxin by LAL | ACM-1511 | :S 35 EU/mL |
| Particulate matter | ACM-0070 | 2: 2 µm NMT 27,000 Particles/Container[1] 2: 10 µm NMT 6000 Particles/Container 2: 25 µm NMT 600 Particles/Container |
| Identity test | ACM-1805 | Deaminates asparagine |
| Content uniformity | RDM-10004 | Complies with USP |
| Reconstitution time | LSNE SOP CQC032[1] | NMT 3 minutes |
| Water (KF) | LSNE SOP CQC0320 | NMT 3.0% |

[1]With the exception of pre-reconstitution appearance testing, all testing was performed post-reconstitution with WFI;

Lot Analyses

Lot analyses for lyophilized composition product lots are provided in Table 12 below. Results for all three lots were within release specifications.

TABLE 12

Lot Analyses for Lyophilized Compositions

| Test | Acceptance Criteria | Lot 1 | Lot 2 | Lot 3 |
|---|---|---|---|---|
| Appearance | White to off white cake | Complies | Complies | Complies |
| Appearance after reconstitution | Colorless solution | Complies | Complies | Complies |
| Clarity after reconstitution | Clear, no visible particles after reconstitution | Complies | Complies | Complies |
| Fill volume | To deliver 5.0 mL (USP) | 5.5 | 5.4 | 5.2 |
| pH | 7.2-7.4 | 7.4 | 7.4 | 7.4 |
| Potency (activity) | 600-900 IU/mL | 805 | 718 | 741 |
| Specific activity | ≥ 85 IU/mg protein | 114 | 111 | 113 |
| Purity by GF-HPLC | ≥ 95% active components | 97 | 97 | 97 |
|  | ≤ 8% aggregates | 5 | 4 | 1 |
| Total free PEG by RP-HPLC | ≤ 2.0 mg/mL | 0.9 | 1.3 | 0.5 |
| Free 10K PEG by RP-HPLC | ≤ 0.2 mg/mL | 0.1 | 0.2 | 0.1 |
| N-Hydroxysuccinimide (NHS) | ≤ 2.0 ppm | 0.1 | 0.9 | 0.2 |
| Modification by TNBS | 69-82 moles PEG/mole protein | 77 | 77 | 75 |
| Protein concentration | 4.5-8.5 mg/mL | 7.1 | 6.5 | 6.6 |
| Sterility | Pass USP sterility test | n/a | Complies | Complies |
| General safety | Pass USP test in Guinea Pig Pass USP test in mice | Conforms | Conforms | Conforms |
| Endotoxin by LAL | ≤ 35 EU/mL | <4 | <4 | <4 |
| Particulate matter | ≥ 2 μm NMT 27,000 Particles/Container | 1835 | 530 | 5834 |
|  | ≥ 10 μm NMT 6000 Particles/Container | 116 | 12 | 96 |
|  | ≥ 25 μm NMT 600 Particles/Container | 1 | 1 | 2 |
| Identity test | Deaminates asparagme | n/a | n/a | n/a |
| Content uniformity | Complies with USP | Complies | Complies | Complies |
| Reconstitution time | NMT 3 minutes | <1 | <1 | <1 |
| Water (KF) | NMT 3.0% | 0.1 | 0.2 | 0.1 |

Stability Studies

Lyophilized drug product Lots 1, 2, and 3 were placed in long-term (2-8° C.) and accelerated (25±3° C.; 60%±5% RH) stability tests. These lots were also placed in Heat Stress stability test (40±2° C.; 75%±5% RH) to assess the product's heat-induced degradation profile.

Long-Term Stability (2-8° C.)

Figure 8:
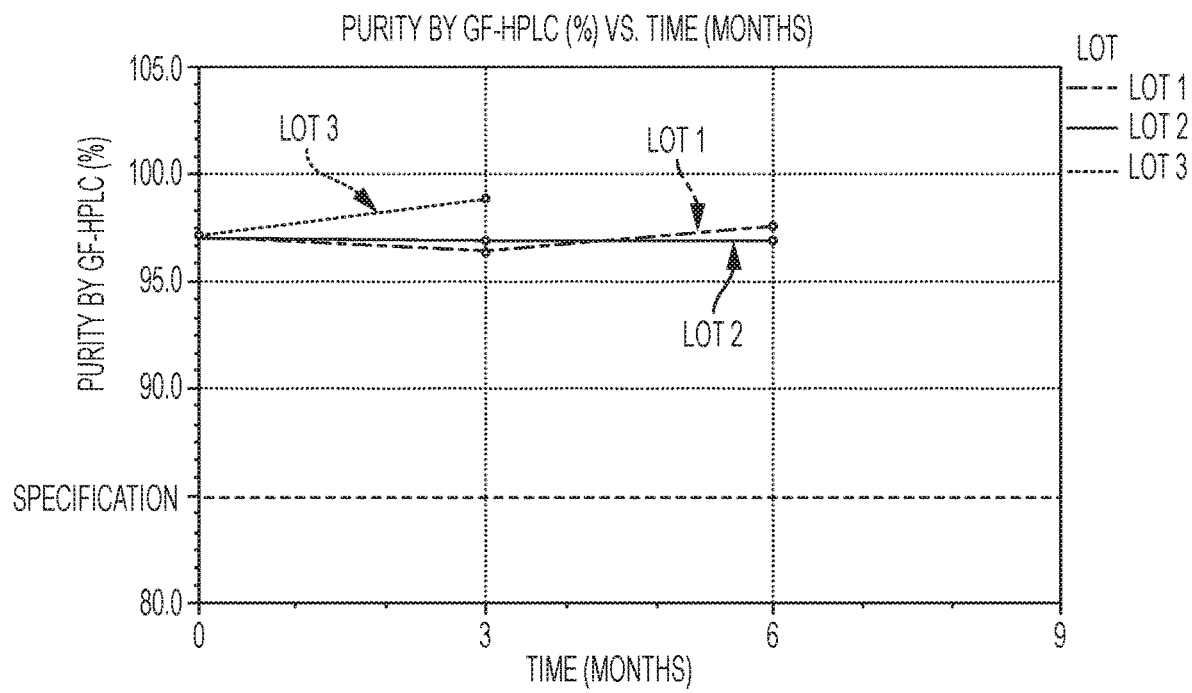
FIG. 8 shows a graph of purity by GF-HPLC (%) vs. time (months) for a lyophilized composition stored at 2-8° C. (e.g., 5° C.), according to embodiments of the present disclosure.
Figure 9:
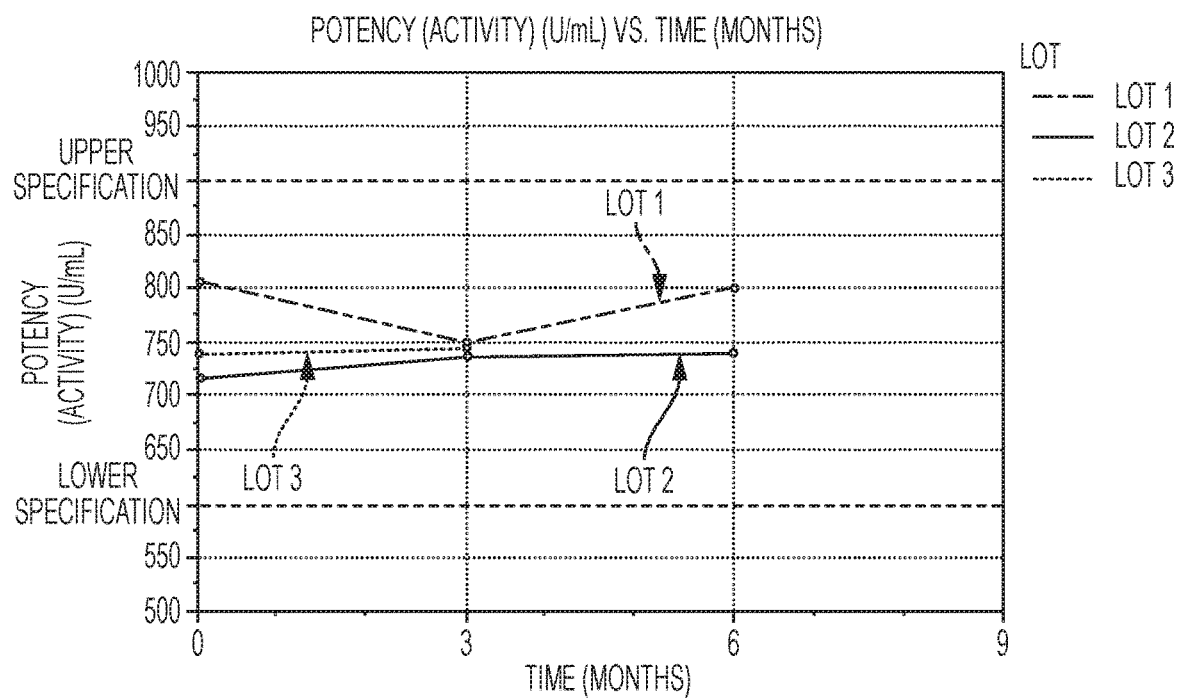
FIG. 9 shows a graph of potency (activity) (IU/mL) vs. time (months) for a lyophilized composition stored at 2-8° C. (e.g., 5° C.), according to embodiments of the present disclosure.
Figure 10:
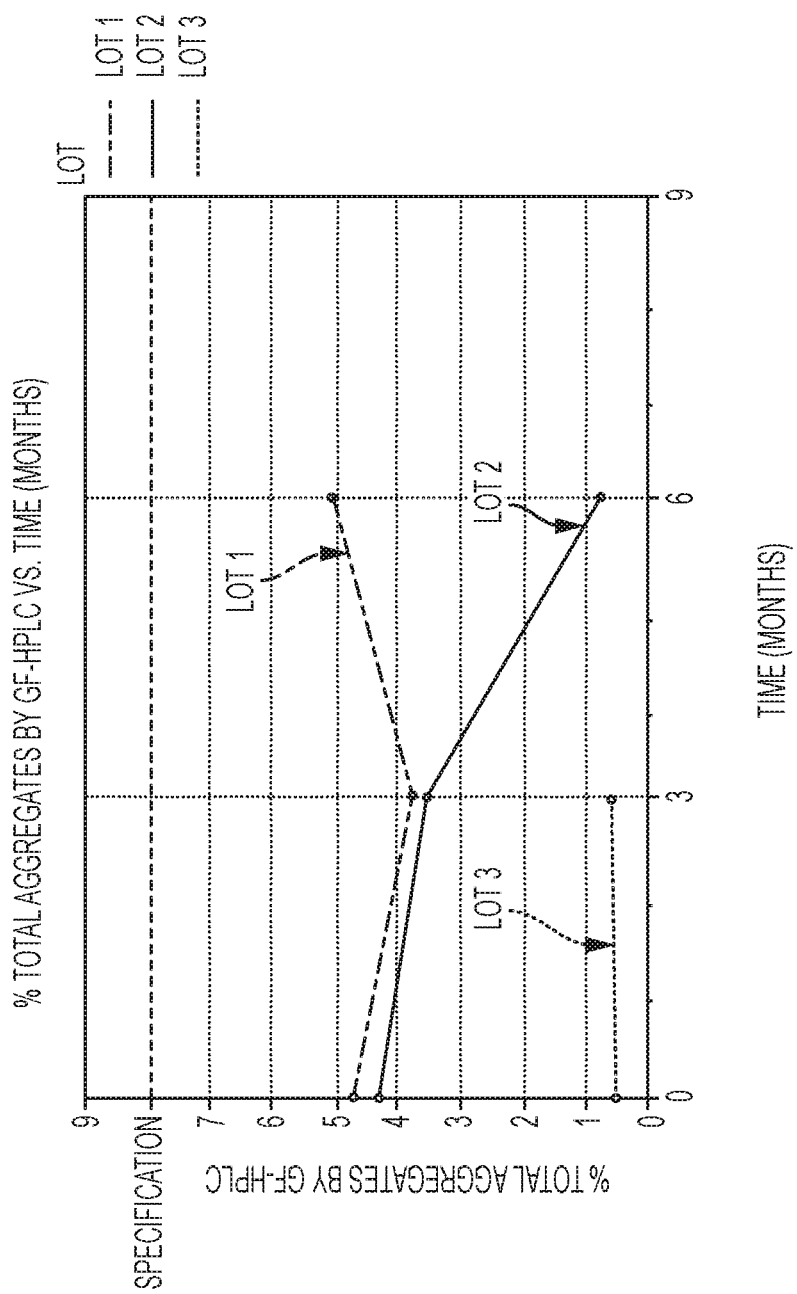
FIG. 10 shows a graph of total aggregates by GF-HPLC vs. time (months) for a lyophilized composition stored at 2-8° C. (e.g., 5° C.), according to embodiments of the present disclosure.

Stability data generated for lyophilized drug product lots stored under long-term (2-8° C.) conditions are provided in Tables 13-16. Long-term stability data indicated that lyophilized drug product stored at 5±3° C. remained well within the acceptance criteria for all stability time points. Water Content (KF) data ranged from 0.96%-1.35% (specification=NMT 3.0%) at the 2-8° C. storage condition through 12 weeks. Unlike commercial liquid drug product, which demonstrated an increase in activity and a decrease in purity over time, this trend was not observed for lyophilized compositions. Stability graphs for the purity (FIG. 8) and potency (FIG. 9), as well as aggregates (FIG. 10), at 2-8° C. shown in the accompanying figures.

TABLE 13

Lot 1 Long Term Stability Data

| | | Time (months) | | |
|---|---|---|---|---|
| Test | Acceptance Criteria | Initial | 3 | 6 | 9 |
| Appearance | White to off white cake; Colorless solution after reconstitution | Conforms | Conforms | Conforms | — |

TABLE 13-continued

Lot 1 Long Term Stability Data

| Test | Acceptance Criteria | Initial | 3 | 6 | 9 |
|---|---|---|---|---|---|
| Clarity | Clear, no visible particles after reconstitution | Conforms | Conforms | Conforms | — |
| pH | 7.2-7.4 | 7.4 | 7.4 | 7.4 | — |
| Potency (activity) | 600-900 IU/mL | 805 | 750 | 801 | — |
| Specific activity | ≥ 85 IU/mg protein | 114 | 107 | 111 | — |
| Purity by GF-HPLC | ≥ 85% active components; ≤ 8% aggregates | 97.07 4.73 | 96.53 3.82 | 97.68 5.05 | — — |
| Total free PEG by RP-HPLC | ≤ 6.0 mg/mL | 0.86 | 0.86 | 1.13 | — |
| Total 10K PEG by RP-HPLC | ≤ 0.6 mg/mL | 0.13 | 0.13 | 0.14 | — |
| Protein concentration | 4.5-8.5 mg/mL | 7.06 | 7.01 | 7.20 | — |
| Particulate matter | 2 μm NMT 27,000 Particles/Container | 1835 | — | — | 204[1] |
|  | 10 μm NMT 6000 Particles/Container | 116 | 21 | 126 | — |
|  | 25 μm NMT 600 Particles/Container | 1 | 0 | 2 | — |
| Reconstitution time | NMT 3 minutes | 0.99 | 0.99 | 0.99 | — |
| Water (KF) | NMT 3.0% | — | — | — | — |

[1]Test was performed at 9 months using MilliQ water for reconstitution of the drug product.

TABLE 14

Lot 2 Long Term Stability Data

| Test | Acceptance Criteria | Initial | 3 | 6 | 9 |
|---|---|---|---|---|---|
| Appearance | White to off white cake; Colorless solution after reconstitution | Conforms | Conforms | Conforms | — |
| Clarity | Clear, no visible particles after reconstitution | Conforms | Conforms | Conforms | — |
| pH | 7.2-7.4 | 7.4 | 7.4 | 7.4 | — |
| Potency (activity) | 600-900 IU/mL | 718 | 738 | 741 | — |
| Specific activity | 85 IU/mg protein | 111 | 115 | 115 | — |
| Purity by GF-HPLC | 85% active components; ≤ 8% aggregates | 97.16 4.35 | 96.94 3.85 | 96.99 0.79 | — — |
| Total free PEG by RP-HPLC | ≤ 6.0 mg/mL | 1.31 | 1.11 | 0.88 | — |
| Total 10K PEG by RP-HPLC | ≤ 0.6 mg/mL | 0.15 | 0.13 | 0.069 | — |
| Protein concentration | 4.5-8.5 mg/mL | 6.48 | 6.44 | 6.44 | — |
| Particulate matter | 2 μm NMT 27,000 Particles/Container | 530 | — | — | 207[1] |
|  | 10 μm NMT 6000 Particles/Container | 12 | 55 | 69 | — |
|  | 25 μm NMT 600 Particles/Container | 1 | 0 | 0 | — |
| Reconstitution time | NMT 3 minutes | 0.99 | 0.99 | 0.99 | — |
| Water (KF) | NMT 3.0% | 0.2% | — | — | — |

[1]Test was performed at 9 months using MilliQ water for reconstitution of the drug product.

TABLE 15

Lot 3 (upright) Long Term Stability Data

| Test | Acceptance Criteria | Initial | 3 | 6 | 9 |
|---|---|---|---|---|---|
| Appearance | White to off white cake; Colorless solution after reconstitution | Conforms | Conforms | — | — |
| Clarity | Clear, no visible particles after reconstitution | Conforms | Conforms | — | — |
| pH | 7.2-7.4 | 7.4 | 7.4 | — | — |
| Potency (activity) | 600-900 IU/mL | 741 | 733 | — | — |
| Specific activity | ≥ 85 IU/mg protein | 113 | 117 | — | — |
| Purity by GF-HPLC | ≥ 85% active components; ≤ 8% aggregates | 97.05 / 0.55 | 98.87 / 0.65 | — | — |
| Total free PEG by RP-HPLC | ≤ 6.0 mg/mL | 0.45 | 1.20 | — | — |
| Total 10K PEG by RP-HPLC | ≤ 0.6 mg/mL | 0.11 | 0.069 | — | — |
| Protein concentration | 4.5-8.5 mg/mL | 6.55 | 6.25 | — | — |
| Particulate matter | ≥ 2 µm NMT 27,000 Particles/Container | 5834 | — | 165[1] | — |
|  | ≥ 10 µm NMT 6000 Particles/Container | 96 | 90 | — | — |
|  | ≥ 25 µm NMT 600 Particles/Container | 2 | 0 | — | — |
| Reconstitution time | NMT 3 minutes | 0.99 | 0.99 | — | — |
| Water (KF) | NMT 3.0% | 0.1% | — | — | — |

[1]Test was performed at 9 months using MilliQ water for reconstitution of the drug product.

TABLE 16

Lot 3 (inverted) Long Term Stability Data

| Test | Acceptance Criteria | Initial | 3 | 6 | 9 |
|---|---|---|---|---|---|
| Appearance | White to off white cake; Colorless solution after reconstitution | Conforms | Conforms | — | — |
| Clarity | Clear, no visible particles after reconstitution | Conforms | Conforms | — | — |
| pH | 7.2-7.4 | 7.4 | 7.4 | — | — |
| Potency (activity) | 600-900 IU/mL | 741 | 745 | — | — |
| Specific activity | ≥ 85 IU/mg protein | 113 | 118 | — | — |
| Purity by GF-HPLC | ≥ 85% active components; ≤ 8% aggregates | 97.05 / 0.55 | 98.90 / 0.63 | — | — |
| Total free PEG by RP-HPLC | ≤ 6.0 mg/mL | 0.45 | 1.18 | — | — |
| Total 10K PEG by RP-HPLC | ≤ 0.6 mg/mL | 0.11 | <0.07 | — | — |
| Protein concentration | 4.5-8.5 mg/mL | 6.55 | 6.29 | — | — |
| Particulate matter | ≥ 2 µm NMT 27,000 Particles/Container | 5834 | — | — | — |
|  | ≥ 10 µm NMT 6000 Particles/Container | 96 | 50 | — | — |
|  | ≥ 25 µm NMT 600 Particles/Container | 2 | 0 | — | — |
| Reconstitution time | NMT 3 minutes | 0.99 | 0.99 | — | — |
| Water (KF) | NMT 3.0% | 0.1% | — | — | — |

Accelerated Stability (25±3° C.; 60%±5% RH)

Figure 11:
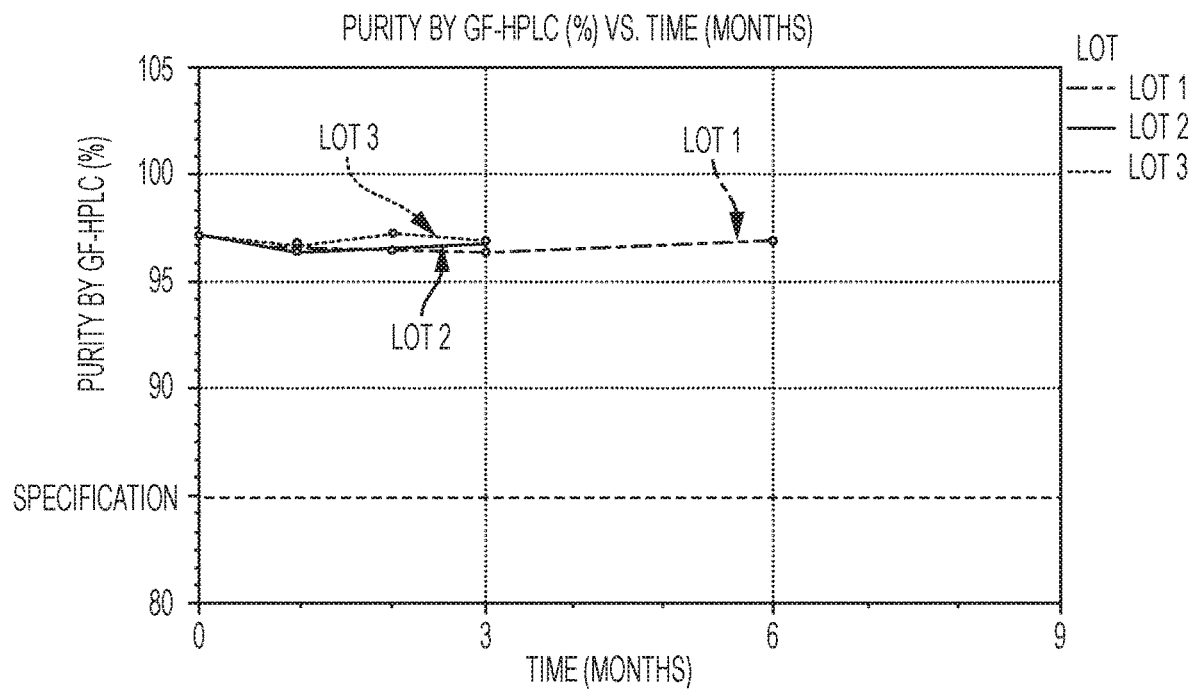
FIG. 11 shows a graph of purity by GF-HPLC (%) vs. time (months) for a lyophilized composition stored under accelerated conditions (25±3° C.; 60%±5% RH), according to embodiments of the present disclosure.
Figure 12:
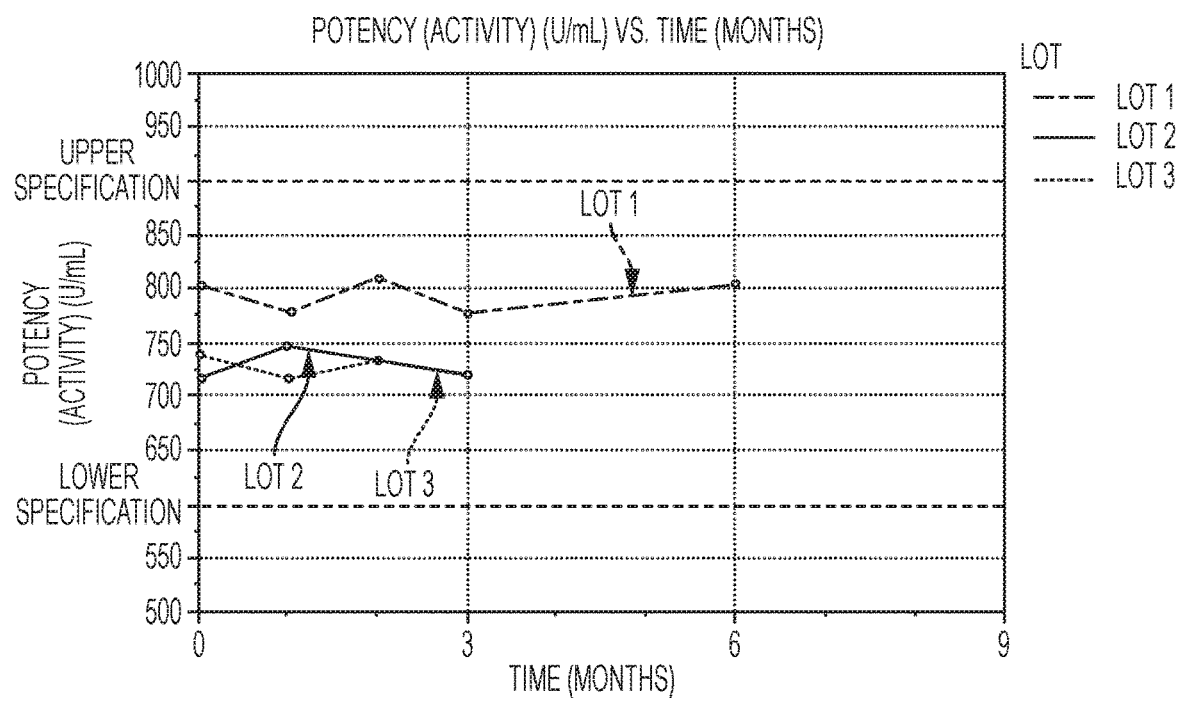
FIG. 12 shows a graph of potency (activity) (IU/mL) vs. time (months) for a lyophilized composition stored under accelerated conditions (25±3° C.; 60%±5% RH), according to embodiments of the present disclosure.
Figure 13:
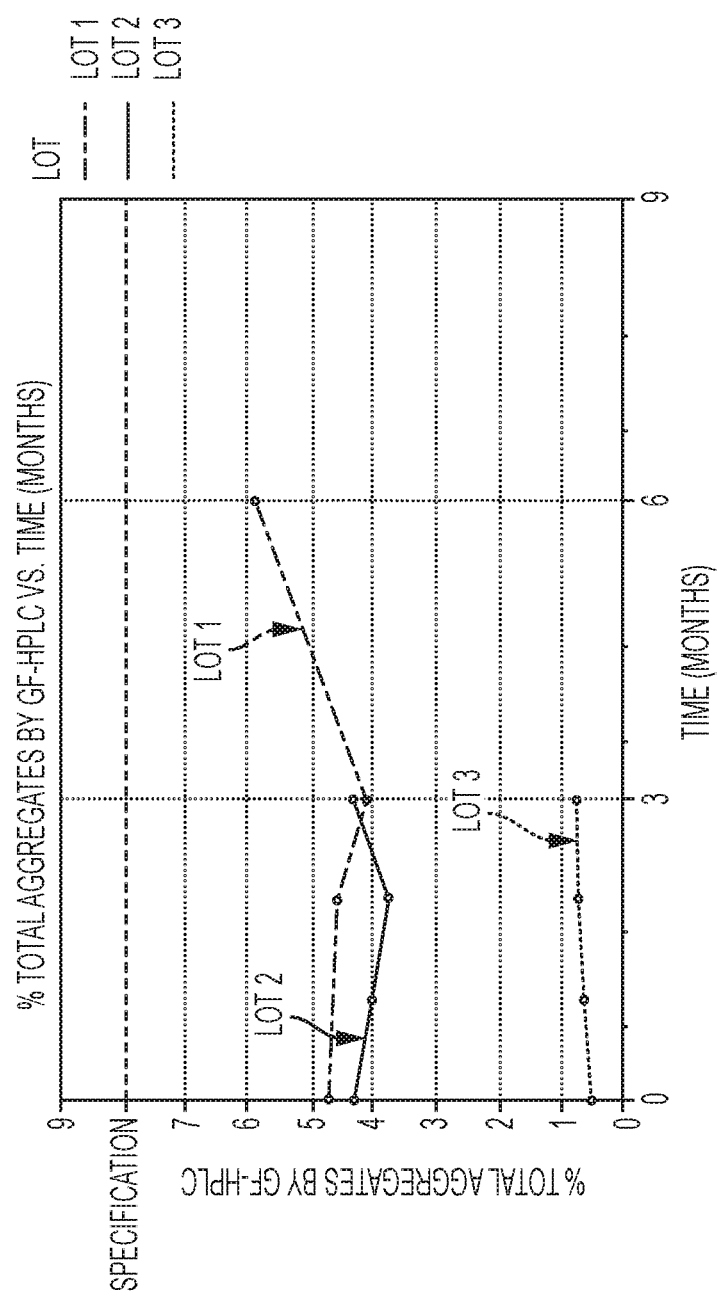
FIG. 13 shows a graph of total aggregates by GF-HPLC vs. time (months) for a lyophilized composition stored under accelerated conditions (25±3° C.; 60%±5% RH), according to embodiments of the present disclosure.

Stability data for lyophilized drug product lots stored under accelerated (25±3° C.; 60%±5% RH) conditions are provided in Tables 17-20. Stability data indicates that lyophilized drug product stored at the accelerated condition remained well within the acceptance criteria for all stability time points. Water Content (KF) ranged from 1.12%-1.23% (specification=NMT 3.0%) at the 25° C. storage condition through 4 weeks. Stability charts for the quality attributes purity (FIG. 11) and potency (FIG. 12), as well as aggregates (FIG. 13), at 25±3° C. are provided in the accompanying figures.

TABLE 17

Lot 1 Accelerated Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | Conforms |
| Clarity | Clear, no visible particles after reconstitution | Conforms | Conforms | Conforms | Conforms | Conforms |
| pH | 7.2-7.4 | 7.4 | 7.4 | 7.4 | 7.4 | 7.4 |
| Potency (activity) | 600-900 IU/mL | 805 | 782 | 809 | 778 | 805 |
| Specific activity | ≥ 85 IU/mg protein | 114 | 111 | 112 | 111 | — |
| Purity by GF-HPLC | ≥ 85% active components; ≤ 8% aggregates | 97.07 / 4.73 | 96.43 / — | 96.58 / 4.6 | 96.29 / 4.11 | 96.88 / 5.9 |
| Total free PEG by RP-HPLC | ≤ 6.0 mg/mL | 0.86 | 0.99 | 1.12 | 0.74 | 0.88 |
| Total 10K PEG by RP-HPLC | ≤ 0.6 mg/mL | 0.13 | 0.14 | 0.17 | 0.12 | 0.13 |
| Protein concentration | 4.5-8.5 mg/mL | 7.06 | 7.03 | 7.2 | 7.02 | 7.13 |
| Particulate matter | ≥ 2 µm NMT 27,000 Particles/Container | 1835 | — | — | 11,753 | 12,096 |

TABLE 17-continued

Lot 1 Accelerated Stability Data

| Test | Acceptance Criteria | Initial | 1 | 2 | 3 | 6 |
|---|---|---|---|---|---|---|
| | 2: 10 μm NMT 6000 Particles/Container | 116 | — | — | 70 | 116 |
| | 2: 25 μm NMT 600 Particles/Container | 1 | — | — | 1 | 1 |
| Reconstitution time | NMT 3 minutes | <1 | <1 | <1 | <1 | <1 |
| Water (KF) | NMT3.0% | — | — | — | — | — |

TABLE 18

Lot 2 Accelerated Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | — |
| Clarity | Clear, no visible particles after reconstitution | Conforms | Conforms | Conforms | Conforms | — |
| pH | 7.2-7.4 | 7.4 | 7.4 | 7.4 | 7.4 | — |
| Potency (activity) | 600-900 IU/mL | 718 | 748 | 733 | 720 | — |
| Specific activity | 2: 85 IU/mg protein | 111 | 115 | 113 | 116 | — |
| Purity by GF-HPLC | 2: 85% active components; :S 8% aggregates | 97.16 4.35 | 96.69 4.01 | 96.52 3.76 | 96.79 4.31 | — |
| Total free PEG by RP-HPLC | :S 6.0 mg/mL | 1.31 | 1.48 | 1.12 | 1.16 | — |
| Total 10K PEG by RP-HPLC | :S 0.6 mg/mL | 0.15 | 0.18 | 0.16 | 0.14 | — |
| Protein concentration | 4.5-8.5 mg/mL | 6.48 | 6.51 | 6.46 | 6.21 | — |
| Particulate matter | 2 μmNMT 27,000 Particles/Container | 530 | — | — | 10,051 | — |
| | 10 μm NMT 6000 Particles/Container | 12 | — | — | 121 | — |
| | 25 μm NMT 600 Particles/Container | 1 | — | — | 6 | — |
| Reconstitution time | NMT 3 minutes | <1 | <1 | <1 | <1 | — |
| Water (KF) | NMT3.0% | 0.2% | — | — | — | — |

TABLE 19

Lot 3 (upright) Accelerated Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | — |
| Clarity | Clear, no visible particles after reconstitution | Conforms | Conforms | Conforms | Conforms | — |
| pH | 7.2-7.4 | 7.4 | 7.4 | 7.4 | 7.4 | — |
| Potency (activity) | 600-900 IU/mL | 741 | 700 | 750 | 718 | — |
| Specific activity | 85 IU/mg protein | 113 | 111 | 113 | — | — |
| Purity by GF-HPLC | 85% active components; :S 8% aggregates | 97.05 0.55 | 96.88 0.62 | 97.25 0.75 | 96.98 0.89 | — |

TABLE 19-continued

Lot 3 (upright) Accelerated Stability Data

| Test | Acceptance Criteria | Initial | 1 | 2 | 3 | 6 |
|---|---|---|---|---|---|---|
| Total free PEG by RP-HPLC | ≤ 6.0 mg/mL | 0.45 | 0.95 | 1.06 | 0.87 | — |
| Total 10K PEG by RP-HPLC | ≤ 0.6 mg/mL | 0.11 | <0.07 | <0.07 | <0.07 | — |
| Protein concentration | 4.5-8.5 mg/mL | 6.55 | 6.28 | 6.63 | 6.34 | — |
| Particulate matter | ≥ 2 μm NMT 27,000 Particles/Container | 5834 | — | — | 8000 | — |
| | ≥ 10 μm NMT 6000 Particles/Container | 96 | — | — | 83 | — |
| | ≥ 25 μm NMT 600 Particles/Container | 2 | — | — | 2 | — |
| Reconstitution time | NMT 3 minutes | <1 | <1 | <1 | <1 | — |
| Water (KF) | NMT 3.0% | 0.1% | — | — | — | — |

TABLE 20

Lot 3 (inverted) Accelerated Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | — |
| Clarity | Clear, no visible particles after reconstitution | Conforms | Conforms | Conforms | Conforms | — |
| pH | 7.2-7.4 | 7.4 | 7.4 | 7.4 | 7.4 | — |
| Potency (activity) | 600-900 IU/mL | 741 | 719 | 733 | 721 | — |
| Specific activity | ≥ 85 IU/mg protein | 113 | 113 | 113 | 113 | — |
| Purity by GF-HPLC | ≥ 85% active components; ≤ 8% aggregates | 97.05 / 0.55 | 96.76 / 0.63 | 97.31 / 0.72 | 97.02 / 0.74 | — |
| Total free PEG by RP-HPLC | ≤ 6.0 mg/mL | 0.45 | 0.92 | 1.04 | 1.22 | — |
| Total 10K PEG by RP-HPLC | ≤ 0.6 mg/mL | 0.11 | <0.07 | <0.07 | 0.14 | — |
| Protein concentration | 4.5-8.5 mg/mL | 6.55 | 6.37 | 6.49 | 6.38 | — |
| Particulate matter | ≥ 2 μm NMT 27,000 Particles/Container | 5834 | — | — | 10,277 | — |
| | ≥ 10 μm NMT 6000 Particles/Container | 96 | — | — | 113 | — |
| | ≥ 25 μm NMT 600 Particles/Container | 2 | — | — | 1 | — |
| Reconstitution time | NMT 3 minutes | <1 | <1 | <1 | <1 | — |
| Water (KF) | NMT 3.0% | 0.1% | — | — | — | — |

Heat Stress Stability (40±2° C.; 75%±5% RH)

Figure 14:
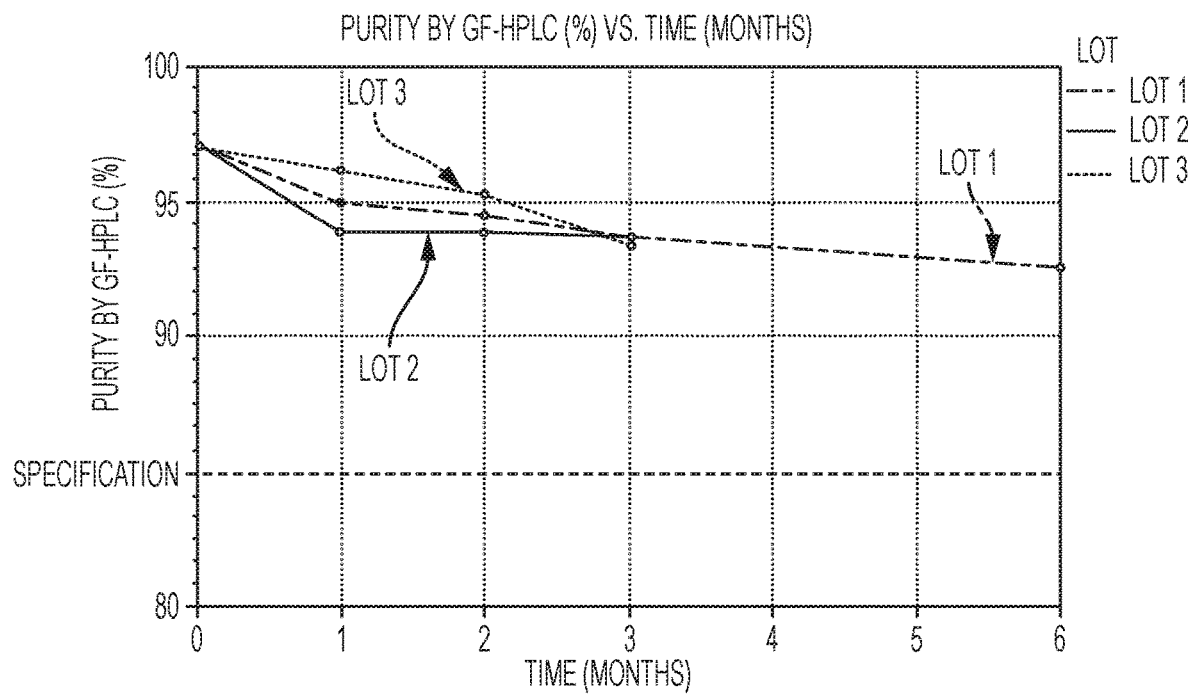
FIG. 14 shows a graph of purity by GF-HPLC (%) vs. time (months) for a lyophilized composition stored under heat stress conditions (40±2° C.; 75%±5% RH), according to embodiments of the present disclosure.
Figure 15:
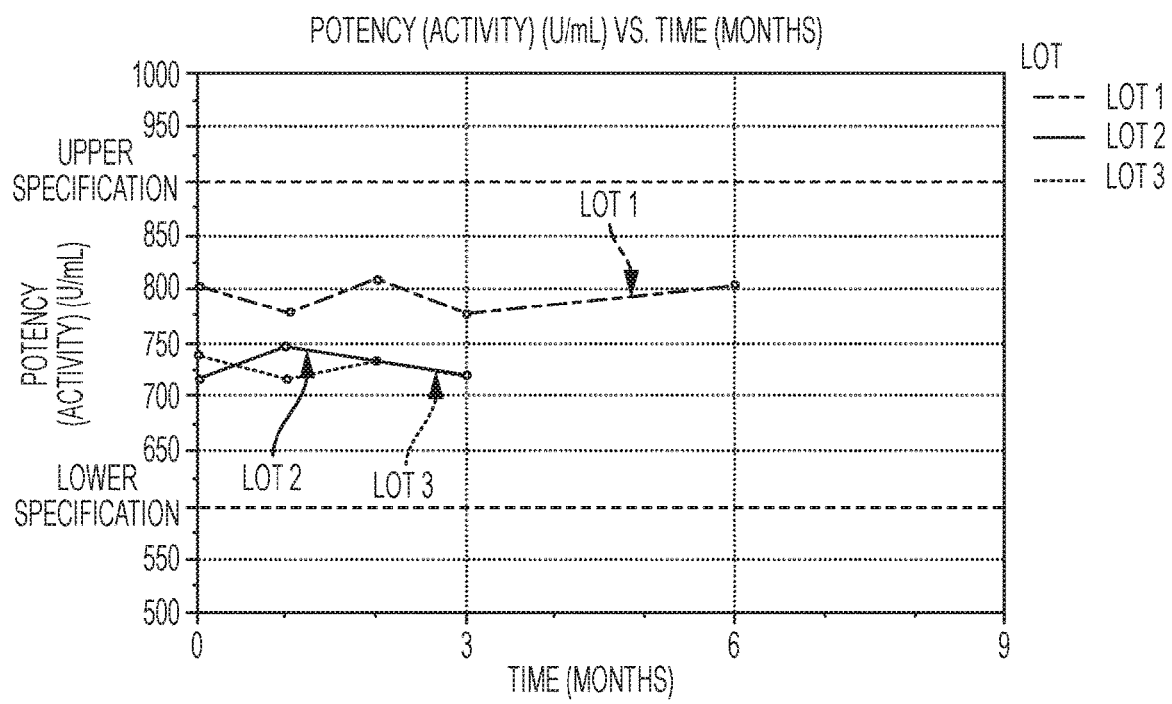
FIG. 15 shows a graph of potency (activity) (IU/mL) vs. time (months) for a lyophilized composition stored under heat stress conditions (40±2° C.; 75%±5% RH), according to embodiments of the present disclosure.
Figure 16:
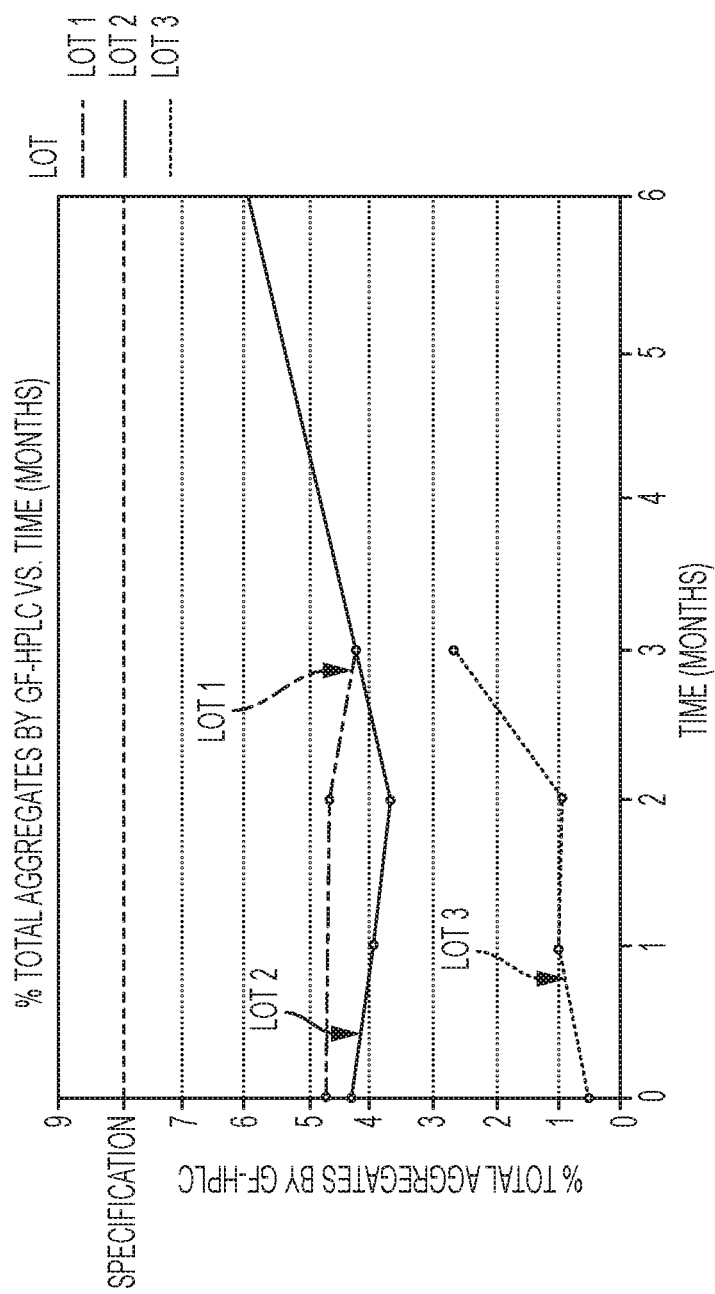
FIG. 16 shows a graph of total aggregates by GF-HPLC vs. time (months) for a lyophilized composition stored under heat stress conditions (40±2° C.; 75%±5% RH), according to embodiments of the present disclosure.

Stability data for lyophilized drug product lots stored under stress (40±2° C.; 75%±5% RH) conditions are provided in Tables 21-24. Stability data indicated that lyophilized drug product stored at stress conditions remained well within the acceptance criteria for the duration of the study. Water Content (KF) ranged from 1.16%-1.45% (specification=NMT 3.0%) at the 40° C. storage condition through 4 weeks. Stability charts for the potency (FIG. 14) and purity (FIG. 15), as well as aggregates (FIG. 16), at 40±2° C. are provided in the accompanying figures.

TABLE 21

Lot 1 Heat Stress Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | Conforms |
| Clarity | Clear, no visible particles after reconstitution | Conforms | Conforms | Conforms | Conforms | Conforms |
| pH | 7.2-7.4 | 7.4 | 7.4 | 7.4 | 7.4 | 7.4 |
| Potency (activity) | 600-900 IU/mL | 805 | 757 | 747 | 759 | 746 |
| Specific activity | ≥ 85 IU/mg protein | 114 | 109 | 107 | 107 | — |
| Purity by GF-HPLC | ≥ 85% active components; ≤ 8% aggregates | 97.07<br>4.73 | 95.02<br>— | 94.52<br>4.74 | 93.64<br>4.31 | 92.64<br>6.01 |
| Total free PEG by RP-HPLC | ≤ 6.0 mg/mL | 0.86 | 1.07 | 1.15 | 0.86 | 1.07 |
| Total 10K PEG by RP-HPLC | ≤ 0.6 mg/mL | 0.13 | 0.15 | 0.16 | 0.13 | 0.14 |
| Protein concentration | 4.5-8.5 mg/mL | 7.06 | 6.94 | 7.01 | 7.09 | 7.08 |
| Particulate matter | ≥ 2 µm NMT 27,000 Particles/Container | 1835 | — | — | — | 12,025 |
| | ≥ 10 µm NMT 6000 Particles/Container | 116 | — | — | — | 53 |
| | ≥ 25 µm NMT 600 Particles/Container | 1 | — | — | — | 1 |
| Reconstitution time | NMT 3 minutes | <1 | <1 | <1 | <1 | — |
| Water (KF) | NMT 3.0% | — | — | — | — | — |

TABLE 22

Lot 2 Heat Stress Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | — |
| Clarity | Clear, no visible particles after reconstitution | Conforms | Conforms | Conforms | Conforms | — |
| pH | 7.2-7.4 | 7.4 | 7.4 | 7.4 | 7.4 | — |
| Potency (activity) | 600-900 IU/mL | 718 | 738 | 690 | 694 | — |
| Specific activity | ≥ 85 IU/mg protein | 114 | 109 | 107 | 107 | — |
| Purity by GF-HPLC | ≥ 85% active components; ≤ 8% aggregates | 97.16<br>4.35 | 93.91<br>3.99 | 93.92<br>3.71 | 93.70<br>4.33 | —<br>— |
| Total free PEG by RP-HPLC | ≤ 6.0 mg/mL | 1.31 | 1.45 | 1.15 | 1.26 | — |
| Total 10K PEG by RP-HPLC | ≤ 0.6 mg/mL | 0.15 | 0.17 | 0.16 | 0.14 | — |
| Protein concentration | 4.5-8.5 mg/mL | 6.48 | 6.42 | 6.4 | 6.3 | — |
| Particulate matter | ≥ 2 µm NMT 27,000 Particles/Container | 530 | — | — | — | — |
| | ≥ 10 µm NMT 6000 Particles/Container | 12 | — | — | — | — |
| | ≥ 25 µm NMT 600 Particles/Container | 1 | — | — | — | — |
| Reconstitution time | NMT 3 minutes | <1 | <1 | <1 | <1 | — |
| Water (KF) | NMT 3.0% | 0.2% | — | — | — | — |

TABLE 23

Lot 3 (upright) Heat Stress Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | — |
| Clarity | Clear, no visible particles after reconstitution | Conforms | Conforms | Conforms | Conforms | — |
| pH | 7.2-7.4 | 7.4 | 7.4 | 7.4 | 7.4 | — |
| Potency (activity) | 600-900 IU/mL | 741 | 722 | 691 | 681 | — |
| Specific activity | ≥ 85 IU/mg protein | 113 | 112 | 111 | 109 | — |
| Purity by GF-HPLC | ≥ 85% active components; ≤ 8% aggregates | 97.05 / 0.55 | 96.11 / 0.98 | 95.4 / 2.58 | 93.1 / 2.88 | — |
| Total free PEG by RP-HPLC | ≤ 6.0 mg/mL | 0.45 | 1.1 | 1.25 | 0.64 | — |
| Total 10K PEG by RP-HPLC | ≤ 0.6 mg/mL | 0.11 | <0.07 | <0.07 | <0.07 | — |
| Protein concentration | 4.5-8.5 mg/mL | 6.55 | 6.43 | 6.23 | 6.25 | — |
| Particulate matter | ≥ 2 μm NMT 27,000 Particles/Container | 5834 | — | — | 8989 | — |
|  | ≥ 10 μm NMT 6000 Particles/Container | 96 | — | — | 116 | — |
|  | ≥ 25 μm NMT 600 Particles/Container | 2 | — | — | 2 | — |
| Reconstitution time | NMT 3 minutes | <1 | <1 | <1 | <1 | — |
| Water (KF) | NMT 3.0% | 0.1% | — | — | — | — |

TABLE 24

Lot 3 (inverted) Heat Stress Stability Data

| Test | Acceptance Criteria | Initial | 1 | 2 | 3 | 6 |
|---|---|---|---|---|---|---|
| Appearance | White to off white cake; Colorless solution after reconstitution | Conforms | Conforms | Conforms | Conforms | — |
| Clarity | Clear, no visible particles after reconstitution | Conforms | Conforms | Conforms | Conforms | — |
| pH | 7.2-7.4 | 7.4 | 7.4 | 7.4 | 7.4 | — |
| Potency (activity) | 600-900 IU/mL | 741 | 719 | 668 | 663 | — |
| Specific activity | ≥ 85 IU/mg protein | 113 | 113 | 107 | 106 | — |
| Purity by GF-HPLC | ≥ 85% active components; ≤ 8% aggregates | 97.05 / 0.55 | 96.12 / 1.02 | 95.31 / 1.01 | 96.45 / 2.74 | — |
| Total free PEG by RP-HPLC | ≤ 6.0 mg/mL | 0.45 | 1.08 | 1.25 | 0.62 | — |
| Total 10K PEG by RP-HPLC | ≤ 0.6 mg/mL | 0.11 | <0.07 | <0.07 | <0.07 | — |
| Protein concentration | 4.5-8.5 mg/mL | 6.55 | 6.38 | 6.23 | 6.25 | — |
| Particulate matter | 2 μm NMT 27,000 Particles/Container | 5834 | — | — | 9963 | — |
|  | 10 μm NMT 6000 Particles/Container | 96 | — | — | 157 | — |
|  | 25 μm NMT 600 Particles/Container | 2 | — | — | 3 | — |
| Reconstitution time | NMT 3 minutes | <1 | <1 | <1 | <1 | — |
| Water (KF) | NMT 3.0% | 0.1% | — | — | — | — |

Example 2

A composition that included a polyethylene glycol-asparaginase having an SC-PEG linker (i.e., succinimidyl carbonate linker) was produced—calaspargase pegol (succinimidyl carbonate-polyethylene glycol [SC-PEG] E. coli L-asparaginase). The composition of the composition is provided in Table 25.

TABLE 25

Components of the Calaspargase Pegol Composition

| Component | Grade | Amount per g* |
|---|---|---|
| Calaspargase Pegol | n/a | 750 IU |
| Dibasic sodium phosphate | USP | 5.58 mg |
| Monobasic sodium phosphate | USP | 1.29 mg |
| Sodium Chloride | USP | 8.50 mg |
| Water for injection (WFI) | USP | QS to 1.0 g |

Example 3

Following production of the concentrated bulk composition, a lyophilized composition of calaspargase pegol can be produced from the concentrated bulk composition. FIG. 1 shows an example of a process flow diagram that can be used for making a lyophilized storage stable composition according to embodiments of the present disclosure. The lyophilized composition powder for injection can be produced in a single-use vial containing 3,750 IU of active calaspargase pegol (750 IU/mL after reconstitution with 5.2 mL of WFI). The components of the lyophilized composition can include 4.5% sucrose, dibasic sodium phosphate, monobasic sodium phosphate, and sodium chloride after reconstitution. The composition of the lyophilized composition is provided in Table 26.

TABLE 26

Components of the Calaspargase Pegol Composition

| Component | Grade | Amount per g* |
|---|---|---|
| Calaspargase Pegol | n/a | 750 IU |
| Dibasic sodium phosphate | USP | 2.79 mg |
| Monobasic sodium phosphate | USP | 0.60 mg |
| Sodium Chloride | USP | 4.25 mg |
| Sucrose | National Formulary (NF) | 45 mg |
| Water for injection (WFI) | USP | QS to 1.0 g |

*values are post reconstituted with WFI

Example 4

The purpose of this study was to provide comparative pharmacokinetic (PK), pharmacodynamics (PD) and immunogenicity information for liquid pegaspargase (PEG-L-asparaginase; Oncaspar®) and lyophilized pegaspargase, when administered intravenously, via slow bolus injection, to beagle dogs once (Day 1) or once weekly for 4 weeks (Days 1, 15, 22, 29 and 36). Because the reconstituted lyophilized pegaspargase will be administered intravenously to humans, the same route of administration was used in this study. A single-dose and repeat-dose PK/PD study was necessary to determine and compare the pharmacokinetics and pharmacodynamics of liquid and reconstituted lyophilized versions at an equivalent dose.

Beagle dogs (nominally 5/sex/group) were administered 500 IU/kg liquid pegaspargase or reconstituted lyophilized pegaspargase by intravenous injection at a dose volume of 0.667 mL/kg (see Table 27). The beagles were approximately 6 months old with males 7.2 kg to 10.7 kg and females 5.6 kg to 8.2 kg.

Liquid pegaspargase (5 mL PBS buffer with 50 mM phosphate and 0.85% saline at pH 7.2-7.4) was used as supplied and no preparation was needed. Lyophilized pegaspargase (see example 1) was prepared for administration by (using a 21 gauge syringe) reconstituting the contents of a vial with 5.2 mL water for injection (WFI) using aseptic techniques to achieve a 750 IU/mL concentration. The contents of the vial were gently swirled until completely dissolved. The mixture was visually inspected for particulate matter, cloudiness or discolorations prior to administration. Fresh formulations were prepared for each day of dose administration, maintained at room temperature and used within 2 hours of preparation.

TABLE 27

Protocol and Dosing Regimen

| Group | Treatment | Dose (IU/kg) | Concentration (IU/mL) | Volume dose (mL/kg) | Male Dogs | Female Dogs |
|---|---|---|---|---|---|---|
| 1 | Liquid pegaspargase - Single-Dose | 500 | 750 | 0.667 | 5 | 6 |
| 2 | Liquid pegaspargase - Repeat-Dose | 500 | 750 | 0.667 | 5 | 5 |
| 3 | Lyophilized pegaspargase - Single-Dose | 500 | 750 | 0.667 | 5 | 5 |
| 4 | Lyophilized pegaspargase - Repeat-Dose | 500 | 750 | 0.667 | 6 | 5 |

Animals in Groups 1 and 3 received a single dose of liquid pegaspargase or lyophilized pegaspargase, respectively on Day 1. Animals in Groups 2 and 4 were given repeated doses of liquid pegaspargase or lyophilized pegaspargase, respectively. Slow bolus (over approximately 2 minutes) intravenous injection within 2 hours of test article preparation were administered. An indwelling catheter (non-butterfly catheter) was used, followed by a saline flush to clear the catheter cap of any remaining dose volume. A straight needle was inserted into the catheter cap to guarantee the needle placement would remain consistent over the 2 minute duration.

Blood samples were obtained from all animals on Days 1 and 36 for pharmacokinetic and pharmacodynamics analysis. Approximately 1.0 mL of whole blood was obtained at each time point. Animals were unanesthetized and non-fasted prior to blood collection. Blood was collected into tubes containing sodium heparin anticoagulant and placed on wet ice in an upright position. Centrifugation for 5 minutes (at approximately 3000 rpm, at approximately 4° C.) of the blood sample to obtain plasma began within 5 minutes of collection of the blood sample.

PD: One aliquot of 125 μL of plasma was pipetted into a cryotube pre-filled with 125 μL of SeraPrep for asparagine determination. The tube was inverted 3 times to mix the SeraPrep and flash frozen immediately with liquid nitrogen or methanol/dry ice within 15 minutes from collection of the blood sample. All aliquots containing SeraPrep were analyzed for asparagine determination by High Performance Liquid Chromatography (HPLC) with mass spectrometric detection (LC-MS/MS).

PK: The remainder of the plasma was split into two cryotubes for asparaginase activity determination and flash frozen within 30 minutes from collection of the blood sample. All aliquots not containing SeraPrep were analyzed for asparaginase activity by a colorimetric mixed enzyme reaction.

Results

Analyses conducted during the treatment period for the lyophilized pegaspargase confirmed that dose formulations of appropriate concentration (expected protein concentration of 6.6 mg/mL and activity of 741 IU/mL, per Batch Analysis) were administered (Table 28).

TABLE 28

Analytical Chemistry

| Interval | Protein (miU/mL) | | Activity (IU/mL) | |
| --- | --- | --- | --- | --- |
|  | Male | Female | Male | Female |
| Injection Day 1 | 6.36 | 6.30 | 738 | 722 |
| Injection Day 22 | 6.55 | 6.54 | 794 | 785 |
| Injection Day 36 | 6.30 | 6.44 | 722 | 741 |

Pooled group mean plasma concentrations (Cmax) of asparaginase and the pooled group mean areas under the plasma asparaginase concentration time curves estimated up to 552 hours postdose (AUC$_{0.552}$) on Day 1 and following repeated dosing on Day 36 are summarized for each group (combined sexes) in Table 29.

TABLE 29

Bioequivalence: Pooled group mean data (combined sexes)

| Formulation | Group mean Cmax (mIU/mL) | | Group mean AUC$_{0.552}$ (mIU · h/mL) | |
| --- | --- | --- | --- | --- |
| (500 IU/kg) | Day 1 | Day 36 | Day 1 | Day 36 |
| Liquid  Geomean | 9947 | 19440 | 2929202 | 4514287 |
| Mean | 10018 | 19580 | 2953000 | 4561000 |

TABLE 29-continued

Bioequivalence: Pooled group mean data (combined sexes)

| Formulation | Group mean Cmax (mIU/mL) | | Group mean AUC$_{0.552}$ (mIU · h/mL) | |
| --- | --- | --- | --- | --- |
| (500 IU/kg) | Day 1 | Day 36 | Day 1 | Day 36 |
| Lyophilized  SD | 1300 | 2404 | 405245 | 648322 |
| CV¾ | 13.0 | 12.3 | 13.7 | 14.2 |
| Geomean | 9393 | 17416 | 2603255 | 4258048 |
| Mean | 9416 | 17480 | 2611000 | 4350000 |
| SD | 688 | 1555 | 214758 | 797663 |
| CV¾ | 7.3 | 8.9 | 8.2 | 18.3 |

The study was designed as a parallel group design and the data were analyzed statistically using analysis of variance techniques. Cmax and AUC$_{0.552}$ data from both days were analyzed using an ANOVA model with formulation, time, sex and their interactions as factors.

The two pegaspargase formulations were analyzed with respect to Cmax and AUC0.ss2 and the corresponding two-sided 90% CIs for the ratio of geometric means are summarized in Table 30.

TABLE 30

Pharmacokinetic Data

| Parameter | Table of Formulation means (back-transformed-mIU/mL) | | 90% Confidence interval of mean ratio (Lyophilized/Liquid) | | |
| --- | --- | --- | --- | --- | --- |
|  | Lyophilized | Liquid | Lower | Ratio | Upper |
| Cmax | 12790 | 13943 | 0.867 | 0.917 | 0.970 |
| AUC0-ss2 | 3329382 | 3636380 | 0.841 | 0.916 | 0.996 |

For Cmax there was evidence of bioequivalence as the confidence interval (0.867 to 0.970) was contained in the critical region. For AUC$_{0.552}$ there was evidence of bioequivalence as the confidence interval (0.841 to 0.996) was contained in the critical region.

Mean maximum plasma concentrations (Cmax) of pegaspargase and the mean areas under the plasma pegaspargase concentration time curves estimated up to 552 hours postdose (AUC$_{0.552}$) on Day 1 and following repeated dosing on Day 36 are summarized below (by sex) with standard deviations in parentheses in Table 31.

TABLE 31

Plasma Concentration-Time Profiles

| Formulation | Cmax (mIU/mL) | | | | AUC0-ss2 (mIU · h/mL) | | | |
| --- | --- | --- | --- | --- | --- | --- | --- | --- |
|  | Day 1 | | Day 36 | | Day 1 | | Day 36 | |
| (500 IU/kg) | Males | Females | Males | Females | Males | Females | Males | Females |
| Liquid | 10700 | 9450 | 20200 | 19000 | 3250000 | 2660000 | 4660000 | 4470000 |
|  | (1600) | (610) | (2700) | (2200) | (370000) | (140000) | (690000) | (670000) |
| Lyophilized | 9580 | 9250 | 17800 | 17200 | 2700000 | 2520000 | 4170000 | 4530000 |
|  | (540) | (840) | (1400) | (1800) | (190000) | (220000) | (1120000) | (320000) |

The relationships between mean maximum plasma concentrations (Cmax) of asparaginase, mean areas under the plasma asparaginase concentration time curves (AUC0.ss2) and dose level for the lyophilized formulation are expressed as a ratio compared to the liquid formulation and presented in Table 32.

TABLE 32

Relationship between Mean Cmax, Mean AUC, and Dose Level

| Formulation (500 IU/kg) | Dose level ratio | Cmax ratio Day 1 Males | Cmax ratio Day 1 Females | Cmax ratio Day36 Males | Cmax ratio Day36 Females | $AUC_{0\_552}$ ratio Day 1 Males | $AUC_{0\_552}$ ratio Day 1 Females | $AUC_{0\_552}$ ratio Day36 Males | $AUC_{0\_552}$ ratio Day36 Females |
|---|---|---|---|---|---|---|---|---|---|
| Liquid | 1 | 1 | 1 | 1 | 1 | 1 | 1 | 1 | 1 |
| Lyophilized | 1 | 0.90 | 0.98 | 0.88 | 0.91 | 0.83 | 0.95 | 0.89 | 1.0 |

The Cmax and AUC0.ss2 values of systemic exposure of dogs to asparaginase were similar following administration of reconstituted lyophilized pegaspargase, compared to the liquid formulation, on Day 1 and following repeated administrations on Day 36. There was no evidence of a significant difference between the formulations for $AUC_{0.552}$, but there was some evidence of a difference between the Cmax values of the different formulations where Cmax following administration of the lyophilized product was slightly lower (8%) than when dosed as the liquid formulation.

The Cmax and $AUC_{0.552}$ values of systemic exposure of female dogs to asparaginase were generally similar to those indices of exposure in males and there was no evidence for any statistically significant sex related differences in systemic exposure for Cmax or $AUC_{0.552}$.

Other parameters evaluated during the study were: viability, clinical observations, body weight, food consumption, breathing rates, body temperature, hematology, coagulation and blood chemistry; no test article-related adverse effects were seen for these.

After repeated intravenous doses (Day 36) the Cmax values and extent (AUC0.ss2) of systemic exposure of dogs to asparaginase were higher than those values after a single dose (Day 1) and these differences were statistically significant (p<0.001). The mean accumulation ratios, calculated based on AUC0.ss2 values (note that different animals provided the data on each day), were greater than one indicating that accumulation of asparaginase occurred after repeated intravenous administration of liquid pegaspargase.

Overall, the two pegaspargase formulations were shown to be equivalent with respect to Cmax and AUC0.ss2, as the corresponding two-sided 90% CIs for the ratio of geometric means fell completely within the conventional margins of bioequivalence ranging from 0.8 to 1.25. There was no significant difference between the two formulations for $AUC_{0.552}$. Systemic exposure to asparaginase was similar with the two products and some accumulation occurred in both sexes with repeated dosing. Asparagine was completely suppressed for up to 336 hours in all animals and up to 552 hours in the majority of them.

In summary, there were no notable differences between doses of 500 IU/kg with either the liquid pegaspargase or reconstituted lyophilized pegaspargase and they had comparable pharmacokinetic, pharmacodynamics and immunogenic profiles.

EMBODIMENTS

In one embodiment, the present disclosure provides a lyophilized storage stable composition that includes a polyalkylene oxide-asparaginase having a polyalkylene oxide group covalently linked by a linker to an asparaginase. The lyophilized storage stable composition also includes a buffer, a salt, and a sugar.

In some embodiments, the polyalkylene oxide group includes a polyethylene glycol group. In some embodiments, the polyethylene glycol group has a molecular weight ranging from 2,000 to 10,000 daltons. In some embodiments, the polyethylene glycol group has a molecular weight of 5,000 daltons.

In some embodiments, the asparaginase is E. coli asparaginase.

In some embodiments, the linker is a urethane linker. In some embodiments, the linker is a succinate linker.

In some embodiments, the polyalkylene oxide-asparaginase is present in an amount ranging from 500 to 1,000 IU/g.

In some embodiments, the buffer includes a phosphate buffer. In some embodiments, the phosphate buffer includes dibasic sodium phosphate and monobasic sodium phosphate. In some embodiments, the dibasic sodium phosphate is present in an amount ranging from 0.1 to 0.5 wt. %. In some embodiments, the monobasic sodium phosphate is present in an amount ranging from 0.01 to 0.1 wt. %.

In some embodiments, the salt is sodium chloride. In some embodiments, the sodium chloride is present in an amount ranging from 0.1 to 1 wt. %.

In some embodiments, the sugar includes a disaccharide. In some embodiments, the disaccharide includes sucrose. In some embodiments, the sugar includes sucrose in an amount ranging from 1 to 10 wt. %.

In some embodiments, the composition is present in a unit dosage container. In some embodiments, the unit dosage container is a vial. In some embodiments, the vial is a sealed glass vial.

In some embodiments, the polyalkylene oxide-asparaginase is present in an amount of 750 IU/g, the polyalkylene oxide group includes a polyethylene glycol group with a molecular weight of 5,000 daltons, the asparaginase is E. coli asparaginase, the linker is a urethane linker, the buffer is a phosphate buffer including dibasic sodium phosphate in an amount ranging from 0.25 to 0.3 wt. % and monobasic sodium phosphate in an amount ranging from 0.05 to 0.07 wt. %, the salt is sodium chloride in an amount ranging from 0.4 to 0.45 wt. %, and the sugar is sucrose in an amount ranging from 4 to 5 wt. %.

In some embodiments, the polyalkylene oxide-asparaginase is present in an amount of 750 IU/g, the polyalkylene oxide group includes a polyethylene glycol group with a molecular weight of 5,000 daltons, the asparaginase is E. coli asparaginase, the linker is a urethane linker, the buffer is a phosphate buffer including dibasic sodium phosphate in an amount of 0.279 wt. % and monobasic sodium phosphate in an amount of 0.06 wt. %, the salt is sodium chloride in an amount of 0.425 wt. %, and the sugar is sucrose in an amount of 4.5 wt. %.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a succinate linker, the buffer is a phosphate buffer including dibasic sodium phosphate in an amount ranging from 0.25 to 0.3 wt. % and monobasic sodium phosphate in an amount ranging from 0.05 to 0.07 wt. %, the salt is sodium chloride in an amount ranging from 0.4 to 0.45 wt. %, and the sugar is sucrose in an amount ranging from 4 to 5 wt. %.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a succinate linker, the buffer is a phosphate buffer including dibasic sodium phosphate in an amount of 0.279 wt. % and monobasic sodium phosphate in an amount of 0.06 wt. %, the salt is sodium chloride in an amount of 0.425 wt. %, and the sugar is sucrose in an amount of 4.5 wt. %.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a urethane linker, the buffer is a phosphate buffer including dibasic sodium phosphate in an amount of 0.558 wt. % and monobasic sodium phosphate in an amount of 0.129 wt. %, and the salt is sodium chloride in an amount of 0.85 wt. %

In another embodiment, the present disclosure provides a lyophilized storage stable composition that includes a polyethylene glycol-asparaginase having a polyethylene glycol group covalently linked by a succinate linker to an *E. coli* asparaginase. In another embodiment, the present disclosure provides a lyophilized storage stable composition that includes a polyethylene glycol-asparaginase having a polyethylene glycol group covalently linked by a urethane linker to an *E. coli* asparaginase. The lyophilized storage stable composition also includes a phosphate buffer, a salt, and optionally a disaccharide as outlined in the embodiments above.

In another embodiment, the present disclosure provides a method of deaminating asparagine in a subject by administering a composition as disclosed herein.

In some embodiments, the method includes reconstituting a lyophilized storage stable composition according to the present disclosure to produce a reconstituted dosage unit, and administering the reconstituted dosage unit to the subject to deaminate asparagine in the subject. In some embodiments, the reconstituting includes combining the lyophilized storage stable composition with water for injection (WFI).

In some embodiments, the dosage unit includes 700 to 800 IU/mL of polyalkylene oxide-asparagmase. In some embodiments, the dosage unit includes 2.5 to 6 mg/g dibasic sodium phosphate. In some embodiments, the dosage unit includes 2.5 to 3 mg/g dibasic sodium phosphate. In some embodiments, the dosage unit includes 5 to 6 mg/g dibasic sodium phosphate. In some embodiments, the dosage unit includes 5.25 to 5.75 mg/g dibasic sodium phosphate.

In some embodiments, the dosage unit includes 0.45 to 1.5 mg/g monobasic sodium phosphate. In some embodiments, the dosage unit includes 0.45 to 0.75 mg/g monobasic sodium phosphate. In some embodiments, the dosage unit includes 1 to 2 mg/g monobasic sodium phosphate. In some embodiments, the dosage unit includes 1 to 1.5 mg/g monobasic sodium phosphate.

In some embodiments, the dosage unit includes 4 to 9 mg/g sodium chloride. In some embodiments, the dosage unit includes 4 to 4.5 mg/g sodium chloride. In some embodiments, the dosage unit includes 8 to 9 mg/g sodium chloride.

In some embodiments, the dosage unit includes sucrose. In some embodiments, the sucrose is present in an amount ranging from 40 to 50 mg/g.

In some embodiments, the reconstituted dosage unit delivers from 1,500 to 3,000 IU/m$^2$ of polyalkylene oxide-asparaginase to the subject. In some embodiments, the reconstituted dosage unit delivers from 2,000 to 2,750 IU/m$^2$ of polyalkylene oxide-asparaginase to the subject.

In some embodiments, the method is a method of treating the subject for a neoplastic condition. In some embodiments, the neoplastic condition is a cancer. In some embodiments, the cancer is a leukemia. In some embodiments, the leukemia is acute lymphoblastic leukemia (ALL). In some embodiments, the leukemia is acute myeloid leukemia (AML).

In some embodiments, the subject has been prescribed a treatment regimen that includes an induction phase, a consolidation phase and a maintenance phase. In some embodiments, the method includes administering a single reconstituted dosage unit to the subject in the induction phase and multiple reconstituted dosage units during the maintenance phase. In some embodiments, the multiple reconstituted dosage units are administered to the subject by administering a reconstituted dosage unit to the subject every 3 weeks. In some embodiments, the multiple reconstituted dosage units are administered to the subject by administering a reconstituted dosage unit to the subject every 2 weeks.

In some embodiments, the subject is a juvenile. In some embodiments, the subject is an adult.

In some embodiments, the polyalkylene oxide-asparaginase is present in an amount of 750 IU/mL, the polyalkylene oxide group includes a polyethylene glycol group with a molecular weight of 5,000 daltons, the asparaginase is *E. coli* asparaginase, the linker is a urethane linker, the buffer is a phosphate buffer including dibasic sodium phosphate in an amount ranging from 2.5 to 3 mg/g and monobasic sodium phosphate in an amount ranging from 0.5 to 0.7 mg/g, the salt is sodium chloride in an amount ranging from 4 to 4.5 mg/g, and the sugar is sucrose in an amount ranging from 40 to 50 mg/g.

In some embodiments, the polyalkylene oxide-asparaginase is present in an amount of 750 IU/mL, the polyalkylene oxide group includes a polyethylene glycol group with a molecular weight of 5,000 daltons, the asparaginase is *E. coli* asparaginase, the linker is a urethane linker, the buffer is a phosphate buffer including dibasic sodium phosphate in an amount of 2.79 mg/g and monobasic sodium phosphate in an amount of 0.6 mg/g, the salt is sodium chloride in an amount of 4.25 mg/g, and the sugar is sucrose in an amount of 45 mg/g.

In some embodiments, the polyalkylene oxide-asparaginase is present in an amount of 750 IU/mL, the polyalkylene oxide group includes a polyethylene glycol group with a molecular weight of 5,000 daltons, the asparaginase is *E. coli* asparaginase, the linker is a succinate linker, the buffer is a phosphate buffer including dibasic sodium phosphate in an amount ranging from 2.5 to 3 mg/g and monobasic sodium phosphate in an amount ranging from 0.5 to 0.7 mg/g, the salt is sodium chloride in an amount ranging from 4 to 4.5 mg/g, and the sugar is sucrose in an amount ranging from 40 to 50 mg/g.

In some embodiments, the polyalkylene oxide-asparaginase is present in an amount of 750 IU/mL, the polyalkylene oxide group includes a polyethylene glycol group with a molecular weight of 5,000 daltons, the asparaginase is *E. coli* asparaginase, the linker is a succinate linker, the buffer is a phosphate buffer including dibasic sodium phosphate in an amount of 2.79 mg/g and monobasic sodium phosphate in an amount of 0.6 mg/g, the salt is sodium chloride in an amount of 4.25 mg/g, and the sugar is sucrose in an amount of 45 mg/g.

In another embodiment, the present disclosure provides a method of making a lyophilized polyalkylene oxide-asparaginase composition by lyophilizing an aqueous concentrate composition in a manner sufficient to produce a lyophilized storage stable polyalkylene oxide-asparaginase composition. The aqueous concentrate composition includes a polyalkylene oxide-asparaginase having a polyalkylene oxide group covalently linked by a linker to an asparaginase, a buffer, a salt, and a sugar.

In some embodiments, the aqueous concentrate composition includes 1,500 to 3,000 IU/mL of polyalkylene oxide-asparaginase.

In some embodiments, the aqueous concentrate composition includes 0.1 to 0.5 wt. % dibasic sodium phosphate.

In some embodiments, the aqueous concentrate composition includes 0.01 to 0.1 wt. % monobasic sodium phosphate.

In some embodiments, the aqueous concentrate composition includes 0.1 to 1 wt. % sodium chloride.

In some embodiments, the aqueous concentrate composition includes sucrose. In some embodiments, the sucrose is present in an amount ranging from 1 to 10 wt. %. In some embodiments, the method also includes producing the aqueous concentrate composition.

In some embodiments, the method also includes introducing the aqueous concentrate composition into a unit dosage container and lyophilizing the aqueous concentrate composition in the unit dosage container. In some embodiments, the unit dosage container is a vial. In some embodiments, the vial is a glass vial. In some embodiments, the method also includes sealing the lyophilized composition in the unit dosage container.

In some embodiments, the polyalkylene oxide group includes a polyethylene glycol group. In some embodiments, the polyethylene glycol group has a molecular weight ranging from 2,000 to 10,000 daltons. In some embodiments, the polyethylene glycol group has a molecular weight of 5,000 daltons.

In some embodiments, the asparaginase is *E. coli* asparaginase.

In some embodiments, the linker is a urethane linker. In some embodiments, the linker is a succinate linker.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a urethane linker, the buffer is a phosphate buffer including dibasic sodium phosphate in an amount ranging from 0.25 to 0.3 wt. % and monobasic sodium phosphate in an amount ranging from 0.05 to 0.07 wt. %, the salt is sodium chloride in an amount ranging from 0.4 to 0.45 wt. %, and the sugar is sucrose in an amount ranging from 4 to 5 wt. %.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a succinate linker, the buffer is a phosphate buffer including dibasic sodium phosphate in an amount ranging from 0.25 to 0.3 wt. % and monobasic sodium phosphate in an amount ranging from 0.05 to 0.07 wt. %, the salt is sodium chloride in an amount ranging from 0.4 to 0.45 wt. %, and the sugar is sucrose in an amount ranging from 4 to 5 wt. %.

In other embodiments, the present disclosure provides a kit that includes two more unit dosage containers each containing a lyophilized storage stable composition. The lyophilized storage stable composition includes a polyalkylene oxide-asparaginase having a polyalkylene oxide group covalently linked by a linker to an asparaginase, a buffer, a salt, and a sugar.

In some embodiments, the polyalkylene oxide group includes a polyethylene glycol group. In some embodiments, the polyethylene glycol group has a molecular weight ranging from 2,000 to 10,000 daltons. In some embodiments, the polyethylene glycol group has a molecular weight of 5,000 daltons.

In some embodiments, the asparaginase is *E. coli* asparaginase.

In some embodiments, the linker is a urethane linker. In some embodiments, the linker is a succinate linker.

In some embodiments, the polyalkylene oxide-asparaginase is present in an amount ranging from 500 to 1,000 IU/g.

In some embodiments, the buffer includes a phosphate buffer. In some embodiments, the phosphate buffer includes dibasic sodium phosphate and monobasic sodium phosphate. In some embodiments, the dibasic sodium phosphate is present in an amount ranging from 0.1 to 0.5 wt. %. In some embodiments, the monobasic sodium phosphate is present in an amount ranging from 0.01 to 0.1 wt. %.

In some embodiments, the salt is sodium chloride. In some embodiments, the sodium chloride is present in an amount ranging from 0.1 to 1 wt. %.

In some embodiments, the sugar includes a disaccharide. In some embodiments, the disaccharide includes sucrose. In some embodiments, the sugar includes sucrose in an amount ranging from 1 to 10 wt. %.

In some embodiments, the unit dosage containers are vials. In some embodiments, the vials are glass vials. In some embodiments, the unit dosage containers are sealed.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a urethane linker, the buffer is a phosphate buffer including dibasic sodium phosphate in an amount ranging from 0.25 to 0.3 wt. % and monobasic sodium phosphate in an amount ranging from 0.05 to 0.07 wt. %, the salt is sodium chloride in an amount ranging from 0.4 to 0.45 wt. %, and the sugar is sucrose in an amount ranging from 4 to 5 wt. %.

In some embodiments, the polyalkylene oxide-asparaginase is present in an amount of 750 IU/g, the polyalkylene oxide group includes a polyethylene glycol group with a molecular weight of 5,000 daltons, the asparaginase is *E. coli* asparaginase, the linker is a succinate linker, the buffer is a phosphate buffer including dibasic sodium phosphate in an amount ranging from 0.25 to 0.3 wt. % and monobasic sodium phosphate in an amount ranging from 0.05 to 0.07 wt. %, the salt is sodium chloride in an amount ranging from 0.4 to 0.45 wt. %, and the sugar is sucrose in an amount ranging from 4 to 5 wt. %.

In another embodiment, the present disclosure provides a method of treating a subject for acute myeloid leukemia (AML). The method includes administering to the subject a dosage of a polyalkylene oxide-asparaginase effective to treat the subject for AML, where the polyalkylene oxide-asparaginase has a polyalkylene oxide group covalently linked by a linker to an asparagmase.

In some embodiments, the polyalkylene oxide group includes a polyethylene glycol group. In some embodiments, the polyethylene glycol group has a molecular weight ranging from 2,000 to 10,000 daltons. In some embodiments, the polyethylene glycol group has a molecular weight of 5,000 daltons.

In some embodiments, the asparaginase is *E. coli* asparaginase.

In some embodiments, the linker is a urethane linker. In some embodiments, the linker is a succinate linker.

In some embodiments, the dosage includes 700 to 800 IU/mL of the polyalkylene oxide-asparagmase.

In some embodiments, the dosage includes a buffer and a salt. In some embodiments, the buffer includes a phosphate buffer. In some embodiments, the phosphate buffer includes dibasic sodium phosphate and monobasic sodium phosphate. In some embodiments, the dosage includes 5.25 to 5.75 mg/g dibasic sodium phosphate. In some embodiments, the dosage includes 1.0 to 1.5 mg/g monobasic sodium phosphate. In some embodiments, the salt is sodium chloride. In some embodiments, the dosage includes 8 to 9 mg/g sodium chloride.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a urethane linker, the buffer is a phosphate buffer that includes 5.25 to 5.75 mg/g dibasic sodium phosphate and 1 to 1.5 mg/g monobasic sodium phosphate, and the salt includes 8 to 9 mg/g sodium chloride.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a urethane linker, the buffer is a phosphate buffer that includes 5.58 mg/g dibasic sodium phosphate and 1.29 mg/g monobasic sodium phosphate, and the salt includes 8.5 mg/g sodium chloride.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a succinate linker, the buffer is a phosphate buffer that includes 5.25 to 5.75 mg/g dibasic sodium phosphate and 1 to 1.5 mg/g monobasic sodium phosphate, and the salt includes 8 to 9 mg/g sodium chloride.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a succinate linker, the buffer is a phosphate buffer that includes 5.58 mg/g dibasic sodium phosphate and 1.29 mg/g monobasic sodium phosphate, and the salt includes 8.5 mg/g sodium chloride.

In some embodiments, the dosage includes a buffer, a salt and a sugar. In some embodiments, the buffer includes a phosphate buffer. In some embodiments, the phosphate buffer includes dibasic sodium phosphate and monobasic sodium phosphate. In some embodiments, the dosage includes 2.5 to 3 mg/g dibasic sodium phosphate. In some embodiments, the dosage includes 0.45 to 0.75 mg/g monobasic sodium phosphate. In some embodiments, the salt is sodium chloride. In some embodiments, the dosage includes 4 to 4.5 mg/g sodium chloride. In some embodiments, the sugar includes a disaccharide. In some embodiments, the disaccharide includes sucrose. In some embodiments, the sucrose is present in an amount ranging from 40 to 50 mg/g.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a urethane linker, the buffer is a phosphate buffer that includes 2.5 to 3 mg/g dibasic sodium phosphate and 0.5 to 0.7 mg/g monobasic sodium phosphate, the salt includes 4 to 4.5 mg/g sodium chloride, and the sugar includes 40 to 50 mg/g sucrose.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a urethane linker, the buffer is a phosphate buffer that includes 2.79 mg/g dibasic sodium phosphate and 0.6 mg/g monobasic sodium phosphate, the salt includes 4.25 mg/g sodium chloride, and the sugar includes 45 mg/g sucrose.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a succinate linker, the buffer is a phosphate buffer that includes 2.5 to 3 mg/g dibasic sodium phosphate and 0.5 to 0.7 mg/g monobasic sodium phosphate, the salt includes 4 to 4.5 mg/g sodium chloride, and the sugar includes 40 to 50 mg/g sucrose.

In some embodiments, the dosage includes 750 IU/mL of the polyalkylene oxide-asparaginase, the polyethylene glycol group has a molecular weight of 5,000 daltons, the asparaginase is *E. coli* asparaginase, the linker is a succinate linker, the buffer is a phosphate buffer that includes 2.79 mg/g dibasic sodium phosphate and 0.6 mg/g monobasic sodium phosphate, the salt includes 4.25 mg/g sodium chloride, and the sugar includes 45 mg/g sucrose.

In some embodiments, the method also includes producing the dosage by reconstituting a lyophilized storage stable composition.

In some embodiments, the dosage delivers from 1,500 to 3,000 IU/m$^2$ of polyalkylene oxide-asparaginase to the subject. In some embodiments, the dosage delivers from 2,000 to 2,750 IU/m$^2$ of polyalkylene oxide-asparaginase to the subject.

In some embodiments, the subject has been prescribed a treatment regimen that includes an induction phase, a consolidation phase and a maintenance phase. In some embodiments, the method includes administering a single dosage to the subject in the induction phase and multiple dosages during the maintenance phase. In some embodiments, the multiple dosages are administered to the subject by administering a dosage to the subject every 3 weeks. In some embodiments, the multiple dosages are administered to the subject by administering a dosage to the subject every 2 weeks.

In some embodiments, the subject is a juvenile. In some embodiments, the subject is an adult.

Although the foregoing embodiments have been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of the embodiments of the present disclosure and are included within its spirit and scope. Furthermore, all examples and conditional language recited herein are principally intended to aid the reader in understanding the principles of the embodiments of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the embodiments of the present disclosure, therefore, is not intended to be limited to the embodiments shown and described herein. Rather, the scope and spirit of embodiments of the present disclosure is embodied by the appended claims.

What is claimed is:

1. A lyophilized composition prepared by lyophilizing an aqueous composition comprising, per gram of the aqueous composition:
   750 IU of a polyalkylene oxide-asparaginase;
   about 2.79 mg of dibasic sodium phosphate;
   about 0.6 mg of monobasic sodium phosphate;
   about 4.25 mg of sodium chloride; and
   about 45 mg of sucrose, wherein the polyalkylene oxide-asparaginase comprises an asparaginase covalently linked to a polyalkylene oxide group that is a polyethylene glycol, and wherein the lyophilized composition is substantially dehydrated, comprising less than 25% water.

2. The lyophilized composition according to claim 1, wherein the polyalkylene oxide group is a monomethoxypolyethylene glycol.

3. The lyophilized composition according to claim 1, wherein the polyalkylene oxide is covalently linked by a urethane or succinate linker to the asparaginase.

4. The lyophilized composition according to claim 1, wherein the composition further comprises sodium hydroxide, hydrochloric acid, or a combination thereof.

5. The lyophilized composition of claim 1, prepared by a process comprising:

providing an un-lyophilized polyalkylene oxide-asparaginase;
   combining the un-lyophilized polyalkylene oxide-asparaginase in an aqueous solution with dibasic sodium phosphate, monobasic sodium phosphate, sodium chloride and sucrose to yield a mixture; and
   lyophilizing the mixture to form the lyophilized composition.

6. A kit comprising one or more unit dosage containers each containing a lyophilized composition according to claim 1.

7. A method of making a lyophilized polyalkylene oxide-asparaginase-composition, the method comprising lyophilizing an aqueous composition comprising, per gram of the aqueous composition:
   750 IU of a polyalkylene oxide-asparaginase;
   about 2.79 mg of dibasic sodium phosphate;
   about 0.6 mg of monobasic sodium phosphate;
   about 4.25 mg of sodium chloride; and
   about 45 mg of sucrose,
   wherein the polyalkylene oxide-asparaginase comprises an asparaginase covalently linked to a polyalkylene oxide group that is a polyethylene glycol, and wherein the lyophilized composition is substantially dehydrated, comprising less than 25% water.

8. A liquid composition prepared by reconstituting with water a lyophilized composition comprising polyalkylene oxide-asparaginase, dibasic sodium phosphate, monobasic sodium phosphate, sodium chloride, and sucrose, wherein the liquid composition comprises, per gram of aqueous solution:
   750 IU of a polyalkylene oxide-asparaginase;
   about 2.79 mg of dibasic sodium phosphate;
   about 0.6 mg of monobasic sodium phosphate;
   about 4.25 mg of sodium chloride; and
   about 45 mg of sucrose,
   wherein the polyalkylene oxide-asparaginase comprises an asparaginase covalently linked to a polyalkylene oxide group that is a polyethylene glycol.

9. A method of deaminating asparagine in a subject, the method comprising:
   providing the liquid composition of claim 8; and
   administering the liquid composition to the subject to deaminate asparagine in the subject.

10. The method according to claim 9, wherein the method is a method of treating the subject for a neoplastic condition.

* * * * *